United States Patent
Meadows et al.

(10) Patent No.: US 8,886,322 B2
(45) Date of Patent: Nov. 11, 2014

(54) SYSTEM FOR STIMULATING A HYPOGLOSSAL NERVE FOR CONTROLLING THE POSITION OF A PATIENT'S TONGUE

(71) Applicant: ImThera Medical, Inc., San Diego, CA (US)

(72) Inventors: Paul M. Meadows, Glendale, CA (US); Marcelo G. Lima, San Diego, CA (US); Stanley R. Craig, Westport, MA (US); Faisal N. Zaidi, San Diego, CA (US); Monir M. Elias, San Diego, CA (US)

(73) Assignee: Imthera Medical, Inc., San Diego, CA (US)

( * ) Notice: Subject to any disclaimer, the term of this patent is extended or adjusted under 35 U.S.C. 154(b) by 0 days.

(21) Appl. No.: 13/779,938

(22) Filed: Feb. 28, 2013

(65) Prior Publication Data
US 2013/0253627 A1    Sep. 26, 2013

Related U.S. Application Data

(63) Continuation of application No. 12/787,206, filed on May 25, 2010, now abandoned.

(60) Provisional application No. 61/259,893, filed on Nov. 10, 2009.

(51) Int. Cl.
| | |
|---|---|
| *A61N 1/00* | (2006.01) |
| *A61N 1/372* | (2006.01) |
| *G06F 19/00* | (2011.01) |
| *A61N 1/02* | (2006.01) |
| *A61N 1/05* | (2006.01) |
| *A61N 1/36* | (2006.01) |
| *A61N 1/378* | (2006.01) |

(52) U.S. Cl.
CPC .......... *A61N 1/0556* (2013.01); *A61N 1/37247* (2013.01); *A61N 1/3611* (2013.01); *G06F 19/3406* (2013.01); *A61N 1/3787* (2013.01); *A61N 1/3605* (2013.01); *A61N 1/36146* (2013.01); *A61N 1/025* (2013.01)
USPC ................................. 607/42; 607/17; 607/66

(58) Field of Classification Search
CPC .. A61N 1/3601; A61N 1/3611; A61N 1/3605
USPC ................................................ 607/42, 17, 66
See application file for complete search history.

(56) References Cited

U.S. PATENT DOCUMENTS

| | | | |
|---|---|---|---|
| 4,424,812 | A | 1/1984 | Lesnick |
| 4,602,624 | A | 7/1986 | Naples et al. |

(Continued)

FOREIGN PATENT DOCUMENTS

| | | |
|---|---|---|
| EP | 1524007 | 4/2005 |
| EP | 2116274 A2 | 11/2009 |

(Continued)

OTHER PUBLICATIONS

Final Office Action mailed Feb. 9, 2012 in connection with U.S. Appl. No. 13/097,172.

(Continued)

*Primary Examiner* — Christopher D Koharski
*Assistant Examiner* — Philip Edwards
(74) *Attorney, Agent, or Firm* — Morgan, Lewis & Bockius LLP

(57) ABSTRACT

A system for controlling a position of a patient's tongue includes attaching at least one electrode to the patient's Hypoglossal nerve and applying an electric signal through the electrode to at least one targeted motor efferent located within the Hypoglossal nerve to stimulate at least one muscle of the tongue. The system may also include the use of more than one contact to target more than one motor efferent and stimulating more than one muscle. The stimulation load to maintain the position of the tongue may be shared by each muscle. The position of the patient's tongue may be controlled in order to prevent obstructive sleep apnea.

13 Claims, 55 Drawing Sheets

(56) References Cited

U.S. PATENT DOCUMENTS

| | | | |
|---|---|---|---|
| 5,094,242 | A | 3/1992 | Gleason et al. |
| 5,095,905 | A | 3/1992 | Klepinski |
| 5,123,425 | A | 6/1992 | Shannon, Jr. et al. |
| 5,133,354 | A | 7/1992 | Kallok |
| 5,146,918 | A | 9/1992 | Kallok et al. |
| 5,158,080 | A | 10/1992 | Kallok |
| 5,174,287 | A | 12/1992 | Kallok et al. |
| 5,190,053 | A | 3/1993 | Meer |
| 5,211,173 | A | 5/1993 | Kallok et al. |
| 5,215,082 | A | 6/1993 | Kallok et al. |
| 5,233,983 | A | 8/1993 | Markowitz |
| 5,281,219 | A | 1/1994 | Kallok |
| 5,300,094 | A | 4/1994 | Kallok et al. |
| 5,344,438 | A | 9/1994 | Testerman et al. |
| 5,483,969 | A | 1/1996 | Testerman et al. |
| 5,522,862 | A | 6/1996 | Testerman et al. |
| 5,540,731 | A | 7/1996 | Testerman |
| 5,540,732 | A | 7/1996 | Testerman |
| 5,540,733 | A | 7/1996 | Testerman et al. |
| 5,545,201 | A | 8/1996 | Helland et al. |
| 5,546,952 | A | 8/1996 | Erickson |
| 5,591,216 | A | 1/1997 | Testerman et al. |
| 5,713,922 | A | 2/1998 | King |
| 5,771,891 | A | 6/1998 | Gozani |
| 5,837,006 | A | 11/1998 | Ocel et al. |
| 5,871,512 | A | 2/1999 | Hemming et al. |
| 5,944,680 | A | 8/1999 | Christopherson et al. |
| 5,988,171 | A | 11/1999 | Sohn et al. |
| 6,021,352 | A | 2/2000 | Christopherson et al. |
| 6,051,017 | A | 4/2000 | Loeb et al. |
| 6,132,384 | A | 10/2000 | Christopherson et al. |
| 6,175,767 | B1 | 1/2001 | Doyle, Sr. |
| 6,212,435 | B1 | 4/2001 | Lattner et al. |
| 6,240,316 | B1 | 5/2001 | Richmond et al. |
| 6,251,126 | B1 | 6/2001 | Ottenhoff et al. |
| 6,266,560 | B1 | 7/2001 | Zhang et al. |
| 6,269,269 | B1 | 7/2001 | Ottenhoff et al. |
| 6,345,202 | B2 | 2/2002 | Richmond et al. |
| 6,408,852 | B2 | 6/2002 | Tielemans |
| 6,409,676 | B2 | 6/2002 | Ruton et al. |
| 6,415,174 | B1 | 7/2002 | Bebehani et al. |
| 6,427,689 | B1 | 8/2002 | Estes et al. |
| 6,432,956 | B1 | 8/2002 | Dement et al. |
| 6,454,724 | B1 | 9/2002 | Greene |
| 6,456,866 | B1 | 9/2002 | Tyler et al. |
| 6,475,156 | B1 | 11/2002 | Vega |
| 6,488,634 | B1 | 12/2002 | Rapoport et al. |
| 6,516,802 | B2 | 2/2003 | Hansen et al. |
| 6,516,805 | B1 | 2/2003 | Thornton |
| 6,529,752 | B2 | 3/2003 | Krausman et al. |
| 6,536,439 | B1 | 3/2003 | Palmisano |
| 6,555,564 | B1 | 4/2003 | Radulovacki et al. |
| 6,572,543 | B1 | 6/2003 | Christopherson et al. |
| 6,574,507 | B1 | 6/2003 | Bonnet |
| 6,580,944 | B1 | 6/2003 | Katz et al. |
| 6,586,478 | B2 | 7/2003 | Ackman et al. |
| 6,587,725 | B1 | 7/2003 | Durand et al. |
| 6,594,370 | B1 | 7/2003 | Anderson |
| 6,595,215 | B2 | 7/2003 | Wood |
| 6,613,779 | B2 | 9/2003 | Mondadori et al. |
| 6,629,527 | B1 | 10/2003 | Estes et al. |
| 6,635,021 | B1 | 10/2003 | Sullivan et al. |
| 6,636,767 | B1 | 10/2003 | Knudson et al. |
| 6,641,542 | B2 | 11/2003 | Cho et al. |
| 6,658,301 | B2 | 12/2003 | Loeb et al. |
| 6,666,830 | B1 | 12/2003 | Lehrman et al. |
| 6,671,907 | B1 | 1/2004 | Zuberi |
| 6,705,315 | B2 | 3/2004 | Sullivan et al. |
| 6,727,242 | B2 | 4/2004 | Rudulovacki et al. |
| 6,729,335 | B1 | 5/2004 | Halstrom |
| 6,731,984 | B2 | 5/2004 | Cho et al. |
| 6,752,766 | B2 | 6/2004 | Kowallik et al. |
| 6,761,167 | B1 | 7/2004 | Nadjafizadeh et al. |
| 6,761,168 | B1 | 7/2004 | Nadjafizadeh et al. |
| 6,766,802 | B1 | 7/2004 | Keropian |
| 6,770,022 | B2 | 8/2004 | Mechlenburg et al. |
| 6,770,037 | B2 | 8/2004 | Sullivan et al. |
| 6,773,404 | B2 | 8/2004 | Poezevera et al. |
| 6,776,162 | B2 | 8/2004 | Wood |
| 6,788,975 | B1 | 9/2004 | Whitehurst et al. |
| 6,793,629 | B2 | 9/2004 | Rapoport et al. |
| 6,807,967 | B2 | 10/2004 | Wood |
| 6,811,538 | B2 | 11/2004 | Westbrook et al. |
| 6,814,074 | B1 | 11/2004 | Nadjafizadeh et al. |
| 6,818,665 | B2 | 11/2004 | Wennerholm et al. |
| 6,835,740 | B2 | 12/2004 | Rubin et al. |
| 6,857,149 | B2 | 2/2005 | Hoggatt et al. |
| 6,878,121 | B2 | 4/2005 | Krausman et al. |
| 6,881,192 | B1 | 4/2005 | Park |
| 6,884,596 | B2 | 4/2005 | Civelli et al. |
| 6,890,306 | B2 | 5/2005 | Poezevera |
| 6,893,405 | B2 | 5/2005 | Kumar et al. |
| 6,901,292 | B2 | 5/2005 | Hrdlicka et al. |
| 6,904,320 | B2 | 6/2005 | Park et al. |
| 6,918,394 | B2 | 7/2005 | Matsuda et al. |
| 6,928,324 | B2 | 8/2005 | Park et al. |
| 6,964,641 | B2 | 11/2005 | Cho et al. |
| 6,999,819 | B2 | 2/2006 | Swoyer et al. |
| 7,003,352 | B1 | 2/2006 | Whitehurst |
| 7,092,763 | B1 | 8/2006 | Griffith et al. |
| 7,184,836 | B1 | 2/2007 | Meadows et al. |
| 7,245,971 | B2 | 7/2007 | Park et al. |
| 7,570,997 | B2 | 8/2009 | Lovett et al. |
| 7,644,714 | B2 | 1/2010 | Atkinson et al. |
| 7,680,538 | B2 | 3/2010 | Durand et al. |
| 7,725,195 | B2 | 5/2010 | Lima et al. |
| 7,809,442 | B2 | 10/2010 | Bolea et al. |
| 2001/0000346 | A1 | 4/2001 | Ruton et al. |
| 2001/0001125 | A1 | 5/2001 | Schulman et al. |
| 2001/0010010 | A1 | 7/2001 | Richmond et al. |
| 2001/0015204 | A1 | 8/2001 | Hansen et al. |
| 2001/0018557 | A1 | 8/2001 | Lynn et al. |
| 2001/0027793 | A1 | 10/2001 | Tielemans |
| 2001/0041719 | A1 | 11/2001 | Mondadori et al. |
| 2001/0046988 | A1 | 11/2001 | Iglehart |
| 2002/0007127 | A1 | 1/2002 | Sullivan et al. |
| 2002/0015740 | A1 | 2/2002 | Ackman et al. |
| 2002/0037533 | A1 | 3/2002 | Civelli et al. |
| 2002/0049479 | A1 | 4/2002 | Pitts |
| 2002/0059935 | A1 | 5/2002 | Wood |
| 2002/0086870 | A1 | 7/2002 | Radulovacki et al. |
| 2002/0092527 | A1 | 7/2002 | Wood |
| 2002/0095076 | A1 | 7/2002 | Krausman et al. |
| 2002/0099033 | A1 | 7/2002 | Meyer et al. |
| 2002/0100477 | A1 | 8/2002 | Sullivan et al. |
| 2002/0124848 | A1 | 9/2002 | Sullivan et al. |
| 2002/0124849 | A1 | 9/2002 | Billette De Villemeur et al. |
| 2002/0144684 | A1 | 10/2002 | Moone |
| 2002/0144685 | A1 | 10/2002 | Ivanovich et al. |
| 2002/0165246 | A1 | 11/2002 | Holman |
| 2002/0165462 | A1 | 11/2002 | Westbrook et al. |
| 2002/0169384 | A1 | 11/2002 | Kowallik et al. |
| 2002/0173707 | A1 | 11/2002 | Lynn et al. |
| 2002/0175821 | A1 | 11/2002 | Ruppel |
| 2002/0183306 | A1 | 12/2002 | Howard, Jr. |
| 2002/0193697 | A1 | 12/2002 | Cho et al. |
| 2002/0193839 | A1 | 12/2002 | Cho et al. |
| 2003/0004423 | A1 | 1/2003 | Lavie et al. |
| 2003/0015198 | A1 | 1/2003 | Heeke et al. |
| 2003/0021772 | A1 | 1/2003 | Birkmayer |
| 2003/0053956 | A1 | 3/2003 | Hofmann |
| 2003/0055346 | A1 | 3/2003 | Rapoport et al. |
| 2003/0055348 | A1 | 3/2003 | Chazal et al. |
| 2003/0056785 | A1 | 3/2003 | Narihiko et al. |
| 2003/0083241 | A1 | 5/2003 | Young |
| 2003/0093131 | A1 | 5/2003 | Loeb et al. |
| 2003/0130266 | A1 | 7/2003 | Radulovacki et al. |
| 2003/0130589 | A1 | 7/2003 | Poezevera |
| 2003/0139680 | A1 | 7/2003 | Sheldon |
| 2003/0139691 | A1 | 7/2003 | Kumar et al. |
| 2003/0139789 | A1 | 7/2003 | Tvinnereim et al. |
| 2003/0153953 | A1* | 8/2003 | Park et al. .................. 607/17 |
| 2003/0153954 | A1 | 8/2003 | Park et al. |
| 2003/0153955 | A1 | 8/2003 | Park et al. |

(56) References Cited

U.S. PATENT DOCUMENTS

| | | |
|---|---|---|
| 2003/0153956 A1 | 8/2003 | Park et al. |
| 2003/0163059 A1 | 8/2003 | Poezevera et al. |
| 2003/0167018 A1 | 9/2003 | Wycoff |
| 2003/0172462 A1 | 9/2003 | Hoggatt et al. |
| 2003/0176788 A1 | 9/2003 | Crutchfield et al. |
| 2003/0181958 A1 | 9/2003 | Dobak, III |
| 2003/0183227 A1 | 10/2003 | Klemperer |
| 2003/0195140 A1 | 10/2003 | Ackman et al. |
| 2003/0195571 A1 | 10/2003 | Burnes et al. |
| 2003/0204213 A1 | 10/2003 | Jensen et al. |
| 2003/0216789 A1 | 11/2003 | Deem et al. |
| 2003/0232839 A1 | 12/2003 | Hangauer et al. |
| 2003/0235313 A1 | 12/2003 | Kurzweil et al. |
| 2003/0236228 A1 | 12/2003 | Radulovacki et al. |
| 2004/0002516 A1 | 1/2004 | Mondadori et al. |
| 2004/0002742 A1 | 1/2004 | Florio |
| 2004/0006339 A1 | 1/2004 | Underwood et al. |
| 2004/0006375 A1 | 1/2004 | Poezevera |
| 2004/0016433 A1 | 1/2004 | Estes et al. |
| 2004/0020493 A1 | 2/2004 | Wood |
| 2004/0025885 A1 | 2/2004 | Payne, Jr. |
| 2004/0029869 A1 | 2/2004 | Iglehart, III |
| 2004/0030224 A1 | 2/2004 | Sotos et al. |
| 2004/0055597 A1 | 3/2004 | Virr et al. |
| 2004/0059240 A1 | 3/2004 | Cho et al. |
| 2004/0082519 A1 | 4/2004 | Hedner et al. |
| 2004/0087866 A1 | 5/2004 | Bowman et al. |
| 2004/0087878 A1 | 5/2004 | Krausman et al. |
| 2004/0097871 A1 | 5/2004 | Yerushalmy |
| 2004/0111041 A1 | 6/2004 | Ni et al. |
| 2004/0127572 A1 | 7/2004 | Carley et al. |
| 2004/0134491 A1 | 7/2004 | Pflueger et al. |
| 2004/0138719 A1 | 7/2004 | Cho et al. |
| 2004/0144391 A1 | 7/2004 | Brady et al. |
| 2004/0146873 A1 | 7/2004 | Ptacek et al. |
| 2004/0157813 A1 | 8/2004 | Wennerholm et al. |
| 2004/0176695 A1 | 9/2004 | Poezevara |
| 2004/0176809 A1 | 9/2004 | Cho et al. |
| 2004/0186523 A1 | 9/2004 | Florio |
| 2004/0187873 A1 | 9/2004 | Brown |
| 2004/0200472 A1 | 10/2004 | Gold |
| 2004/0210261 A1 | 10/2004 | King et al. |
| 2004/0215095 A1 | 10/2004 | Lee et al. |
| 2004/0225226 A1 | 11/2004 | Lehrman et al. |
| 2004/0235807 A1 | 11/2004 | Weinrich et al. |
| 2004/0254493 A1 | 12/2004 | Chervin et al. |
| 2005/0008587 A1 | 1/2005 | Schulz et al. |
| 2005/0015117 A1 | 1/2005 | Gerber |
| 2005/0016536 A1 | 1/2005 | Rapoport et al. |
| 2005/0020930 A1 | 1/2005 | Salisbury et al. |
| 2005/0022821 A1 | 2/2005 | Jeppesen |
| 2005/0027207 A1 | 2/2005 | Westbrook et al. |
| 2005/0031688 A1 | 2/2005 | Ayala |
| 2005/0034730 A1 | 2/2005 | Wood |
| 2005/0038013 A1 | 2/2005 | Gold |
| 2005/0039757 A1 | 2/2005 | Wood |
| 2005/0042589 A1 | 2/2005 | Hatlestad et al. |
| 2005/0043645 A1 | 2/2005 | Ono et al. |
| 2005/0043652 A1 | 2/2005 | Lovett et al. |
| 2005/0045190 A1 | 3/2005 | Bennett |
| 2005/0048538 A1 | 3/2005 | Mignot et al. |
| 2005/0061315 A1 | 3/2005 | Lee et al. |
| 2005/0061320 A1 | 3/2005 | Lee et al. |
| 2005/0061326 A1 | 3/2005 | Payne, Jr. |
| 2005/0076906 A1 | 4/2005 | Johnson |
| 2005/0080461 A1 | 4/2005 | Stahmann et al. |
| 2005/0081854 A1 | 4/2005 | Nadjafizadeh et al. |
| 2005/0085738 A1 | 4/2005 | Stahmann et al. |
| 2005/0085874 A1 * | 4/2005 | Davis et al. .................. 607/66 |
| 2005/0090871 A1 | 4/2005 | Cho et al. |
| 2005/0101833 A1 | 5/2005 | Hsu et al. |
| 2005/0113646 A1 | 5/2005 | Sotos et al. |
| 2005/0113710 A1 | 5/2005 | Stahmann et al. |
| 2005/0119285 A1 | 6/2005 | Matos et al. |
| 2005/0126574 A1 | 6/2005 | Wood |
| 2005/0133026 A1 | 6/2005 | Seleznev et al. |
| 2005/0143617 A1 | 6/2005 | Auphan |
| 2005/0148893 A1 | 7/2005 | Misczynski et al. |
| 2005/0148897 A1 | 7/2005 | Cho et al. |
| 2005/0149146 A1 | 7/2005 | Boveja et al. |
| 2005/0150504 A1 | 7/2005 | Heeke et al. |
| 2005/0215947 A1 | 9/2005 | Heruth et al. |
| 2005/0240253 A1 | 10/2005 | Tyler et al. |
| 2005/0258242 A1 | 11/2005 | Zarembo |
| 2005/0277999 A1 | 12/2005 | Strother et al. |
| 2005/0288729 A1 * | 12/2005 | Libbus et al. .................. 607/42 |
| 2006/0095078 A1 | 5/2006 | Tronnes |
| 2006/0095088 A1 | 5/2006 | De Ridder |
| 2006/0122653 A1 | 6/2006 | Bradley et al. |
| 2006/0149337 A1 | 7/2006 | John |
| 2006/0212096 A1 | 9/2006 | Stevenson |
| 2006/0224211 A1 | 10/2006 | Durand et al. |
| 2007/0021794 A1 | 1/2007 | Kieval et al. |
| 2007/0043398 A1 | 2/2007 | Ternes et al. |
| 2007/0055308 A1 | 3/2007 | Haller et al. |
| 2007/0066997 A1 | 3/2007 | He et al. |
| 2007/0100399 A1 | 5/2007 | Parramon et al. |
| 2007/0100411 A1 | 5/2007 | Bonde |
| 2007/0129768 A1 | 6/2007 | He et al. |
| 2007/0150006 A1 | 6/2007 | Libbus et al. |
| 2007/0150022 A1 | 6/2007 | Ujhazy et al. |
| 2007/0173893 A1 | 7/2007 | Pitts |
| 2007/0179557 A1 | 8/2007 | Maschino et al. |
| 2007/0233204 A1 | 10/2007 | Lima et al. |
| 2007/0255366 A1 | 11/2007 | Gerber et al. |
| 2007/0255367 A1 | 11/2007 | Gerber et al. |
| 2007/0288064 A1 | 12/2007 | Butson et al. |
| 2008/0021506 A1 | 1/2008 | Grocela et al. |
| 2008/0039904 A1 | 2/2008 | Bulkes et al. |
| 2008/0039916 A1 | 2/2008 | Colliou et al. |
| 2008/0091246 A1 | 4/2008 | Carey et al. |
| 2008/0097554 A1 | 4/2008 | Payne et al. |
| 2008/0103407 A1 | 5/2008 | Bolea et al. |
| 2008/0103544 A1 | 5/2008 | Weiner |
| 2008/0103545 A1 | 5/2008 | Bolea et al. |
| 2008/0109047 A1 | 5/2008 | Pless |
| 2008/0114230 A1 | 5/2008 | Addis |
| 2008/0139913 A1 | 6/2008 | Schulman |
| 2008/0172109 A1 | 7/2008 | Rahman et al. |
| 2008/0288025 A1 | 11/2008 | Peterson |
| 2009/0118796 A1 | 5/2009 | Chen et al. |
| 2009/0210042 A1 | 8/2009 | Kowalczewski |
| 2009/0270904 A1 | 10/2009 | Birk et al. |
| 2010/0139667 A1 | 6/2010 | Atkinson et al. |
| 2011/0213438 A1 | 9/2011 | Lima et al. |

FOREIGN PATENT DOCUMENTS

| | | |
|---|---|---|
| WO | 9900058 A1 | 1/1999 |
| WO | 02087433 A1 | 11/2002 |
| WO | 2007092330 A1 | 8/2007 |
| WO | 2007098200 A2 | 8/2007 |
| WO | 2007098202 A2 | 8/2007 |
| WO | 2007117232 A1 | 10/2007 |
| WO | 2007140584 A1 | 12/2007 |
| WO | 2008005903 A2 | 1/2008 |
| WO | 2008039921 A2 | 4/2008 |
| WO | 2008046190 A1 | 4/2008 |
| WO | 2008048471 A2 | 4/2008 |
| WO | 2008049199 A1 | 5/2008 |
| WO | 2009048580 A1 | 4/2009 |
| WO | 2009048581 A1 | 4/2009 |
| WO | 2009140636 A2 | 11/2009 |
| WO | 2010039853 A1 | 4/2010 |
| WO | 2010059839 A2 | 5/2010 |

OTHER PUBLICATIONS

Office Action mailed Mar. 27, 2012 in connection with U.S. Appl. No. 12/681,799.

Office Action mailed Jun. 21, 2012 in connection with U.S. Appl. No. 12/572,758.

Examiner's Report from Australian Patent Application No. 2007217783 dated Jul. 25, 2011.

(56) References Cited

OTHER PUBLICATIONS

Fairbanks, David W., M.D.; Fairbanks, David N.F., M.D.; Neurostimulation for Obstructive Sleep Apnea; Investigations; ENT Journal; Jan. 1993; pp. 52-57; vol. 72, No. 1; International Pub. Group; Cleveland, OH.

Final Office Action mailed Nov. 4, 2010 in connection with U.S. Appl. No. 11/707,104.

Non-Final Office Action mailed Nov. 5, 2010 in connection with U.S. Appl. No. 12/752,931.

International Search Report from International Application No. PCT/US2010/36070, dated Jul. 21, 2010.

Written Opinion of the International Search Authority Application No. PCT/US2010/036070, dated Jul. 21, 2010.

Office Action from U.S. Appl. No. 11/707,104 dated Jun. 21, 2010.

Gilliam, Edwin E. and Goldberg, Stephen J. Contractile Properties of the Tongue Muscles: Effects of Hypoglossal Nerve and Extracellular Motoneuron Stimulation in Rat, Journal of Neurophysiology, vol. 74, No. 2, Aug. 1995, pp. 547-555.

Nagai, et al., Effect of Aging on Tongue Protrusion Forces in Rats; Dysphagia (2008) 23:116-121.

Pae, Eung-Kwon et al., Short-Term Electrical Stimulation Alters Tongue Muscle Fibre Type Composition; Archives of Oral Biology, vol. 52, Issue 6 (Jun. 2007) 544-551.

Schwartz, et al., Therapeutic Electrical Stimulation of the Hypoglossal Nerve in Obstructive Sleep Apnea, Arch Otolarynogol Head Neck Surg., vol. 127, Oct. 2001, pp. 1216-1223.

Davis, et al., Development of the Bion Microstimulator for Treatment in Obstructive Sleep Apnea, Alfred Mann Foundation, Valencia, California, Jul. 1-5, 2003, IFESS.

Sutlive, et al., Whole-Muscle and Motor-Unit Contractile Properties of the Styloglossus Muscle in Rat, The American Physiological Society, 1999, pp. 584-592.

Smith, et al., Phenotype and Contractile Properties of Mammalian Tongue Muscles Innervated by the Hypoglossal Nerve, Respiratory Physiology and Neurobiology 147 (Feb. 23, 2005) 253-262.

Sawczuk et al., Neural Control of Tongue Movement With Respect to Respiration and Swallowing, Crit Rev Oral Viol Med, 12(I): 18-37 (2001).

Goding, Jr., et al., Relief of Upper Airway Obstruction With Hypoglossal Nerve Stimulation in the Canine, The Larynogscope, Feb. 1998, 108:2, pp. 162-169.

Weiss, Implications of Silicon Monolithic RFICs for Medical Instrumentation and Telemetry, IEEE, 1998 pp. 195-204.

Troyk, Injectible Electronic Identification, Monitoring, and Stimulation Systems, Annu. Rev. Biomed. Eng. 1999, 01:177-209.

Sahin et al., Closed-Loop Stimulation of Hypoglossal Nerve in a Dog Model of Upper Airway Obstruction, IEEE Transactions on Biomedical Engineering, vol. 47, No. 7, pp. 919-925, Jul. 2000.

Yoo et al., Selective Stimulation of the Hypoglossal Nerve With a Multi-Contact Cuff Electrode, 2001 IEEE, pp. 1309-1312.

Yoo et al., Selective Stimulation of the Hypoglossal Nerve: A Fine Approach to Treating Obstructive Sleep Apnea, 2002 IEEE, pp. 2049-2050.

Eisele, M.D., et al. Tongue Neuromuscular and Direct Hypoglossal Nerve Stimulation of Obstructive Sleep Apnea, Otolarynogol Clin N. Am 36 (2003) 501-510.

Tran et al., Development of Asynchronous, Intralingual Electrical Stimulation to Treat Obstructive Sleep Apnea, 2003 IEEE pp. 375-378.

Huang et al., Activation Patterns of the Tongue Muscles With Selective Stimulation of the Hypoglossal Nerve, 2004 IEEE, pp. 4275-4278.

Arndt, Rewiring the Body, BusinessWeek, Mar. 7, 2005, pp. 74-82.

Yoo et al., A Neural Prosthesis for Obstructive Sleep Apnea, 2005 IEEE, pp. 5254-5256.

Wells, The Sleep Racket Who's Making Big Busks Off Your Insomnia? Forbes, Feb. 27, 2006, pp. 80-88.

International Search Report for PCT/US2007/04512 dated Nov. 29, 2007.

International Search Report for PCT/US2008/011598 dated Dec. 12, 2008.

International Search Report for PCT/US2008/011599 dated Dec. 12, 2008.

International Search Report for PCT/US2007/04514 dated Nov. 29, 2007.

Office Action dated Aug. 28, 2009 for U.S. Appl. No. 11/707,053.

International Search Report for PCT/US2009/59374 dated Dec. 3, 2009.

Sutlive, et al., Contractile Properties of the Tongue's Genioglossus Muscle and Motor Units in the Rat, Genioglossus Muscle Properties, Muscle & Nerve, Mar. 2000 pp. 416-425.

\* cited by examiner

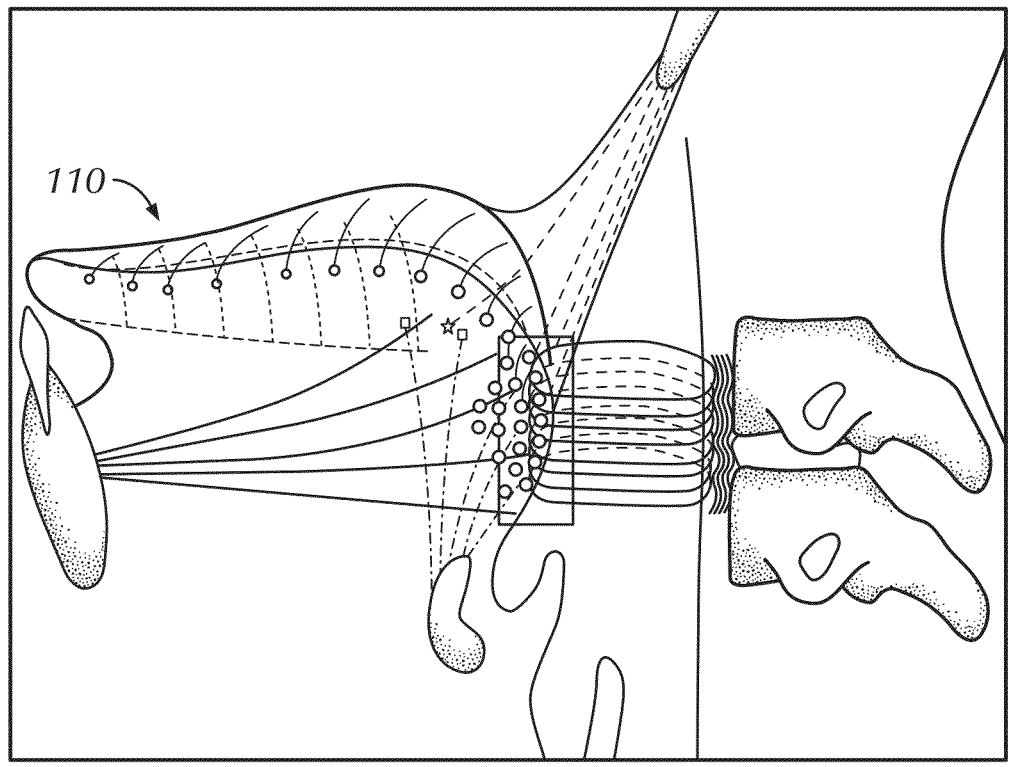
FIG. 1
*(Prior Art)*
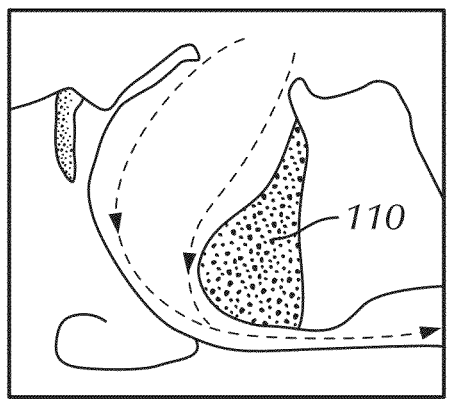 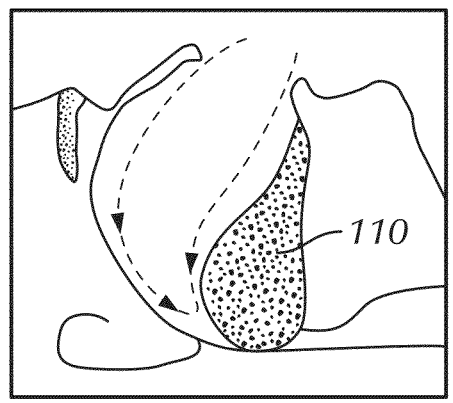
FIG. 2A
*(Prior Art)*
FIG. 2B
*(Prior Art)*

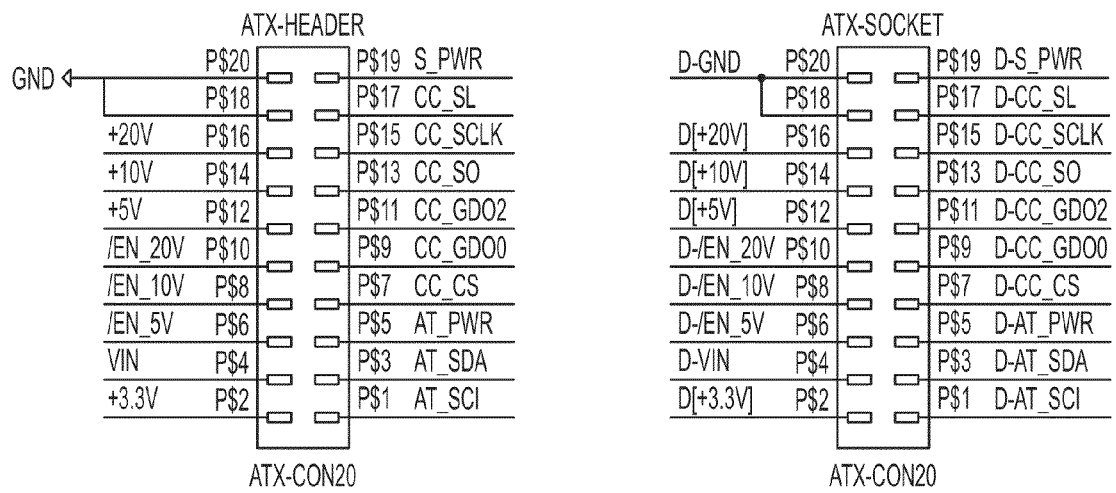
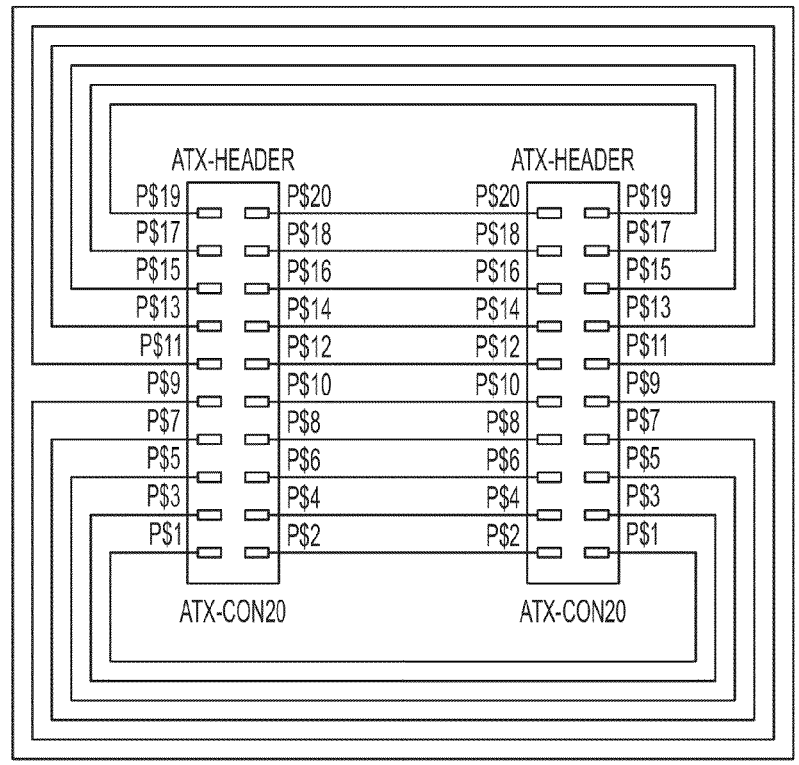
*FIG. 21*

FIG. 30

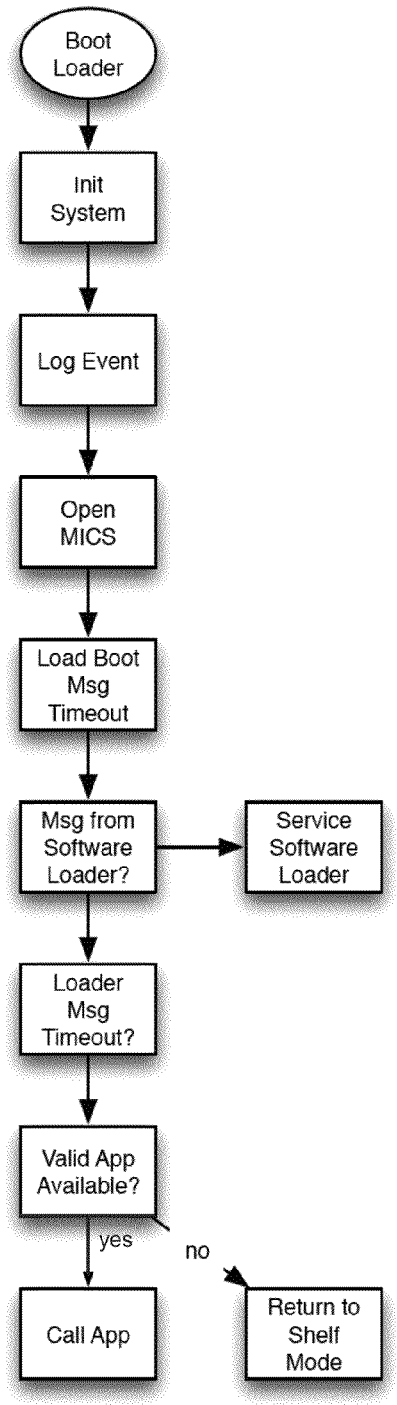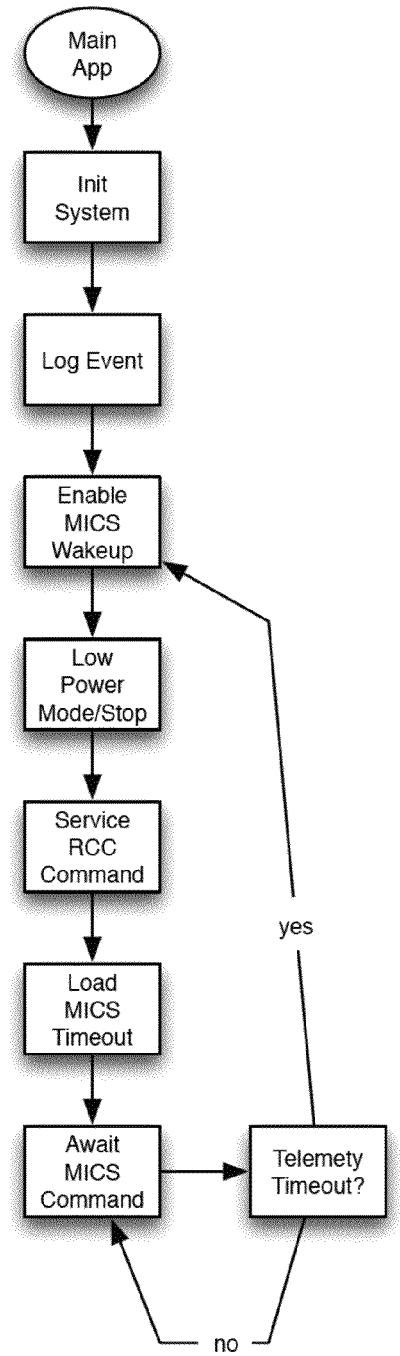
*FIG. 50*                              *FIG. 51*

SYSTEM FOR STIMULATING A HYPOGLOSSAL NERVE FOR CONTROLLING THE POSITION OF A PATIENT'S TONGUE

CROSS-REFERENCE TO RELATED APPLICATIONS

This application is a continuation of U.S. patent application Ser. No. 12/787,206 filed May 25, 2010 which claims the benefit of U.S. Provisional Patent Application No. 61/259,893 filed Nov. 10, 2009 entitled "System For Stimulating A Hypoglossal Nerve For Controlling The Position Of A Patient's Tongue", which are hereby incorporated by reference in their entirety.

BACKGROUND OF THE INVENTION

The present invention generally relates to a system for stimulating a Hypoglossal nerve for controlling the position of a patient's tongue. In one embodiment, the Hypoglossal nerve is stimulated to prevent obstructive sleep apnea.

Sleep apnea is a sleep disorder characterized by pauses in breathing during sleep. Those affected by sleep apnea stop breathing during sleep numerous times during the night. There are two types of sleep apnea, generally described in medical literature as central and obstructive sleep apnea. Central sleep apnea is a failure of the nervous system to produce proper signals for excitation of the muscles involved with respiration. Obstructive sleep apnea (OSA) is caused by episodes of physical obstruction of the upper airway channel (UAW) during sleep. The physical obstruction is often caused by changes in the position of the tongue 110 during sleep that results in the closure of the soft tissues at the rear of the throat or pharynx (See FIGS. 1, 2A and 2B).

OSA is characterized by the complete obstruction of the airway causing breathing to cease completely (Apnea) or partially (Hypopnea). The human airway (at the level of the thorax) is lined by soft tissue, any collapse of its walls results in the closure of the airway which leads to insufficient oxygen intake, thereby interrupting one's sleep (episodes or microarousals).

During sleep, the tongue muscles relax. In this relaxed state, the tongue may lack sufficient muscle tone to prevent the tongue from changing its normal tonic shape and position. When the base of the tongue and soft tissue of the upper airway collapse, the upper airway channel is blocked, causing an apnea event (FIG. 2B). Blockage of the upper airway prevents air from flowing into the lungs, creating a decrease in blood oxygen level, which in turn increases blood pressure and heart dilation. This causes a reflexive forced opening of the upper airway channel until normal patency is regained, followed by normal respiration until the next apneaic event. These reflexive forced openings briefly arouse the patient from sleep.

OSA is a potentially life-threatening disease that often goes undiagnosed in most patients affected by sleep apnea. The severity of sleep apnea is determined by dividing the number of episodes of apneas and hypopneas lasting ten seconds or more by the number of hours of sleep. The resulting number is called the Apnea-Hypopnea Index, or AHI. The higher the index the more serious the condition. An index between 5 and 10 is low, between 10 and 15 is mild to moderate, over 15 is moderately severe, and anything over 30 indicates severe sleep apnea.

Current treatment options range from drug intervention, non-invasive approaches, to more invasive surgical procedures. In many of these instances, patient acceptance and therapy compliance is well below desired levels, rendering the current solutions ineffective as a long-term solution.

Current treatment options for OSA have not been consistently effective for all patients. A standard method for treating OSA is Continuous Positive Airway Pressure (CPAP) treatment, which requires the patient to wear a mask through which air is blown into the nostrils and mouth to keep the airway open. Patient compliance is poor due to discomfort and side effects such as sneezing, nasal discharge, dryness, skin irritation, claustrophobia, and panic attacks. A surgical procedure where rigid inserts are implanted in the soft palate to provide structural support is a more invasive treatment for mild to moderate cases of OSA. Alternate treatments are even more invasive and drastic, including uvulopalatopharyngoplasty and tracheostomy. However, surgical or mechanical methods tend to be invasive or uncomfortable, are not always effective, and many are not tolerated by the patient.

Nerve stimulation to control the position of the tongue is a promising alternative to these forms of treatment. For example, pharyngeal dilation via Hypoglossal nerve (XII) (FIG. 3) stimulation has been shown to be an effective treatment method for OSA. The nerves are stimulated using an implanted electrode to move the tongue and open the airway during sleep. In particular, the medial XII nerve branch (i.e., in. Genioglossus), has demonstrated significant reductions in UAW airflow resistance (i.e., increased pharyngeal caliber). While electrical stimulation of nerves has been experimentally shown to remove or ameliorate certain conditions (e.g., obstructions in the UAW), current implementation methods typically require accurate detection of a condition (e.g., a muscular obstruction of the airway or chest wall expansion), selective stimulation of a muscle or nerve, and a coupling of the detection and stimulation. These systems rely on detection of breathing and/or detection of apnea events as preconditions to control and deliver electrical stimulation in order to cause only useful tongue motions and to periodically rest the tongue muscles and avoid fatigue. In one system, for example, a voltage controlled waveform source is multiplexed to two cuff electrode contacts. A bio-signal amplifier connected to the contacts controls stimulus based on breathing patterns. In another system, a microstimulator uses an implanted single-contact constant current stimulator synchronized to breathing to maintain an open airway. A third system uses an implantable pulse generator (IPG) with a single cuff electrode attached to the distal portion of the Hypoglossal nerve, with stimulation timed to breathing. This last system uses a lead attached to the chest wall to sense breathing motions by looking at "bio-impedance" of the chest wall. Still another system monitors vagus nerve electroneurograms to detect an apnea event and stimulate the Hypoglossal nerve in response.

What is needed is a system and method of electrical stimulation of the Hypoglossal nerve for controlling tongue position that is not tied to the detection of breathing and/or an apnea event.

BRIEF SUMMARY OF THE INVENTION

A system for stimulating a Hypoglossal nerve for controlling the position of a patient's tongue according to some embodiments of the present invention includes an electrode configured to apply one of at least one electric signal to one of at least one targeted motor efferent located within a Hypoglossal nerve to stimulate at least one muscle of the tongue.

In a further embodiment, the system further includes an implantable pulse generator (IPG) coupled to the electrode. In a further embodiment the system includes a remote control and charger coupled to the IPG. In one embodiment the remote control powers the IPG. In a further embodiment, the remote control re-charges the IPG. In a further embodiment, the system includes a docking station configured to charge the remote control and charger. In one embodiment, the remote control and charger are configured to couple with a computer to program the IPG. In a further embodiment, the system includes a sensor configured to measure the temperature of the IPG. In one embodiment, the electrode includes a plurality of contacts. In one embodiment, the IPG is programmable to assign the contacts to one of a plurality of functional groups. In one embodiment, the IPG is programmable to sequence or interleave the functional groups. In one embodiment, each functional group maintains an open airway in the patient and a first functional group includes at least one or more different muscles than a second functional group. In one embodiment, the electrode includes six contacts. In one embodiment, the contacts are each driven by their own independent current source.

In a further embodiment, the system includes a Medical Implant Communication Service (MICS) telemetry transceiver. In a further embodiment, the system includes an inductive link telemetry transceiver. In a further embodiment, the system includes a primary boot loader. In a further embodiment, the system includes a secondary boot loader. In one embodiment, the electrode includes a cuff housing configured to wrap around a portion of the Hypoglossal nerve. In one embodiment, the electric signal is applied to the Hypoglossal nerve via an open loop system. In one embodiment, the electrode is driven by multiple current sources. In a further embodiment, the system includes event logging memory. In a further embodiment, the system includes a multiplexer configured to measure impedance of at least one of the electrode contacts and patient tissue. In one embodiment, the IPG is covered by a hermetic enclosure.

BRIEF DESCRIPTION OF THE SEVERAL VIEWS OF THE DRAWINGS

The foregoing summary, as well as the following detailed description of exemplary embodiments of a system for stimulating a Hypoglossal nerve for controlling a position of a patient's tongue, will be better understood when read in conjunction with the appended drawings. It should be understood, however, that the invention is not limited to the precise arrangements and instrumentalities shown.

In the drawings:

FIG. 1 is an illustration of the human airway;

FIG. 2A is an illustration of an open human airway;

FIG. 2B is an illustration of a closed human airway during an apnea event;

FIG. 21 is a schematic diagram of the IPG board to board connections and Manufacturing Test Adapter;

FIG. 30 is a depiction of the aura Clinical Manager (aCM) Patient Manager Screen;

FIG. 50 is a flow diagram for the secondary Boot Loader Process;

FIG. 51 is a flow diagram for the IPG Main Application Process;

DETAILED DESCRIPTION OF THE INVENTION

Figure 3:
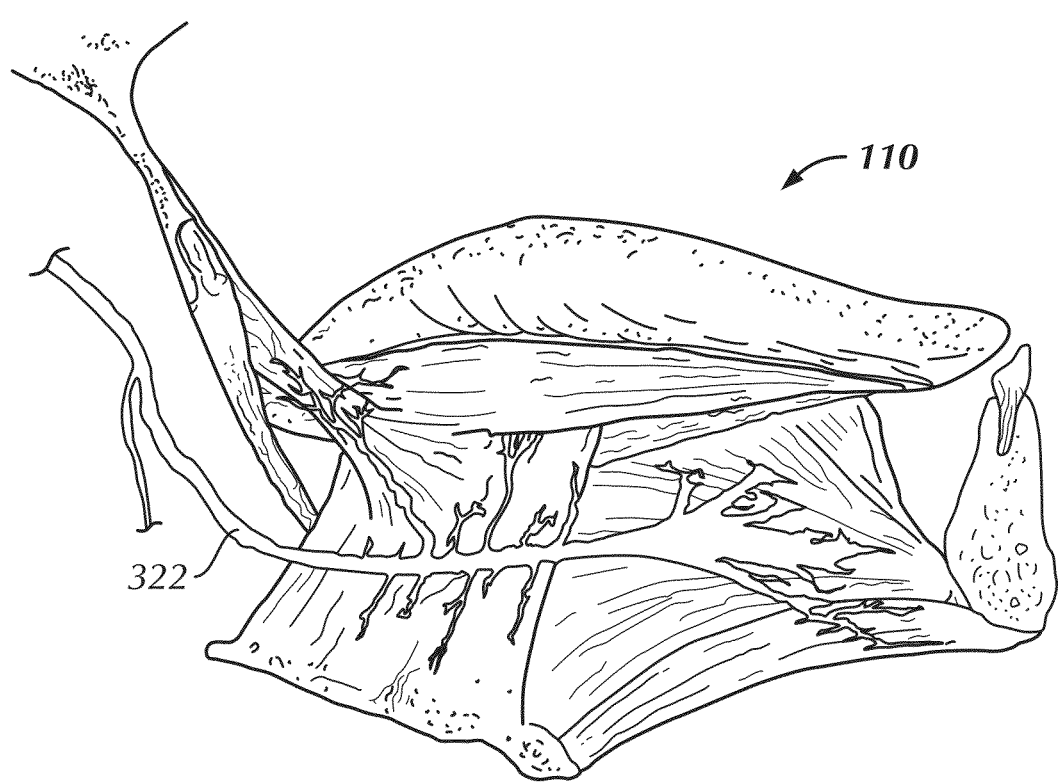
FIG. 3 is an illustration of the human tongue.

Similar to the embodiments described in U.S. patent application Ser. No. 12/572,758, which is hereby incorporated by reference in its entirety, the system described herein operates in an open-loop continuous fashion to stimulate the hypoglossal nerve (HGN) of a patient suffering from OSA. Referring to FIG. 3, the Hypoglossal Nerve (HGN) 322 is primarily a motor nerve and activates the various extrinsic and intrinsic muscles of the tongue. The tongue 110 has been described as a hydrostat, a muscle that is constrained within a relatively fixed volume, without the benefit of generating forces between two bony surfaces. Much like the trunk of an elephant, the tongue is able to change its shape by the contraction of its various muscle elements to protrude and retrude the tongue, curl, flatten, move up or down within the oral-pharyngeal cavity to assist with breathing, speech, mastication and swallowing.

The tongue muscle is different from other muscles in the body in that it has been demonstrated to have unique fatigue resistant properties. The tongue can be artificially activated by electrical stimulation for long periods of time without the typical position or force degradation that is accompanied with skeletal muscle when it is electrically stimulated. Like the heart, gastro-intestinal, and a few other specialized muscles within the human body, the tongue muscles have properties that make them particularly attractive for nearly constant activation, and thus the HGN 322 is amenable to the methods described here to maintain muscle tone and hence position and shape during sleep that are normally present during wakeful hours for the patient but are absent during the deepest levels of sleep.

Figure 11:
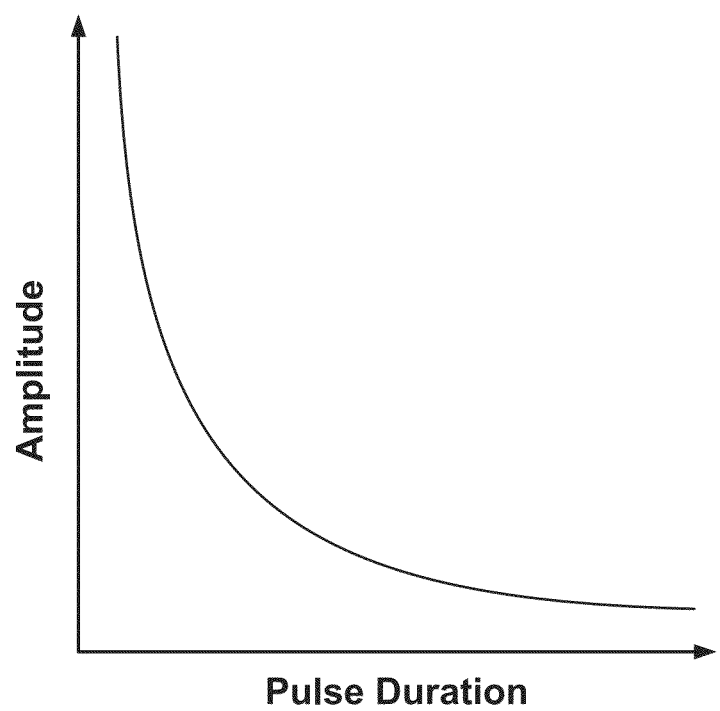
FIG. 11 is an exemplary strength-duration curve.

As is known in the art, excitation of a nerve fiber can occur along a strength duration iso-threshold curve, a nerve fiber will be excited as long as the amplitude is above the curve or the phase duration is to the right of the curve. An exemplary strength curve is shown in FIG. 11. At either end of the curve the shape of the curve is asymptotic; at a limiting phase duration no amount of stimulation current elicits a response, and at the other no phase duration is long enough to elicit a response either. The invention described herein may refer to the use of stimulus amplitude for means of modulating the recruitment of nerve fibers, but it shall be understood that many methods, including phase duration and stimulus amplitude, can be utilized to the same ends of activating nerve fibers with electrical stimulation.

Nerve fibers are preferentially activated, or recruited, in the order of their proximity to the electrode contact and by their fiber diameter. As a general rule, the closer a fiber is to the cathodic contact, the more likely it will be activated (the general form of a stimulating system is to place the cathodic contact in close proximity to the target nerve axons; other forms of stimulation exist and shall be obvious to those skilled in the art). The larger the diameter of a fiber, the more likely it will be activated. The distance and size distribution in a nerve bundle does not change appreciably over time. Hence, the recruitment properties—which fibers will be activated with a particular amplitude pulse—do not change either. If the applied stimulus is maintained at a sufficiently high enough frequency, the recruited muscle fibers activated by the stimulated nerve fibers eventually fatigue. Muscle force and/or position then changes towards the relaxed, inactivated condition. The stimulation of skeletal muscle for postural control or limb motion is often performed at frequencies that would normally be expected to cause fatigue in those muscles along with the loss of desired function if the stimulation were maintained continuously. Stimulation may be modulated by changing the stimulus amplitude, as described above, or by changing the phase duration of the pulse. Great care and tremendous effort are expended in avoidance of fatigue in skeletal muscle applications for fear of loss of desired functional effect, for example, for patients suffering from spinal cord injury or other neurological dysfunction.

Figure 4A:
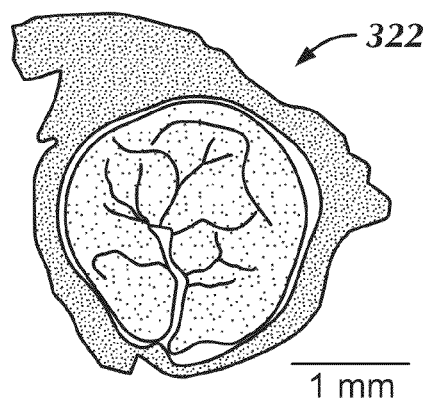
FIG. 4A is an illustration of a cross-section of a human Hypoglossal nerve.
Figure 4B:
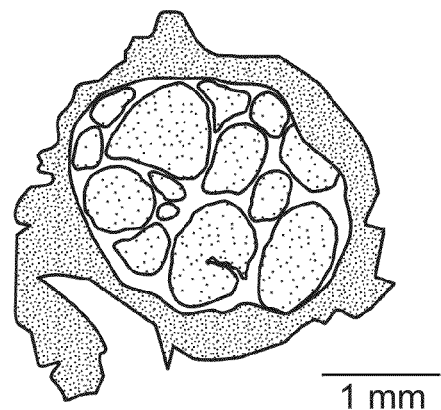
FIG. 4B is an illustration of a cross-section of a human Lingual nerve.
Figure 4C:
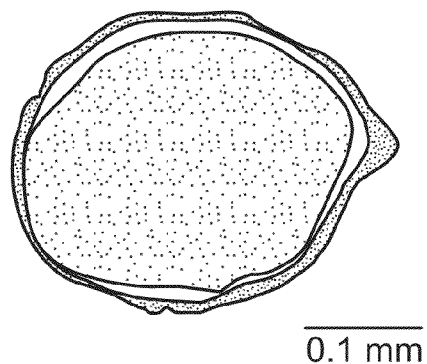
FIG. 4C is an illustration of a cross-section of a rat Hypoglossal nerve.
Figure 5:
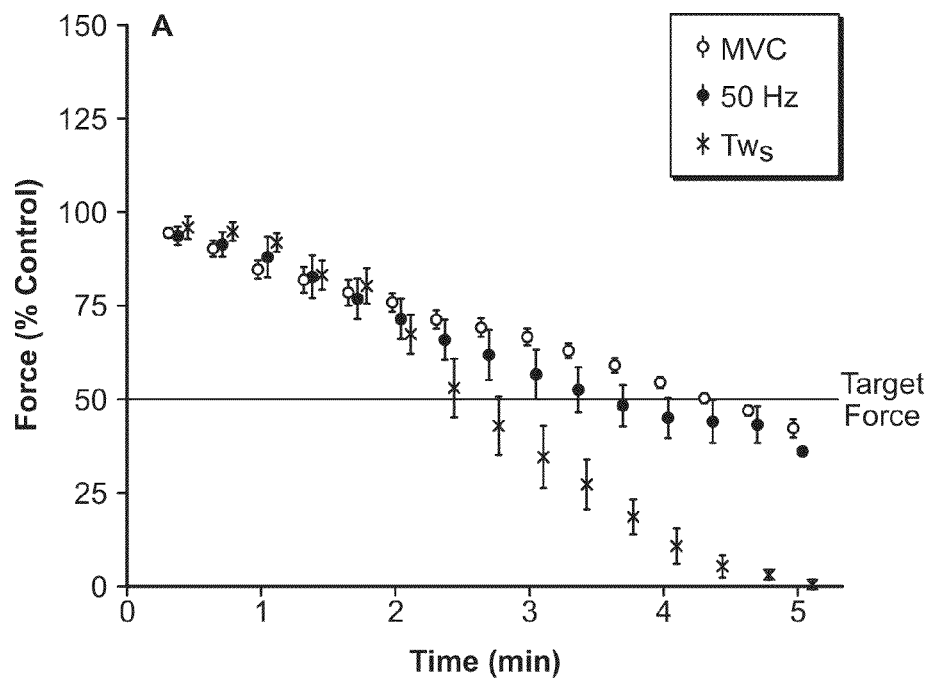
FIG. 5 is an exemplary set of fatigue curves of human quadriceps muscle showing maximum voluntary contraction, 50 Hz electrical stimulation and twitch responses.
Figure 6:
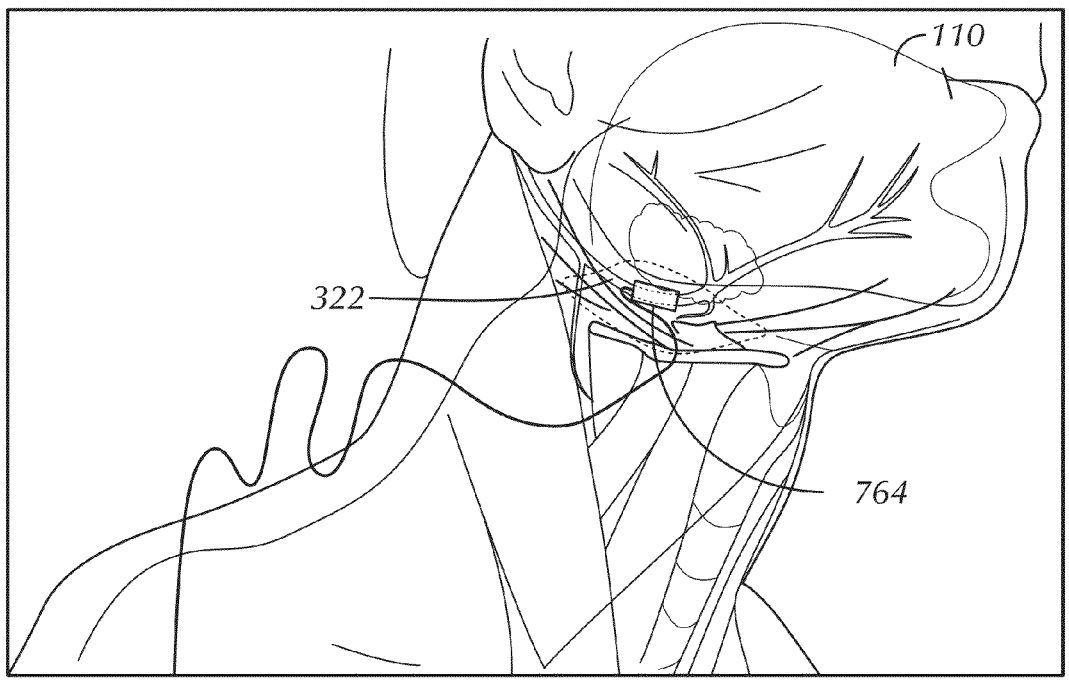
FIG. 6 is an exemplary illustration of an electrode attached to a patient's Hypoglossal nerve.

Peripheral nerves such as the HGN 322 are organized often by grouping fibers that go to each of the branches at the distal end of the nerve into fascicles, or tubules within the main nerve bundle. Cross sections views of such peripheral nerves clearly show this organization as separate regions of nerve fibers. Stimulation electrodes placed closed to these bundles or fascicles preferentially activate the fibers going to the down-stream muscle groups. FIGS. 4A, 4B and 4C demonstrate the organization structure of the Human Hypoglossal nerve 322 (FIG. 4A) and the Human Lingual Nerve (FIG. 4B), as well as the Rat Hypoglossal Nerve (FIG. 4C). The Hypoglossal nerves in both Human and Rat are afascicular, lacking the clear organizational structure present in most peripheral nerves, and which is present in the Human Lingual Nerve, as described in U.S. patent application Ser. No. 12/572,758, hereby incorporated by reference in its entirety. Nonetheless, it is organized and electrodes placed around the circumference can be used to target specific nerve fibers and hence muscle groups to affect only desirable muscle functions, movements, and motions.

Fatigue may be minimized or prevented by using a stimulation duty cycle—that is, stimulating for a certain amount of time before significant fatigue sets in, then stopping to let the muscle rest and regain its ability to contract. For obstructive sleep apnea this is less than optimal because without an applied stimulus during the off period of the electrical stimulation duty cycle the tongue would not be driven to maintain a desired position, and could fall back against the rear of the throat and allow an apnea event to occur. This is one of the reasons that many OSA stimulation systems rely on sensors to detect when to apply stimulation and when to leave it off. The method of using duty cycle to rhythmically apply stimulation has been proposed, also, to do away with the need to sense breathing events, in the hopes that by introducing rhythmic stimulation to the Hypoglossal nerve that somehow the breathing events would synchronize automatically to the stimulation timing. This has not been proven and studies, which used microstimulators in sheep, demonstrated that manual timing of stimulation to the events of breathing was required to achieve a useful outcome in single point stimulation of the Hypoglossal nerve.

Figure 7:
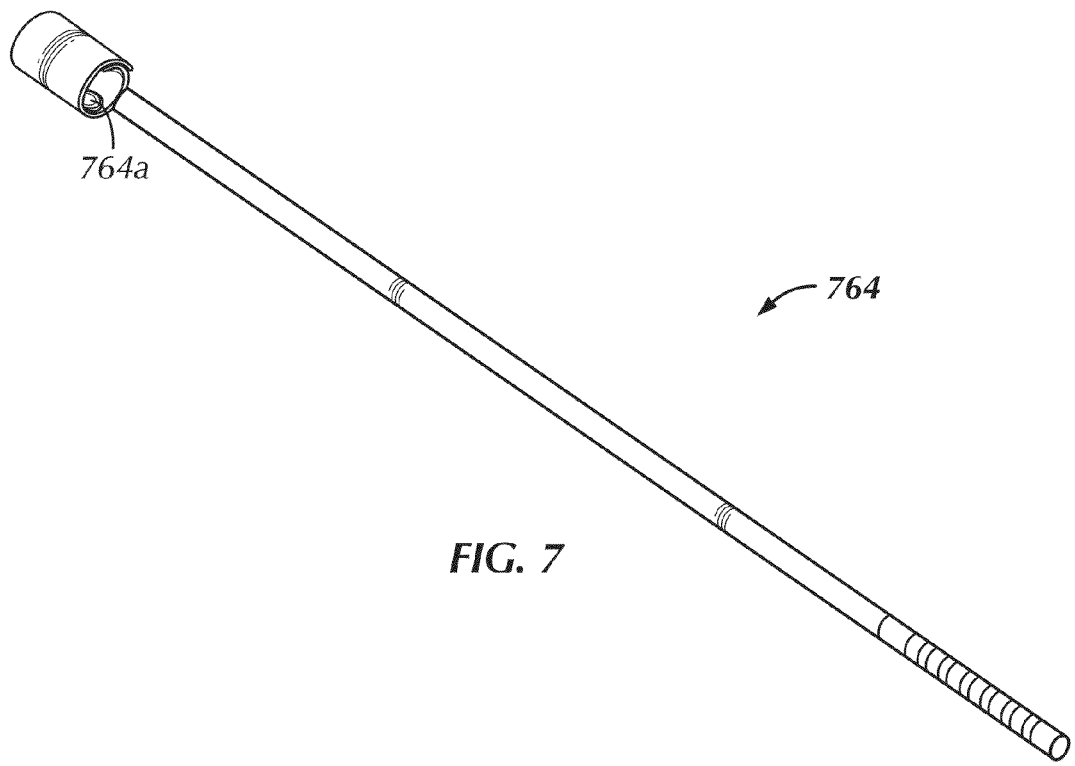
FIG. 7 is a perspective view of the electrode.
Figure 8:
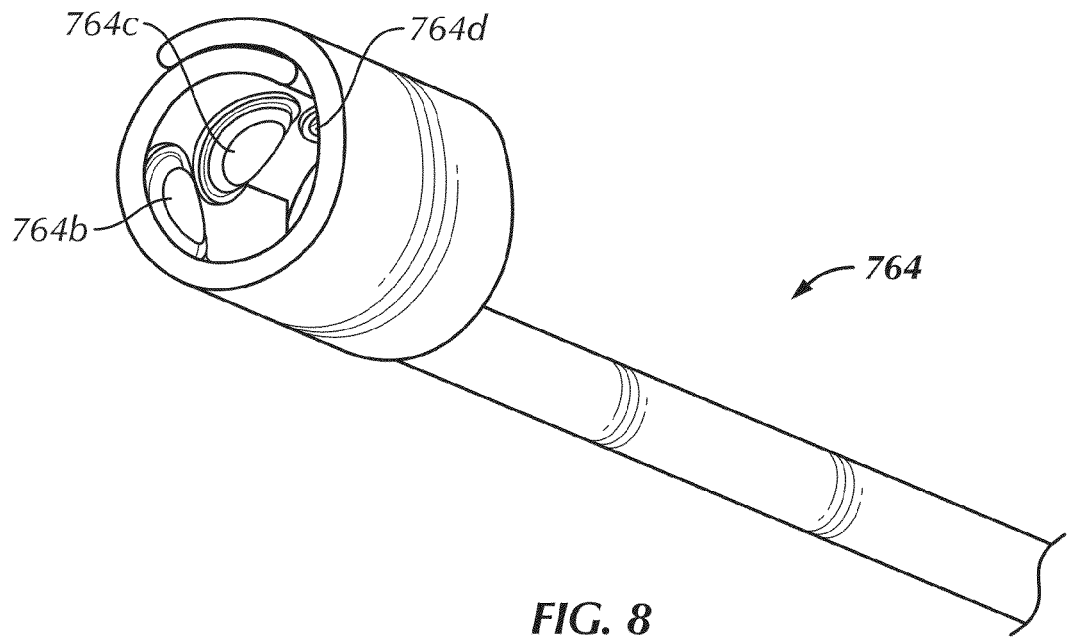
FIG. 8 is a perspective view of the electrode showing the plurality of contacts.

Another method of minimizing or preventing muscle fatigue is to use one or more independent current sources to activate multiple portions of the desired muscle groups. In certain exemplary embodiments, one or more independent current sources drive one or more contacts (764a, 764b, 764c and 764d for example shown in FIGS. 7 and 8) that interface with the Hypoglossal nerve 322. These contacts are optionally contained in a single cuff electrode 764 as shown in FIGS. 7 and 8. Each contact can be activated separately or in combination with other contacts as discussed further below.

Figure 9:
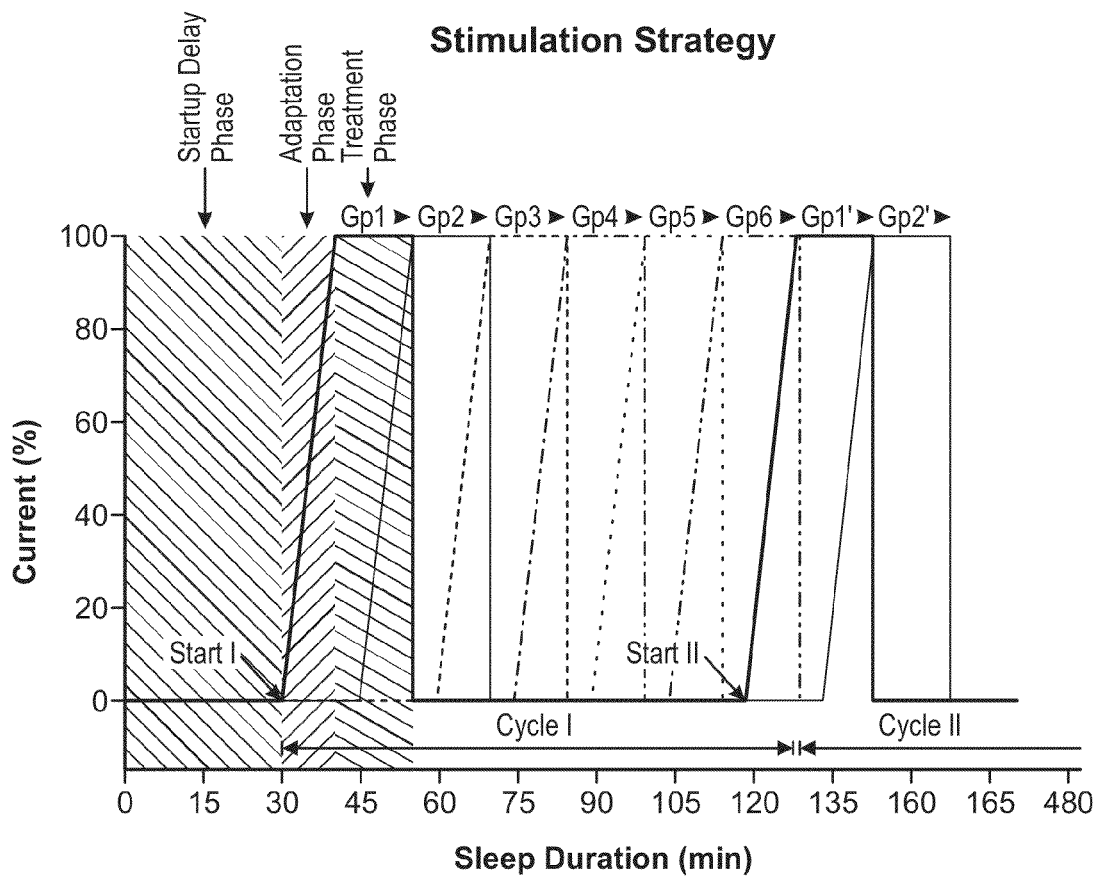
FIG. 9 is a graphical representation of an exemplary stimulation strategy.

In certain embodiments, each contact is assigned to one or more functional or muscle groups. Functional groups may in turn be used to select regions of fibers within the nerve bundle that result in a desired tongue movement. The effort of moving the tongue to the desired position is thus shifted from one functional group to another functional group so that no single functional group is required to work all of the time. Thus, the effort of moving the tongue is shared among multiple stimulated nerve fibers and their associated muscles, preventing or reducing fatigue because none of the groups are activated long enough to cause significant fatigue, and during their off, or non-stimulated, state they are allowed to recover from the stimulation. In certain exemplary embodiments, each group is active until just before significant fatigue sets in. One or more additional groups are then activated to take its place, allowing the former muscle group fibers to rest. In one embodiment, the stimulation is spread over more than one contact wherein the duty cycle of each contact is overlapped (FIG. 9).

Figure 52:
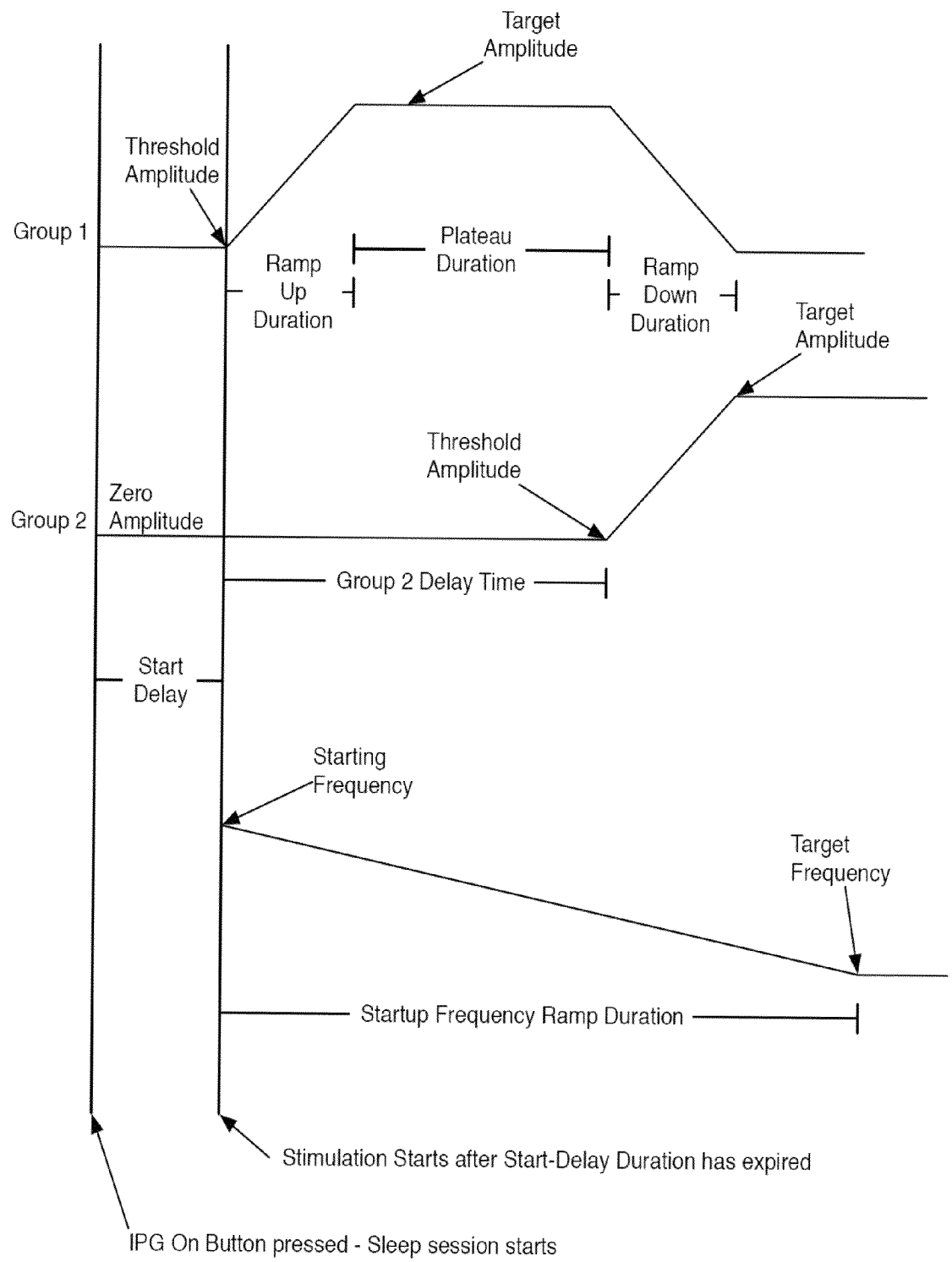
FIG. 52 is an exemplary representation of a stimulation strategy with two active groups.

A more detailed depiction of this transfer of muscle work load from one group to the next is depicted in FIG. 52. The course of events that occurs from the time that the patient starts a sleep session through the first group stimulation cycle and the beginning of the next is shown. After the initiation of a sleep session, a delay occurs allowing the patient to fall asleep. After the delay, the first group begins to stimulate, using its threshold amplitude, slowly ramping up for the duration of the ramp, until at the conclusion of the ramp and the beginning of the plateau phase the stimulation current amplitude has reached its target level. This ramp may help to prevent the patient from being aroused from sleep by the sudden start of stimulation at the target level. At the time that the ramp up began, the delay to the next group start was started as well, to allow the coordination from one group to another. After the plateau duration is complete for the first group, the stimulation begins to ramp back down to threshold for the ramp down duration. At the conclusion of the ramp down duration, the group is deactivated and the second group should already have begun its stimulation cycle. At the conclusion of the next group delay, the next group begins its stimulation cycle and the group after that begins its delay. All the while that stimulation is being ramped in the first and even perhaps in the second groups, frequency is being ramped down from a starting frequency to a target frequency after which the frequency remains at the target level until the end of the sleep therapy. This allows the smooth transition from one stimulation group to the next, and by ramping frequency downwards to the target frequency provides additional opportunity to prevent arousal and promote the comfort of the stimulation sensation to the patient.

Figure 10A:
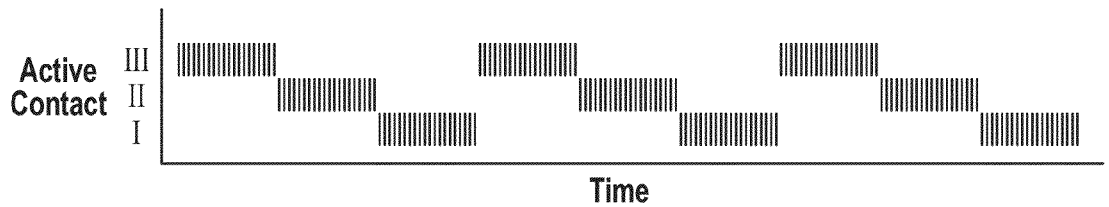
FIG. 10A is a graphical representation of an exemplary duty cycle stimulation strategy.
Figure 10B:
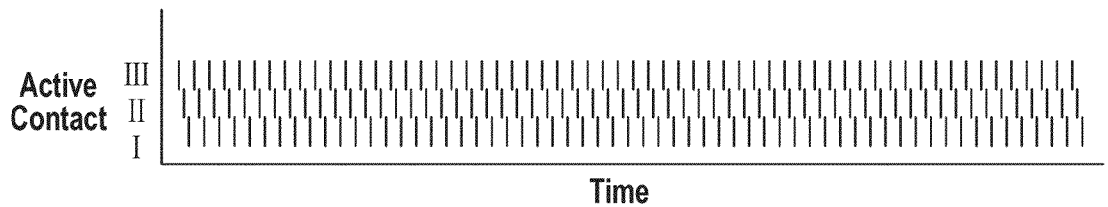
FIG. 10B is a graphical representation of an exemplary interleaved stimulation strategy.
Figure 10C:
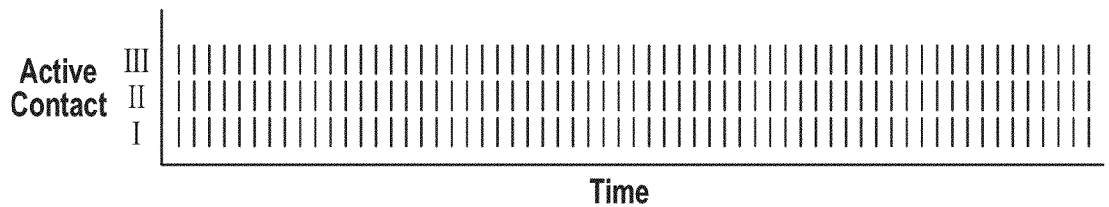
FIG. 10C is a graphical representation of an exemplary synchronous stimulation strategy.
Figure 10D:
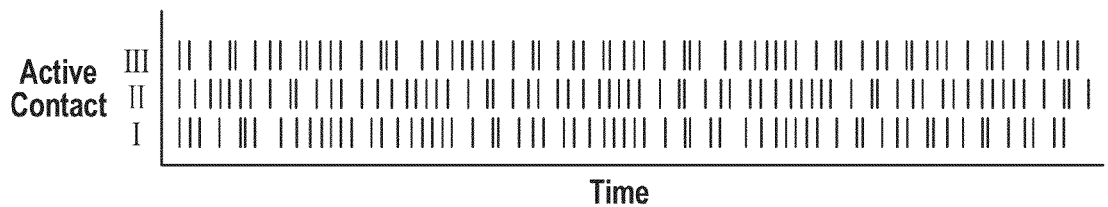
FIG. 10D is a graphical representation of an exemplary asynchronous or random stimulation strategy.

In one embodiment, the stimulation pulses may be generally random or pseudo random so long as the overall contractions per unit of time is limited (see FIG. 10D).

Another method of reducing or eliminating fatigue is to lower the stimulation frequency. The faster a nerve is stimulated, the faster it fatigues. Each pulse produces a contraction, with each contraction requiring a certain amount of work. The more contractions there are, the more the muscle works, and the more likely the muscle will become fatigued. Reducing the stimulation frequency to a rate just fast enough to achieve the desired response minimizes the rate at which muscle contractions occur. This minimizes the amount of work done by the muscle, delaying or minimizing muscle fatigue. In one embodiment, the stimulation is spread over more than one contact wherein each contact delivers a generally equal fraction of stimulation frequency that is out of phase with the other contacts (FIG. 10B). This method reduces the stimulation rate for each of the independent groups but results in a functional stimulation rate that is essentially the sum of the rates that are active. As shown in FIGS. 10A and 10B, the same effective force or position is maintained, but in FIG. 10A fatigue is prevented by duty cycle method and in FIG. 10B it is prevented by three groups running at one third the frequency of any one group in FIG. 10A resulting in the same muscle force or position and the same prevention of fatigue. Stimulation frequencies that have been used for activating skeletal muscle have often required the use of a frequency that results in tetanus, a smooth fusion of pulses fast enough to maintain a near continuous level of force or position. Tetanus is not required, per se, in the artificial activation of the tongue—the patient is asleep, and the cosmetic appearance of the tongue while it is activated is not nearly as important as the maintenance of airway patency. Experimental evidence has shown that stimulating at frequencies below 5 pulses per second have been adequate to maintain airway patency in patients with severe OSA.

Continuous or near continuous stimulation of a muscle is discouraged in the art because of fatigue problems. However, in view of the teaching herein, the tongue 110 is a fatigue resistant muscle. Testing in both rats and humans has confirmed this finding. In limited animal studies, it was demonstrated that rat tongue muscle could be stimulated at very high frequencies for extended periods without observable changes in tongue position. In one study, rather than stimulating at 15 pulses per second (pps), a frequency adequate to move the tongue sufficiently to clear the rear of the throat, stimulation was applied at supra-threshold levels at a frequency of 100 pps. The resulting tongue response was maintained for more than one hour before any significant change in tongue position could be detected. If the stimulation frequency were dropped to 15 pps, it is likely that stimulation may be applied more than five times longer before tongue position change would be expected to occur. In human trials, embodiments disclosed herein successfully stimulated patients with a fixed set of electrode contacts for many hours before the anti-apnea effect was seen to diminish. In one embodiment, using lower frequencies and multiple contacts on a human tongue increases the duration that stimulation could be applied before anti-apnea effects diminish.

Thus, with the tongue and associated rear throat tissues consistently driven in such a manner as to clear the airway there is no need to detect apneas because they simply will not be allowed to occur. Rather than timing stimulation to breathing, or monitoring for an apnea event prior to initiating treatment, the exemplary embodiments stimulate the Hypoglossal nerve in a predetermined manner via an open loop system to activate targeted muscles in the tongue to maintain airway patency. With airway resistance decreased and/or the tongue prevented from falling back against the rear of the throat, and/or pharyngeal compliance reduced, there is no need to monitor for apneas, because they are prevented from occurring, nor monitor for ventilation timing because the stimulation is not timed or synchronized to breathing at all, it is maintained continuously during the entire sleeping period.

The activation of a protrusor that moves the tongue forward and away from the oral-pharyngeal junction, or the activation of a retrusor that acts to decrease the compliance of the pharyngeal wall are both desirable in preventing the occlusion of the airway. Co-activation of agonistic and antagonistic muscles has been shown in the literature to increase stiffness and to maintain position of a joint or body segment, likewise, co-activation of protrusors and retrusors of the tongue should have the effect of maintaining position and stiffness of the tongue and pharanygeal walls to a desirable effect. The activation of intrinsic muscles that change the shape of the tongue may also lead to desirable motions even though the actions of these muscles may not be clearly defined in terms of protrusor or retrusor. It shall be understood that the activation of any tongue muscle that achieves beneficial motions or actions of the tongue musculature is a potential target of the selective targeted methods of electrical stimulation as described by the methods of this patent and it shall not be the single object of the described method to only activate protrusors per se.

Since the tongue is a fatigue-resistant muscle, it can be stimulated, using the techniques described herein, for long durations without loss of force or movement. By stimulating the Hypoglossal nerve, tongue activation resembling normal daytime tongue muscle tone is restored to key muscles during sleep. The tongue does not fall into the throat, keeping the airway open and allowing the patient to breathe normally during sleep. Continuous or near-continuous stimulation maintains the tongue in a desired position, shaping the airway, without the necessity of a complicated closed loop stimulation strategy with the associated dependence upon sensors and their interpretation. While the tongue musculature is fatigue resistant, it is still susceptible to fatigue in general. Therefore methods employed herein are still directed at maintaining therapeutic effect by utilization of multiple groups to maintain desired function and other methods such as frequency control to minimize the work load of any single muscle group.

Neurostimulation is often performed on peripheral motor nerves. Peripheral motor nerves emanate from the ventral horns of the spinal cord and travel in bundles to various muscle groups. A single motor nerve bundle may contain many sub-groups of neurons. Some neuron sub-groups are organized into separate sub-bundles called fascicles, which are easily viewed in histological cross section, and often connect to groups of muscle fibers within the same muscle. With these sub-groups, stimulation of the sub-group typically results in activation of a group of muscles working together to achieve a desired effect.

Other peripheral nerves, such as the Hypoglossal nerve, have sub-bundles that are not organized into fascicles. Instead, these sub-bundles run in somewhat controlled but less well defined regions of the nerve, and are not easily recognizable in a cross-sectional view. These sub-groups often go to multiple muscle groups in different locations. An example of such a nerve is the Hypoglossal nerve, which has multiple sub-groups connecting to different portions of the tongue. A more detailed description of the nerve structure for the human tongue is disclosed in U.S. Patent Application No. 61/136,102, filed Oct. 9, 2008, hereby incorporated by reference in its entirety.

Not every muscle of the human tongue is involved in the opening of the airway. Some stimulated muscles act to block the airway. In the embodiments described, the only nerves targeted by the targeted selective electrical stimulation method described herein are nerves that stimulate muscles that activate the tongue resulting in the optimal opening of the airway and suppression of unwanted tongue movements. In contrast, whole nerve stimulation activates the entire nerve contents and nerve bundles containing nerve fibers to both desirable and non-desirable groups of contracting muscles are simultaneously activated. This not only leads to suboptimal levels of opening, but may also produce undesirable tongue motions. A surgical way to avoid this problem with less than optimal stimulation methods is to place stimulating electrodes on distal branches of the nerve that only innervate the desired muscle groups, a task that is difficult and potentially hazardous to the nerve.

In these cases, activation of the entire bundle from an artificial electrical stimulus results in activation of all of the muscles activated by the sub-groups within the stimulated nerve group. In the present invention, to target only the desired specific groups of fibers within a nerve bundle, exemplary embodiments use multiple nerve electrode contacts and multiple independent controlled current sources to activate only the desired sub-groups. This minimizes or eliminates the likelihood of delivering stimulation to muscles not providing the desired tongue position.

The Hypoglossal nerve in the region just below the sub-mandibular gland (proximal to the Styloglossus/Hyoglossus branches and distal to the ansa cervicalis branch) is non-fascicular, that is, the various nerve groups that separate distally are not isolated in the bundle as fascicles, but are present en masse with all of the fibers of the Hypoglossal nerve. As described in the rat dye studies discussed in U.S. patent application Ser. No. 12/572,758, and in studies on human cadavers, there appears, however, to be an organization to the bundle, with fibers mostly innervating the Genioglossus muscle residing in the medial region of the bundle. Studies conducted in rats, an animal model identified thus far that replicates the non-fascicular nature of the human Hypoglossal nerve, revealed an organization of the whole nerve, suggesting that targeted activation of a sub-population of neurons in the Hypoglossal nerve would be possible. Stimulation studies in rats and humans with multipolar electrodes and multiple independent current sources verified this with the result that multiple distinct motions and positions of the tongue could be achieved using targeted stimulation methods and devices. Placement of electrode contacts about the perimeter of the Hypoglossal nerve at this region has achieved targeted selective activation of the tongue muscles. The resulting airway changes elicited by stimulation depend upon which electrode contacts are activated.

In one exemplary system, an electrode 764 is implanted around the Hypoglossal nerve at or near an approximately 1 cm length of 2.5 to 4.5 mm diameter nerve bundles. This is typically at the rear of and below the mandible, just underneath the sub-mandibular gland, proximal to the Styloglossus/Hyoglossus branches and distal to the ansa cervicalis branch. At this point, the major branches to the various tongue muscles are distal to the electrode site.

Targeted Selective Stimulation of Hypoglossal Nerve Efferents

In one embodiment, the present invention is directed to the targeted selective stimulation of Hypoglossal nerve efferents in animals. In one embodiment, the present invention is directed to the targeted selective stimulation of Hypoglossal nerve efferents in mammals. In one embodiment, the present invention is directed to the targeted selective stimulation of Hypoglossal nerve efferents in rats. In one embodiment, the present invention is directed to the targeted selective stimulation of Hypoglossal nerve efferents in humans.

In one embodiment, the present invention is directed to the targeted selective stimulation of Hypoglossal nerve efferents via electric signals emitted from at least one programmable electrode contact. In one embodiment, the targeted selective stimulation of Hypoglossal nerve efferents occurs via multiple electrode contacts. In one embodiment, the targeted selective stimulation of Hypoglossal nerve efferents is driven by multiple current sources. In one embodiment, the multiple electrode contacts are each driven by their own independent current source.

In one embodiment, the multiple electrode contacts each activate a beneficial muscle group and alternate in their operation such that the beneficial function is maintained by at least one group at all times. In one embodiment, the multiple electrode contacts each activate a beneficial muscle group and interleave their operation such that the patency of the airway is maintained. In one embodiment, the multiple electrode contacts each activate a beneficial muscle, and alternate in their operation such that the patency of the airway is maintained. In one embodiment, the multiple electrode contacts each activate one of a beneficial muscle, and interleave their operation such that the patency of the airway is maintained.

In one embodiment, the method includes activating the ipsilateral Geniohyoid muscle. In one embodiment, the method includes activating rostral or caudal or both compartments of the ipsilateral Geniohyoid muscle. In one embodiment, the method includes activating at least one compartment or both compartments of ipsilateral or with the rostral compartment of the contralateral Geniohyoid muscles increasing the dilation (of the pharyngeal airway) and the patency of the airway channel.

In one embodiment, the modulating electric signals have a frequency sufficient for a smooth tetanic contraction. In one embodiment, the modulating electric signals have a stimulation frequency of about 10 to about 40 pps. In one embodiment, the modulating electric signals are of an intensity from about 10 to about 3000 microamps ($\mu A$). In one embodiment, the modulating electric signals have a stimulation pulse width of about 10 to about 1000 microseconds ($\mu s$).

In one embodiment, the targeted selective stimulation of Hypoglossal nerve efferents activates at least one lingual muscle. In one embodiment, the targeted selective stimulation of Hypoglossal nerve efferents activates at least one upper airway channel dilator muscle. In one embodiment, at least one protrusor muscle is activated. In one embodiment, at least one protrusor muscle and at least one retrusor muscle are alternately activated. In one embodiment, at least one protrusor muscle and at least one retrusor muscle are co-activated. In one embodiment, the at least one protrusor muscle 400 activated is the genioglossus muscle. In one embodiment, at least one beneficial muscle group is activated. In one embodiment, at least two beneficial muscle groups are activated.

Method of Treating a Neurological Disorder Including Obstructive Sleep Apnea

In one embodiment, the present invention is directed to a method of treating, controlling, or preventing a neurological disorder by attaching at least one programmable electrode to a patient's Hypoglossal nerve proper 322; and selectively applying electric signals to motor efferents located within the Hypoglossal nerve proper 322 through the programmable electrode 764 to selectively stimulate at least one muscle. In one embodiment, the electric signals are modulating. In one embodiment, the method of treating, controlling, or preventing a neurological disorder consists essentially of the recruitment of retrusor motor efferents. In one embodiment, the method comprises the recruitment of protrusor motor efferents. In one embodiment, the method comprises the recruitment of a ratio of retrusor to protrusor motor efferents such as the ratios described above to treat a neurological disorder.

In one embodiment, the neurological disorder suitable for treatment, control, or prevention by the present invention is selected from the group consisting of, but not limited to oral myofunctional disorders, atrophies, weakness, tremors, fasciculations, and myositis. In one embodiment, the neurological disorder is obstructive sleep apnea. Other potential applications of this method, in addition to treatment of obstructive sleep apnea, include, for example, supplemental nerve stimulation to keep the airway open for treatment of snoring, hypopnea, or countering motor activation of the tongue during a seizure. Other health problems related to the patency of a patient's airway may also be treated using methods provided by the present invention.

In one embodiment, the present invention provides a method of treating, controlling, or preventing obstructive sleep apnea including the steps of attaching at least one programmable electrode to a patient's Hypoglossal nerve proper 322; and selectively applying electric signals to motor efferents located within the patient's Hypoglossal nerve proper 322 through the programmable electrode 764 to selectively stimulate at least one muscle. In one embodiment, at least one programmable electrode 764 provides a continuous, low level electrical stimulation to specific motor efferents to maintain the stiffness of the upper airway channel throughout the respiratory cycle. In one embodiment, at least one programmable electrode provides intermittent electrical stimulation to specific motor efferents at controlled, predetermined intervals sufficiently close to achieve a constantly opened airway.

In one embodiment, the method of treating, controlling, or preventing obstructive sleep apnea includes selectively activating one or more muscles in the upper airway channel to effectively reduce the severity of obstructive sleep apnea and improve airway patency. In one embodiment, the method includes targeted selective stimulation of motor efferents that activate the geniohyoid muscle, causing anterosuperior movement of the hyoid bone to increase the patency of the upper airway channel. In one embodiment, the method includes targeted selective stimulation of functionally opposite muscles that also effectively stiffen the upper airway channel to reduce the risk of collapse.

In one embodiment, the method of treating, controlling, or preventing obstructive sleep apnea consists essentially of the recruitment of protrusor motor efferents. In one embodiment, the method includes activating at least one protrusor muscle. In one embodiment, the method includes targeted selective stimulation of protrusor motor efferents located within the Hypoglossal nerve proper 322 that activate the genioglossus muscle, causing protrusion of the tongue to increase the patency of the upper airway channel.

Elements of the System

In one embodiment, the OSA system is comprised of implanted and external elements which together act to provide continuous open loop targeted selective stimulation of the HGN 322. The implanted elements (i.e. the elements implanted into the patient) may include an Implantable Pulse Generator 1370 (IPG) (see FIGS. 13-16) and a cuff electrode 764 (see FIG. 7). The external elements may include a Remote Control and Charger 2272 (RCC) (see FIG. 22), a Charger Coil 5374 (CC) and cable 5374a, a Docking Station 5378 (DS) and a power supply for the patient, and a notebook computer 5376 and the aura Clinical Manager (aCM) clinician's software programming system. The IPG 1370 may be responsible for generating the pulses that activate the desired neurons within the HGN 322, and is implanted in the anterior chest region of the patient. The cuff electrode 764 may attach to the IPG 1370 via an inline connector, and runs from the chest location of the IPG 1370 to the sub-mandibular region where it is wrapped around the HGN 322. The IPG 1370 may contain a plurality, such as six, independent current sources, each capacitively coupled via feedthroughs in its enclosure to the inline connector. The inline connector may have six torroidal spring contacts which mate with ring contacts of the cuff electrode 764 proximal connector. Each ring contact of the cuff electrode 764 may be connected by a wire in the cuff electrode 764 assembly to a contact within the self-sizing cuff. Each contact may be shaped to match the curvature of the nerve bundle of the HGN 322, and the six contacts are located within the cuff so that six sectors of the nerve circumference are in intimate contact with the cuff contacts. The IPG 1370 may be directed by the RCC 2272 to start and stop a sleep therapy treatment session, to provide information on the status of the IPG 1370 and the cuff electrode 764, and is used in conjunction with the CC to replenish the energy within the IPG 1370 battery. The aCM may be used by a clinical engineer or clinician to program the OSA system for use in providing therapy to the patient.

Implanted Pulse Generator (IPG)

Figures 13, 14:
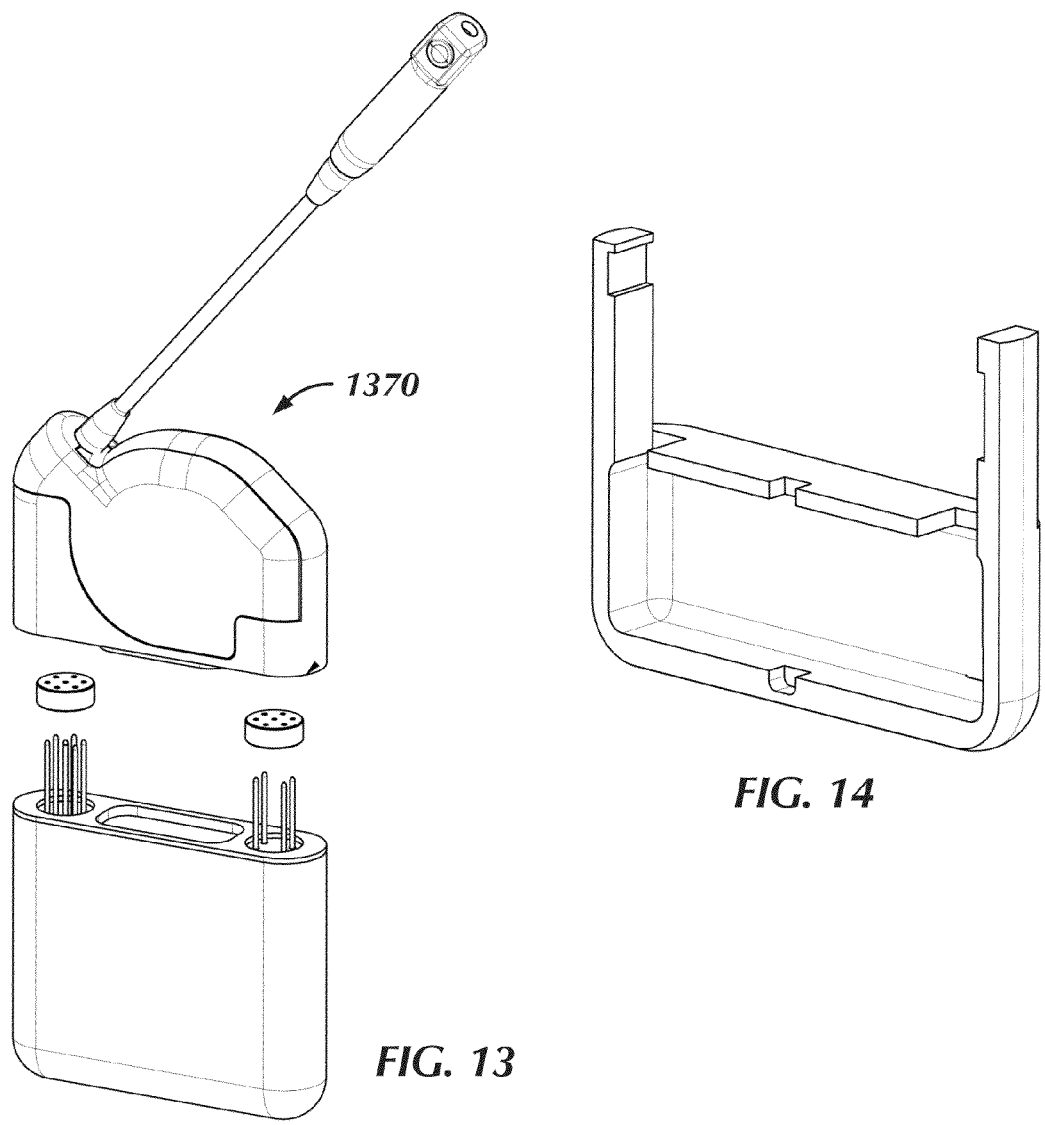
FIG. 13 is a partially exploded perspective view of the IPG with its header and inline connector attachment to the enclosure and feedthroughs.
FIG. 14 is a perspective view of the battery support for the IPG.
Figure 15:
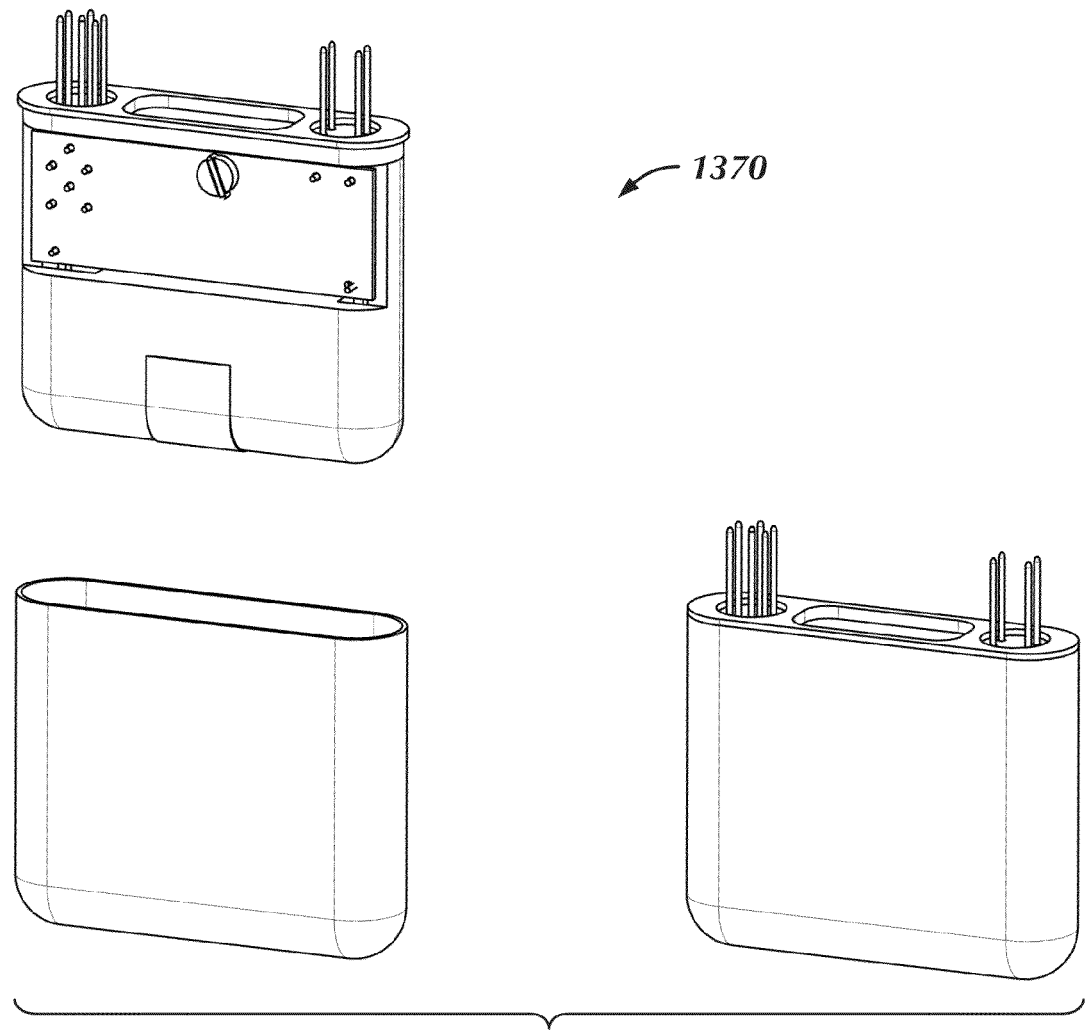
FIG. 15 is a partial perspective view of the IPG electronics assembly being inserted into its titanium enclosure.
Figure 16:
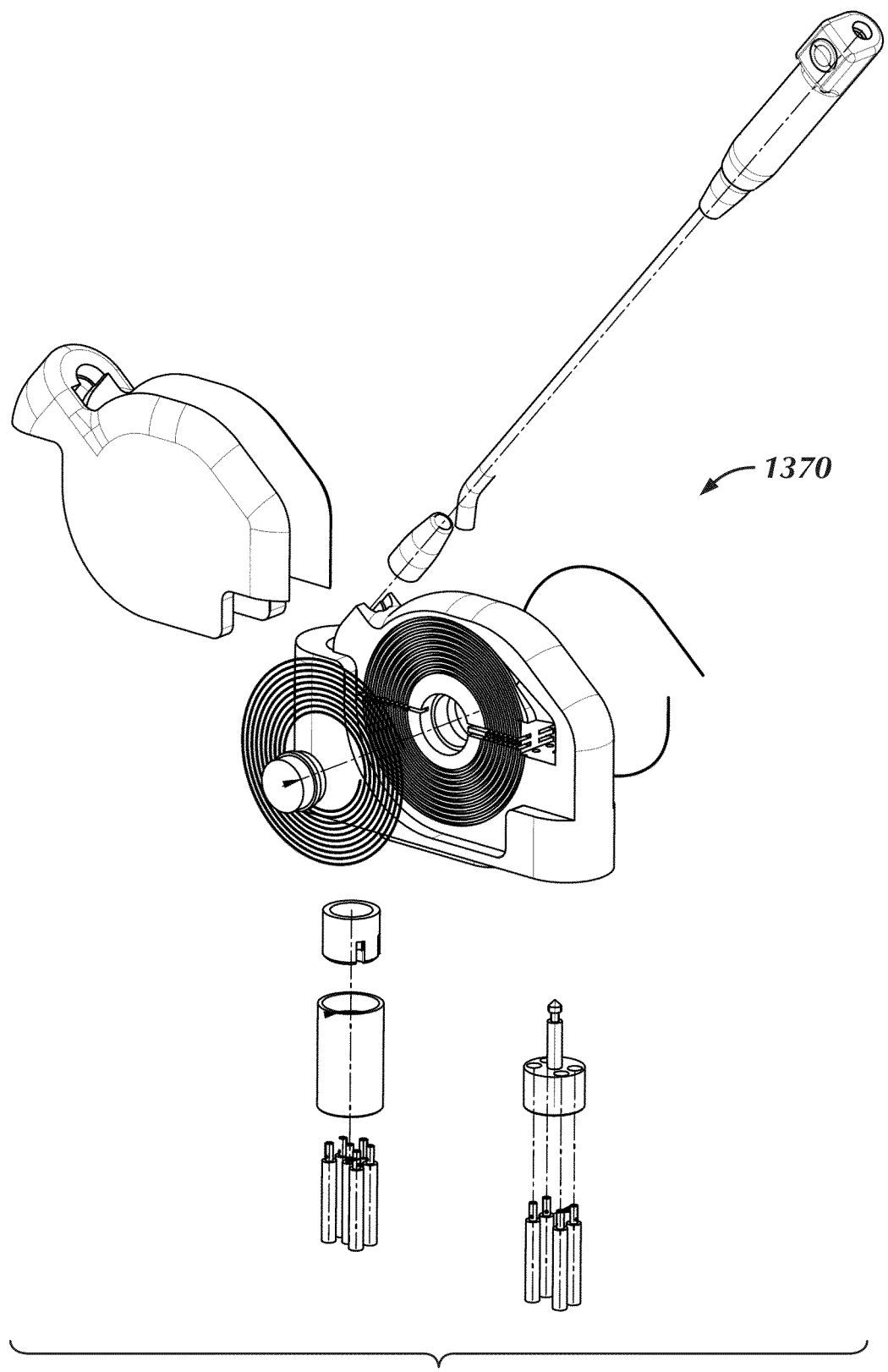
FIG. 16 is an exploded perspective view of the IPG and the silicone header components, the connector components which attach to the feedthroughs, the guides for the connectors, the inductive charging coil, the antenna coil, the magnet and the inline connector assembly with strain relief.

The Implantable Pulse Generator 1370 (IPG) for the OSA system is shown in FIG. 13. The IPG 1370 may be housed in a titanium enclosure, containing the secondary Lithium-Ion battery, the printed circuit board (PCB) assemblies, radio-opaque marker, and support structures. The IPG 1370 may be covered by a hermetic enclosure. The titanium material may be consistent with metals traditionally used to house Active Implanted Medical Devices (AIMD). The top of the titanium case may be sealed with a titanium plate through which two feedthrough assemblies are attached. One feedthrough assembly may contain four feedthrough pins, two of which may be used for an inductive charging coil located outside the hermetic enclosure and inside the header assembly, and two of which may be used for the Medical Implant Communications Service (MICS) telemetry coil similarly located. The second feedthrough assembly may contain six feedthrough pins, which may be connected to output pulse circuitry of the IPG 1370 and which connect eventually to the six contacts contained within the cuff electrode 764 that attaches to the HGN 322. An embodiment of the IPG assembly 1370 is shown in FIG. 13 showing the silicone header and inline connector separated from the IPG 1370 housing. FIG. 14 depicts the plastic battery support that protects the Lithium Ion battery inside the IPG 1370 enclosure. FIG. 15 depicts the completed IPG internal assembly with circuit boards fastened to the titanium header plate, the battery support and feedthrough assemblies being lowered into the titanium enclosure and completed by laser welding the enclosure to the titanium header plate. FIG. 16 shows an exploded view of the header elements, including the inductive link charging coil, the MICS telemetry coil, the magnet, the silicone inner and outer header elements, the crimp contacts which mate with the feedthrough pins, the Polyetheretherketone (PEEK) guides, and the inline connector assembly and strain relief. An alternative to this structure would utilize an epoxy header with the elements of the inline connector contained within the volume of the epoxy header, eliminating the PEEK components, crimp contacts and allowing the proximal connector of the electrode lead to be inserted directly into the IPG epoxy header.

Figure 12:
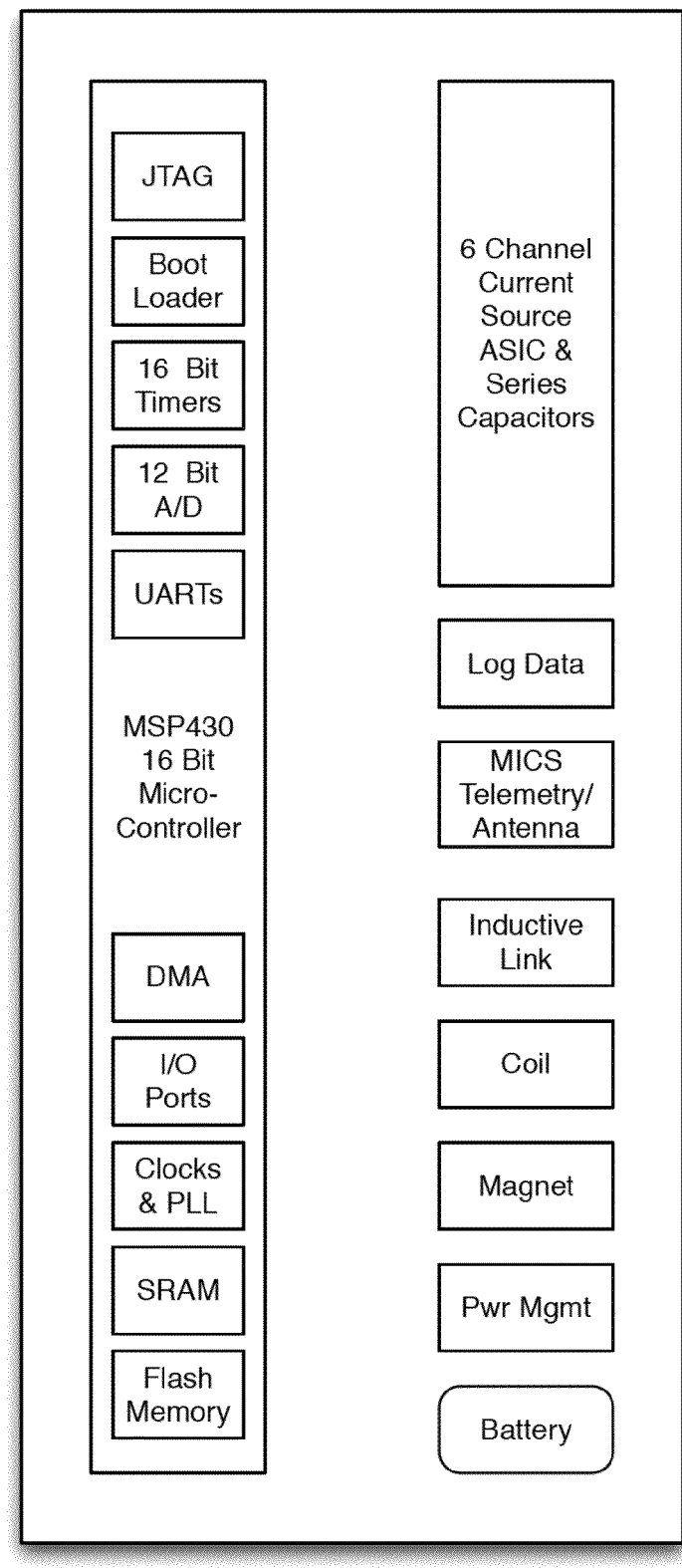
FIG. 12 is a block diagram of the IPG.

The IPG 1370 elements shown in the block diagram in FIG. 12 may consist of a 16 bit microcontroller, a MICS telemetry transceiver, a six channel custom Application Specific Integrated Circuit (ASIC) current source, a serial electrically erasable programmable read only memory (SEEPROM), inductive power receiving and modulating and demodulating circuitry, battery charging circuitry, power supplies and analog signal acquisition support circuitry. The microcontroller may have a large number of resources, including a 16 bit reduced instruction set core (RISC), 92 KBytes of Flash memory, 8 KBytes of RAM, a three channel DMA, a 12 bit analog to digital converter (A/D) and digital to analog converter (D/A), 16 bit timers with 10 capture and compare registers, four universal serial communication interfaces (UCSI) supporting enhanced universal asynchronous receiver/transmitter (UART), an Inter-Integrated Circuit ($I^2C$) and Synchronous Peripheral Interface (SPI) and a primary bootstrap loader with Joint Test Action Group (JTAG) interface to allow program development and memory programming.

The flash memory may be used to contain manufacturing data such as calibration information, patient specific data, and other constants which need to be kept in a permanent location, as well as a secondary boot loader and application code. In one embodiment, the secondary boot loader is required to allow transfer of code and data to the flash memory after the IPG 1370 is welded closed (JTAG programming may no longer be possible). The secondary boot loader may be stored in a location which is reserved for its use and, as viewed by the microcontroller, is actually the main application as it is activated upon power on reset (POR) (the reset vector points to the boot loader). The secondary boot loader may initialize the system and wait for a finite period of time before either responding to manufacturing software loader commands or if no commands are received jumps to the main system application. This architecture allows changes to be made in the flash memory of the device once the JTAG interface is no longer accessible (such as field upgrades to IPG 1370 device firmware). Should changes be necessary to the secondary boot loader program, highly specialized program images may be written that when executed can write a new image to the region occupied by the previous secondary boot loader.

Figure 17:
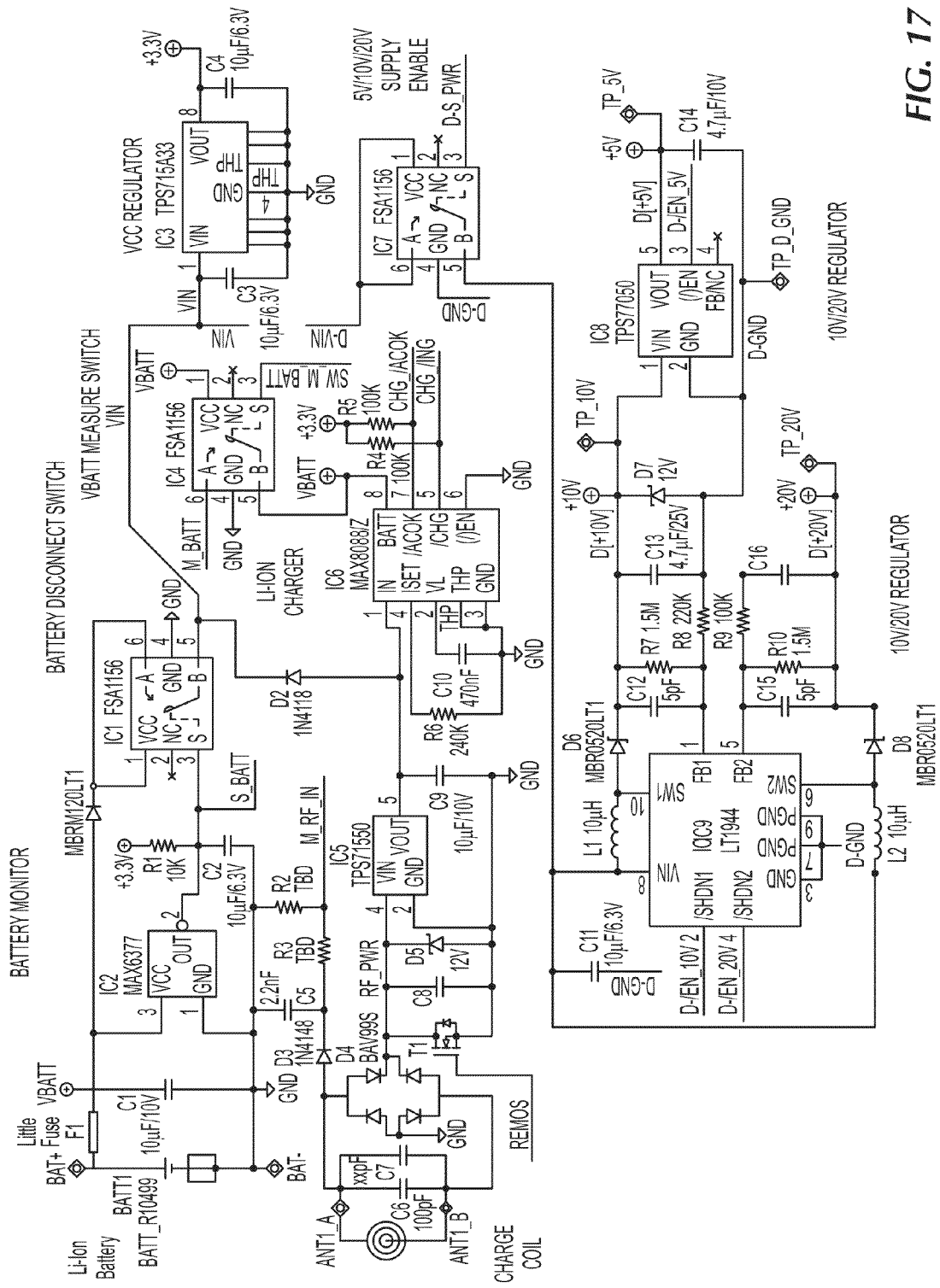
FIG. 17 is a schematic diagram of the IPG Power Sections.

The schematic diagrams for the IPG 1370 are shown in FIGS. 17 through 21. Beginning with FIG. 17 is the lithium battery, the charge coil circuit, battery monitor circuit, the battery disconnect circuit, the lithium ion battery charging circuit, the Vcc regulator circuit, the 5V/10V/20V supply enable and voltage regulator circuits. A resettable fuse may protect the battery from over discharge and the battery monitor circuit may protect the battery from under-voltage conditions. At 3.1V, IC2 monitor circuit may generate an open-collector low level which drives the analog switch IC1 to disconnect the battery from the system VBatt signal. The signal S_Batt may be driven from an I/O port on the microcontroller to enable battery disconnection under program control to allow the IPG 1370 to be placed into a low power shelf mode for long term storage without battery depletion. Upon disconnection of the battery, re-connection may be enabled upon application of a charge field to the charge coil. The charge field may be bridge rectified and zener limited and supplies power to voltage regulator IC5, which in turn drives battery charger IC6 to replenish power to the battery and to supply system power. Battery power and charge power may be isolated from each other by diodes D1 and D2. Upon application of charge power and re-connection of the battery the microcontroller goes through its POR sequence and starts executing its primary and secondary boot loaders, described below.

Figure 18A:
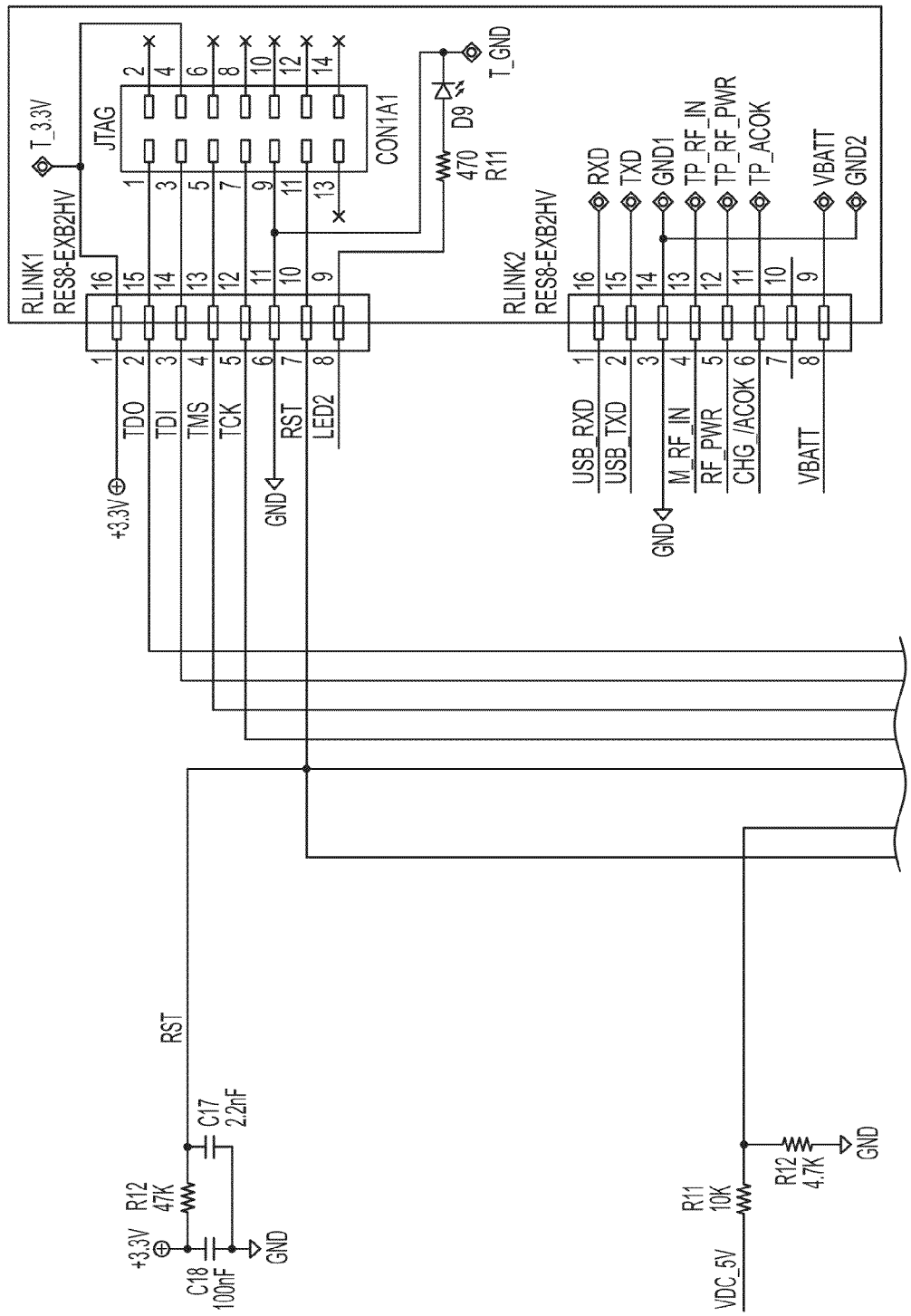
FIG. 18A is a first schematic diagram section of the IPG Microcontroller Section and Log Memory.
Figure 18B:
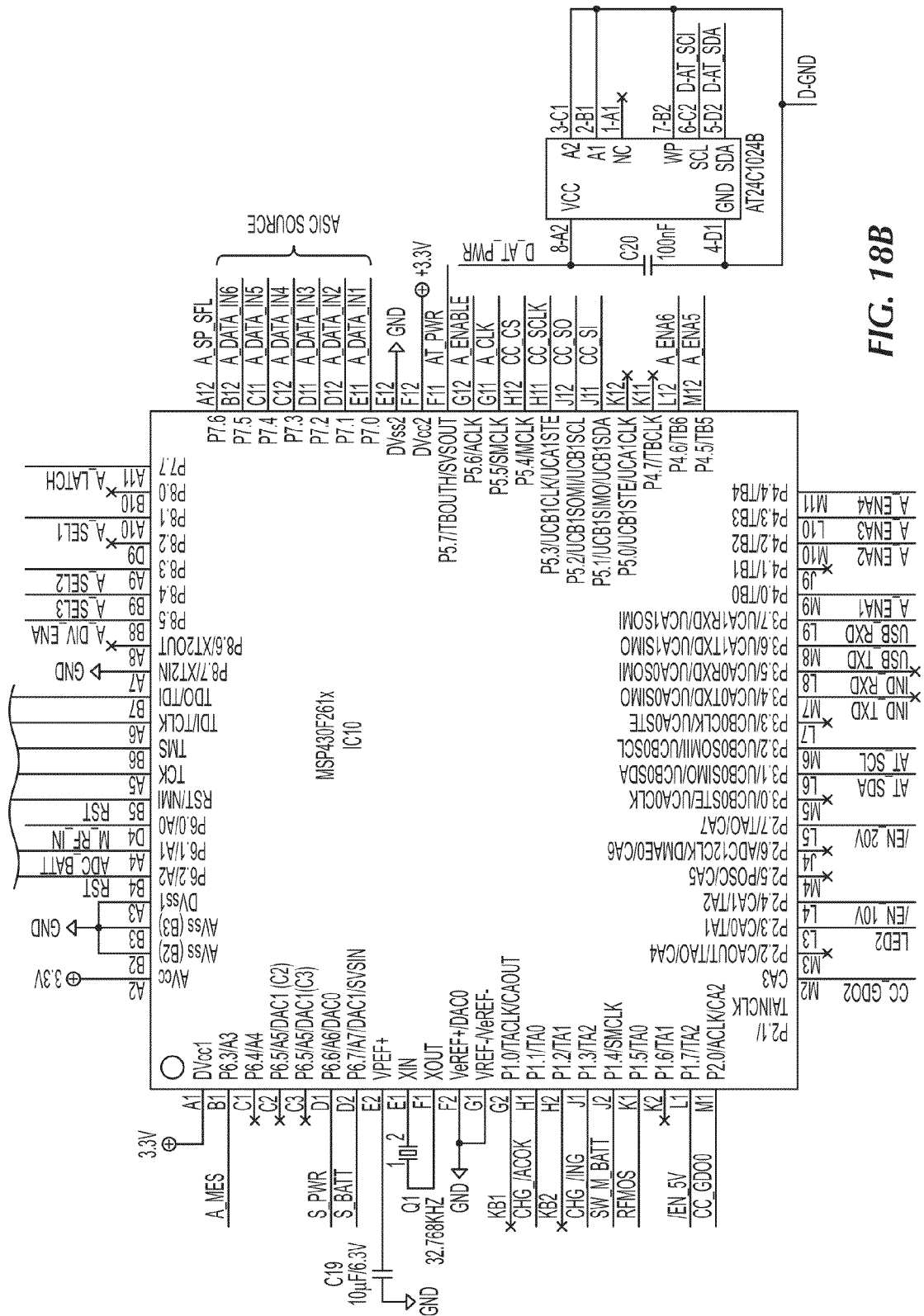
FIG. 18B is a second schematic diagram section of the IPG Microcontroller Section and Log Memory.

FIG. 18 depicts an embodiment of the microcontroller and log memory circuits, as well as the manufacturing JTAG communications connections. The microcontroller may contain all system memory with the exception of event log memory which is interfaced to the microcontroller using an I²C interface. This non-volatile memory may be organized as a ring buffer to keep only the latest events that occur during system operation. Optionally, log memory may be contained as well within the Flash memory space of the microcontroller.

Figure 19:
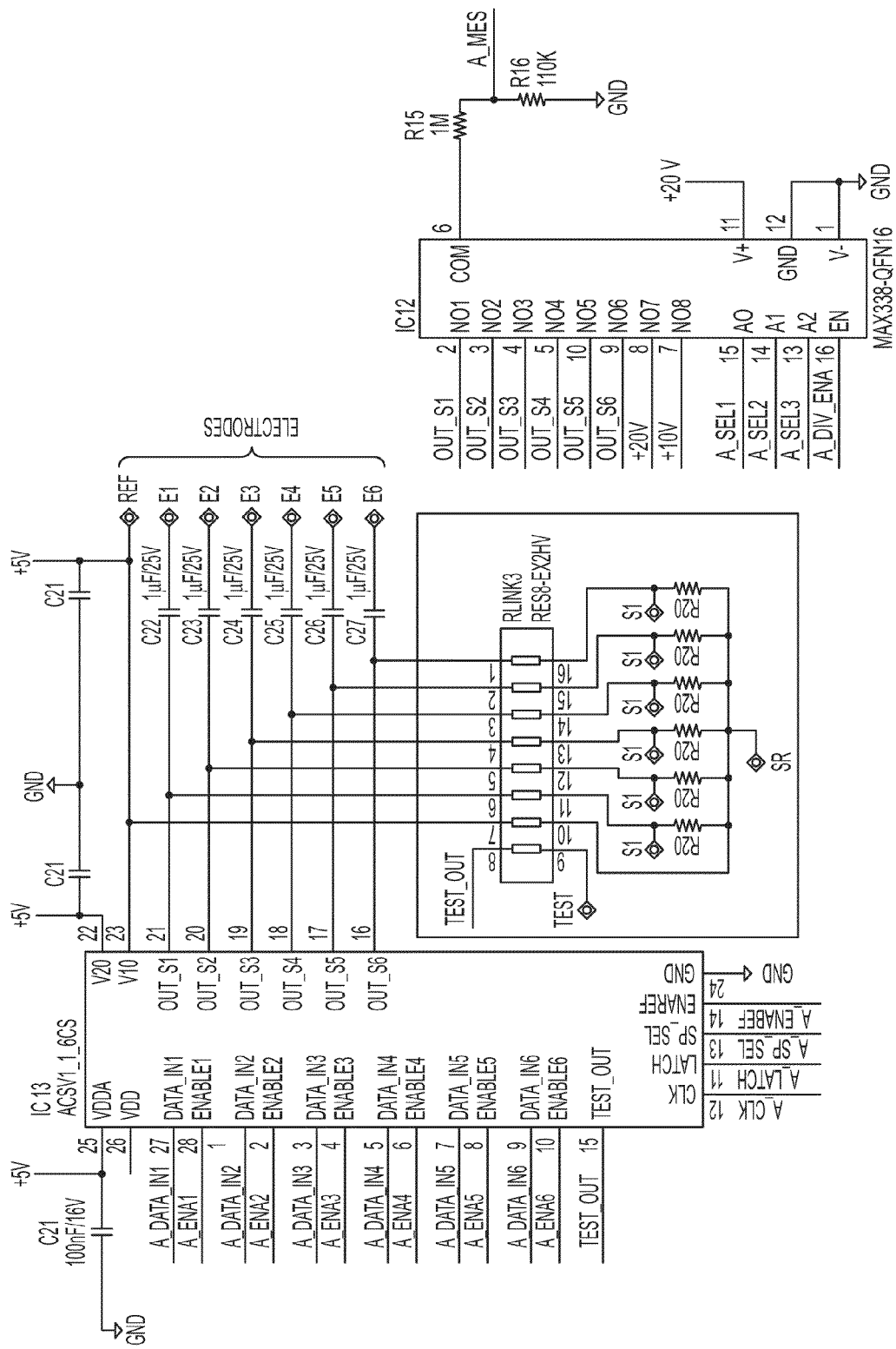
FIG. 19 is a schematic diagram of the IPG Pulse Generation and Analog Signal Sampling Circuits.

FIG. 19 depicts an embodiment of the six channel current ASIC used for pulse generation and the series output capacitors used to prevent DC current leakage. A manufacturing test load is shown, which may be removed from the PCB after testing is completed. An analog multiplexer is shown which may allow voltage samples to be taken to measure electrode/tissue impedances and compliance voltage levels. The six channel current ASIC is comprised of six identical current sources organized with shift register interface to the microcontroller, data latches for amplitude settings, and on-chip current mirror references and control circuitry. Each shift register may be driven individually or may be daisy-chained for drive from a single data line. Clock lines, selects, address lines and enable lines all coordinate the transfer of data into the current source logic. The current sources are referenced to the 10V supply and supply biphasic current using the ground and 20V supplies for source and sink current generation. The current sources may use quasi-logarithmic methods with eight bit data plus sign bit to control the level of current supplied. The logarithmic scale may be approximated by eight linear segments with their own current step and offset, resulting in very fine current steps at low amplitudes and progressing to coarser steps as the current reaches its maximum levels.

Figure 20:
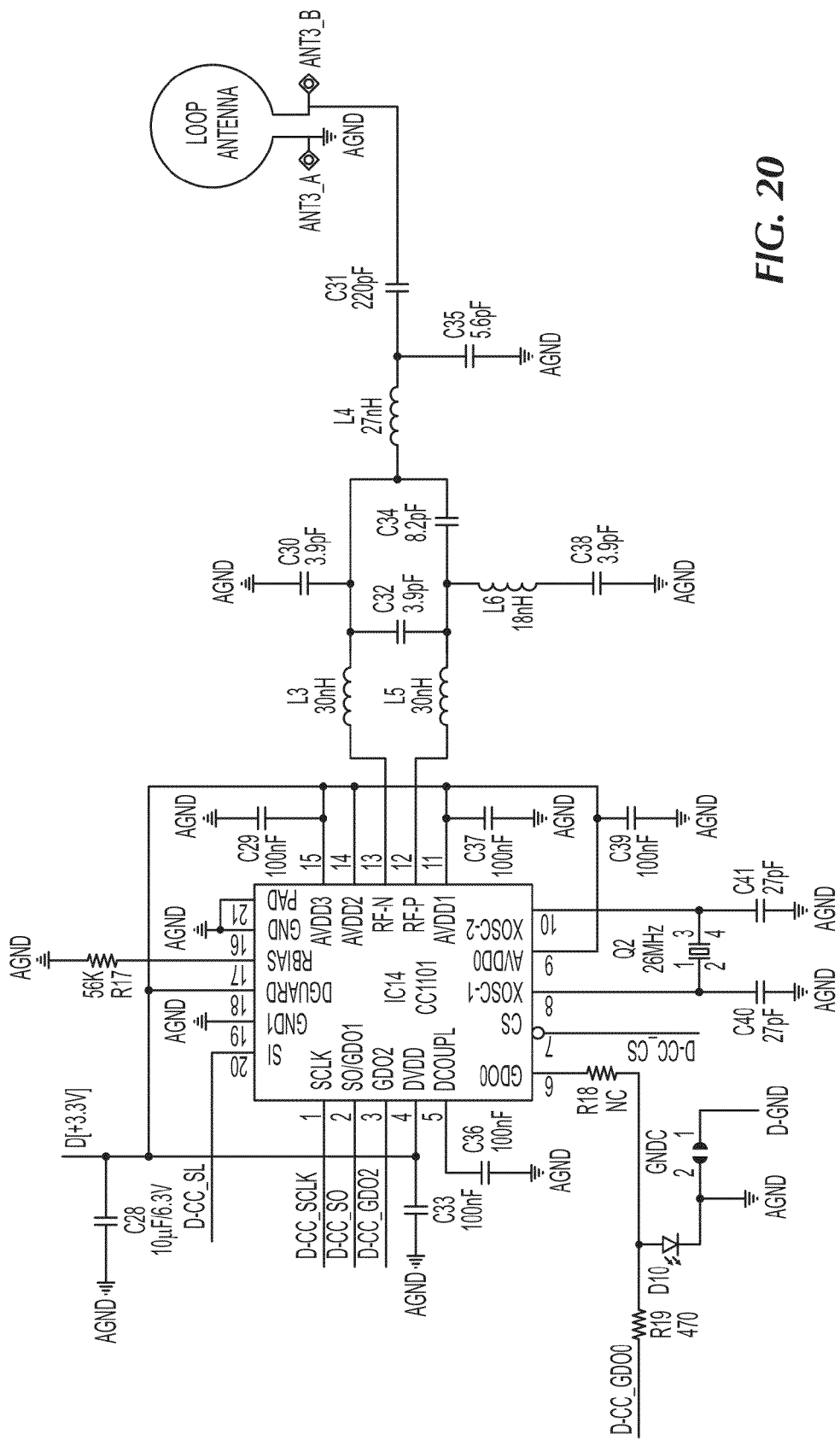
FIG. 20 is a schematic diagram of the IPG Medical Implant Communications Service (MICS) Telemetry Section.

FIG. 20 depicts an embodiment of the MICS telemetry circuitry and loop antenna located in the silicone header of the IPG 1370. The MICS telemetry circuit uses the 400 MHz band to transfer data to and from the IPG 1370 using secure data packets with RF identification, device identification, command parsing and sixteen bit cyclic redundancy check (CRC16) codes to detect errors in the data transfer process. FIG. 21 depicts the connectors that may allow the two PCB assemblies of the IPG 1370 electronics to be attached together along with a test board that allows the boards to be connected in a flat setting suitable for testing.

Remote Control and Charger (RCC)

Figure 22:
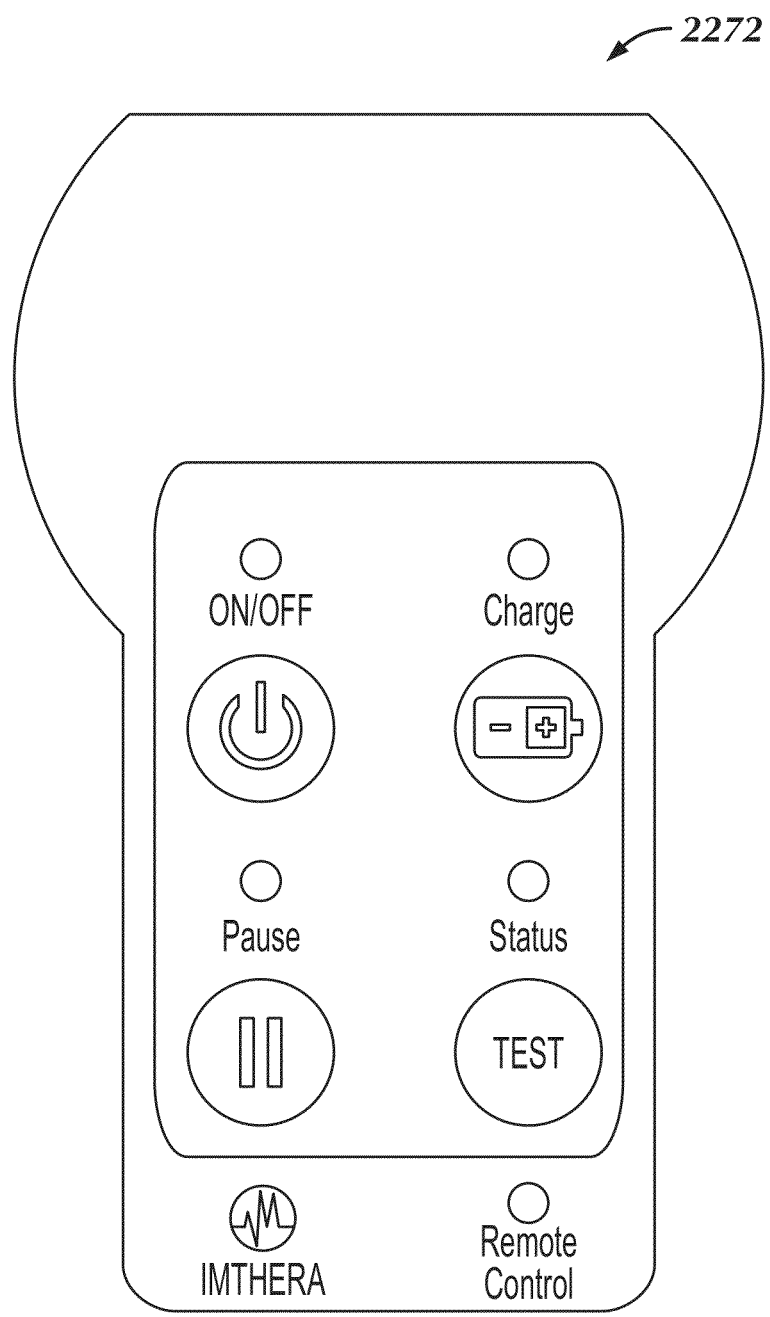
FIG. 22 is a diagram of the Remote Control and Charger (RCC) Front Panel Keyboard and LEDs.

The Remote Control and Charger 2272 (RCC) is a handheld device which may be used by the patient to operate and wirelessly charge their IPG 1370, and by the physician and clinical engineer to program the IPG 1370. To serve these two roles, the RCC 2272 may operate in two modes. In the primary mode, the RCC 2272 may respond to key presses on its membrane switch panel, perform the functions requested, and display the results on its front panel LEDs. In the secondary mode, the RCC 2272 may act in pass-through fashion, receiving commands from the aura Clinical Manager (aCM) software via a Universal Serial Bus (USB) connection to a personal computer (PC), and transferring those commands to the IPG 1370 through its MICS telemetry interface. Responses and data from the IPG 1370 may be received by the RCC 2272 and passed back to the aCM. In similar fashion, the RCC 2272 may be used in the manufacturing process when connection through the JTAG interface is not available. The front panel of the RCC 2272 with its keyboard and LED user interface is depicted in FIG. 22.

In one embodiment, the RCC 2272 is housed in a plastic enclosure, containing either a set of secondary nickel metal hydride (NiMH) AA batteries or alkaline AA batteries, a printed circuit board (PCB) assembly, a membrane switch panel and LED displays. The battery compartment may be accessible by the patient to replace the rechargeable batteries should they wear out, or use alkaline AA batteries when traveling. Located just above the battery compartment are metal contacts that provide connection to the internal charging circuitry of the RCC 2272. When the RCC 2272 is placed upon the docking station 5378, these metal contacts may align with spring loaded metal contacts in the docking station 5378 which provide power to the RCC 2272 to recharge the RCC 2272 when it is not in use by the patient.

The RCC 2272 may have two connectors: one is a mini-USB connector used to connect to the aCM PC, and also allows charging of the internal battery. The second connector is a four pin circular connector which connects the RCC 2272 to the Charger Coil (CC). The CC may receive power and control signals from the RCC 2272 and allows a secondary inductive link channel to transfer and receive information with the IPG 1370 should the MICS telemetry link be non-functional. The second four pin connector may also be used during sleep laboratory tests to provide an indicator to the clinician which stimulation group is active. A special cable may be provided that interfaces to the various brands of PSG equipment.

Figure 23:
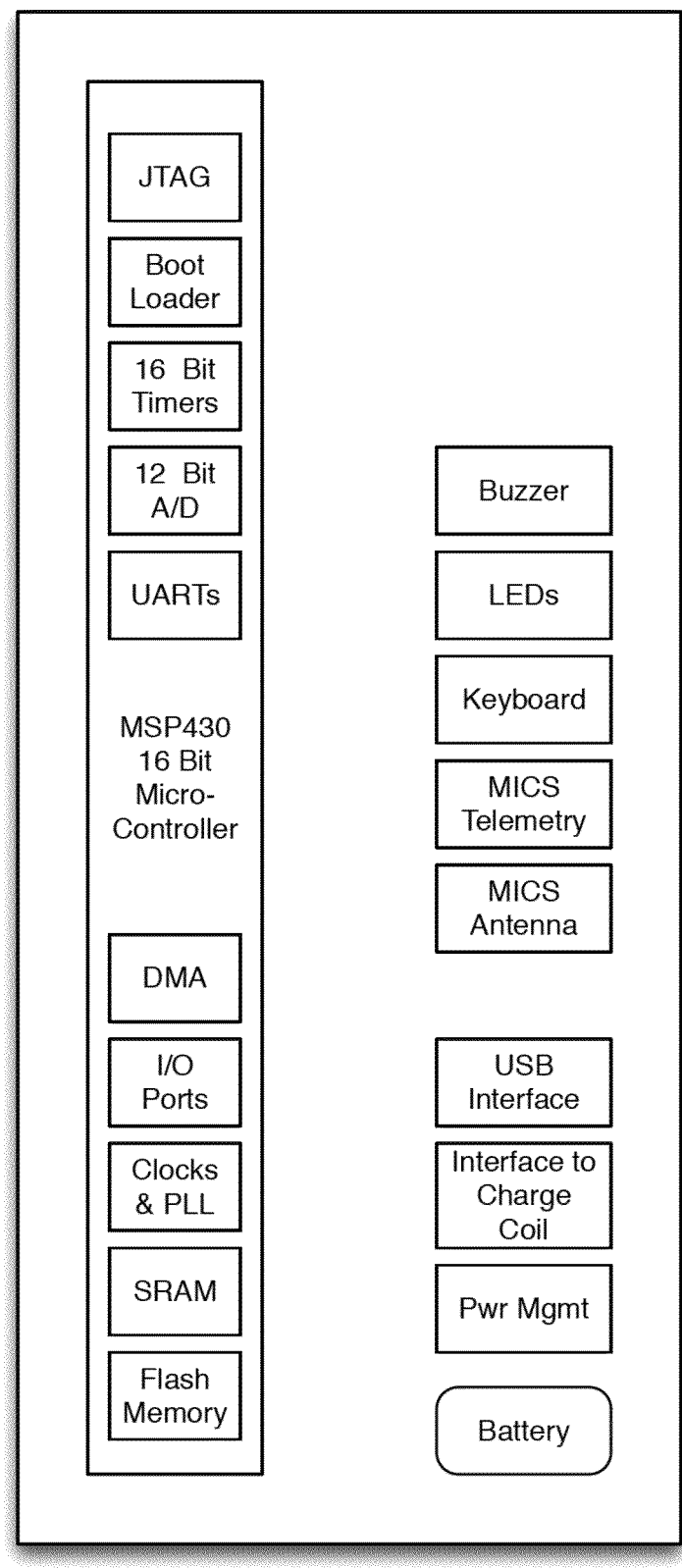
FIG. 23 is a block diagram of the RCC.

The RCC elements are shown in the block diagram FIG. 23 and may consist of a 16 bit microcontroller, a MICS telemetry transceiver, inductive power interface circuitry, battery charging circuitry, power supplies and analog signal acquisition support circuitry. The microcontroller may have a large number of resources, including a 16 bit reduced instruction set core (RISC), 92 KBytes of Flash memory, 8 KBytes of RAM, a three channel DMA, a 12 bit A/D and D/A, 16 bit timers with 10 capture and compare registers, four UCSI ports supporting enhanced UART, an I²C and SPI protocols and a primary bootstrap loader with JTAG interface to allow program development and memory programming.

The flash memory may be used to contain manufacturing data such as calibration information, patient specific data, and other constants which need to be kept in a permanent location, as well as the application code. Unlike the IPG 1370, the RCC 2272 can always be upgraded to new firmware through the USB interface or the JTAG interface. Exemplary schematic diagrams of the RCC 2272 are shown in FIGS. 24 through 28. The flash memory of the RCC 2272 may also be used to log events in a similar manner to the IPG 1370.

Figure 24:
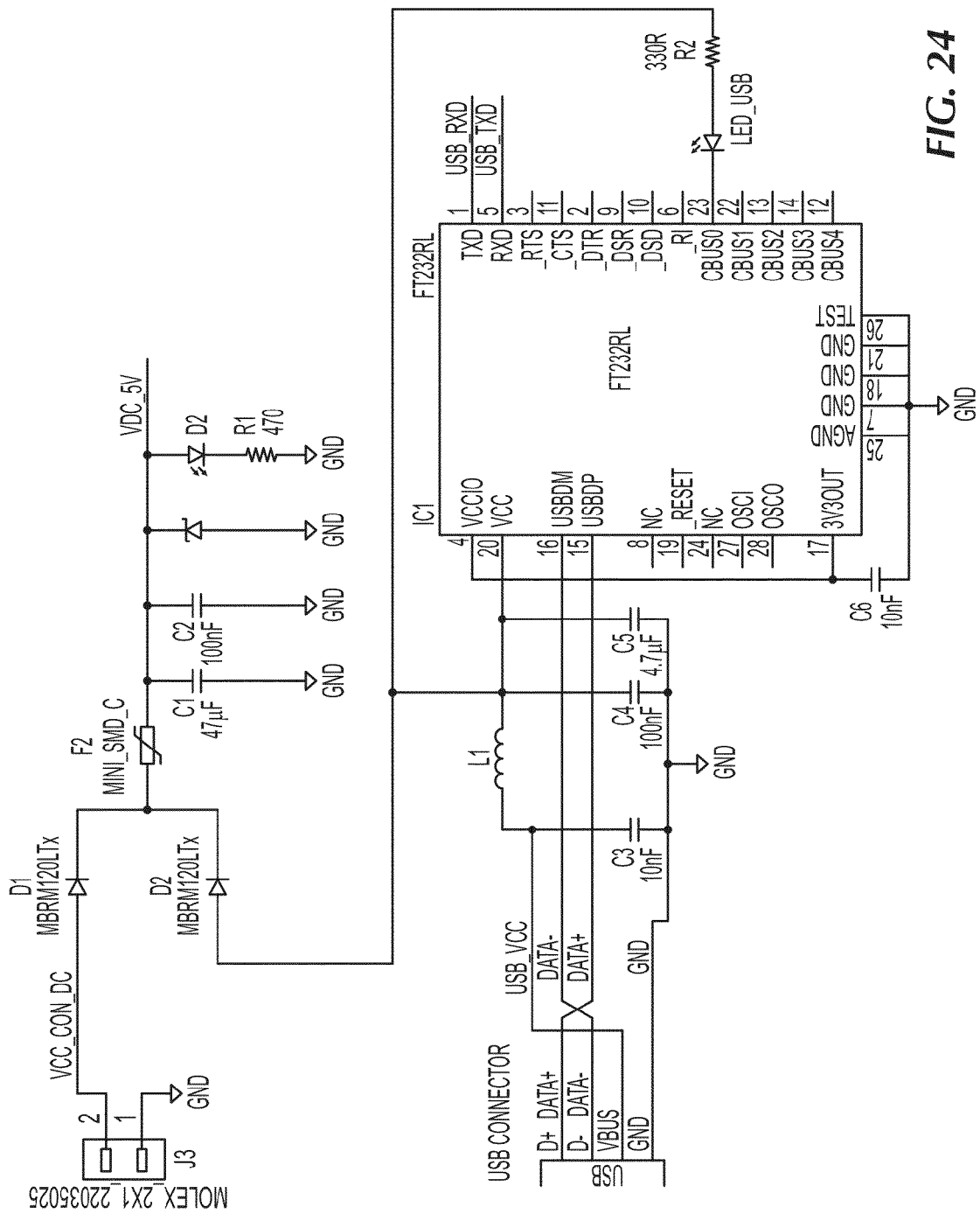
FIG. 24 is a schematic diagram of the RCC Docking Station and Universal Serial Bus (USB) Interface Sections.

FIG. 24 depicts the connection to the Docking Station 5378 and to the USB connection. The docking station 5378 may transfer 5V from a USB wall mount charger to metal contacts on the underside of the RCC 2272 chassis. This 5V signal may be fused and zener protected before being brought to internal circuit elements of the RCC 2272. The USB connector may be additionally capable of supplying 5V power, as well as providing the communication link to the aCM through circuit IC1, a USB transceiver. The Docking Station may have its own internal power supply and the USB connector may be replaced by a power cord connection to household power.

Figure 25:
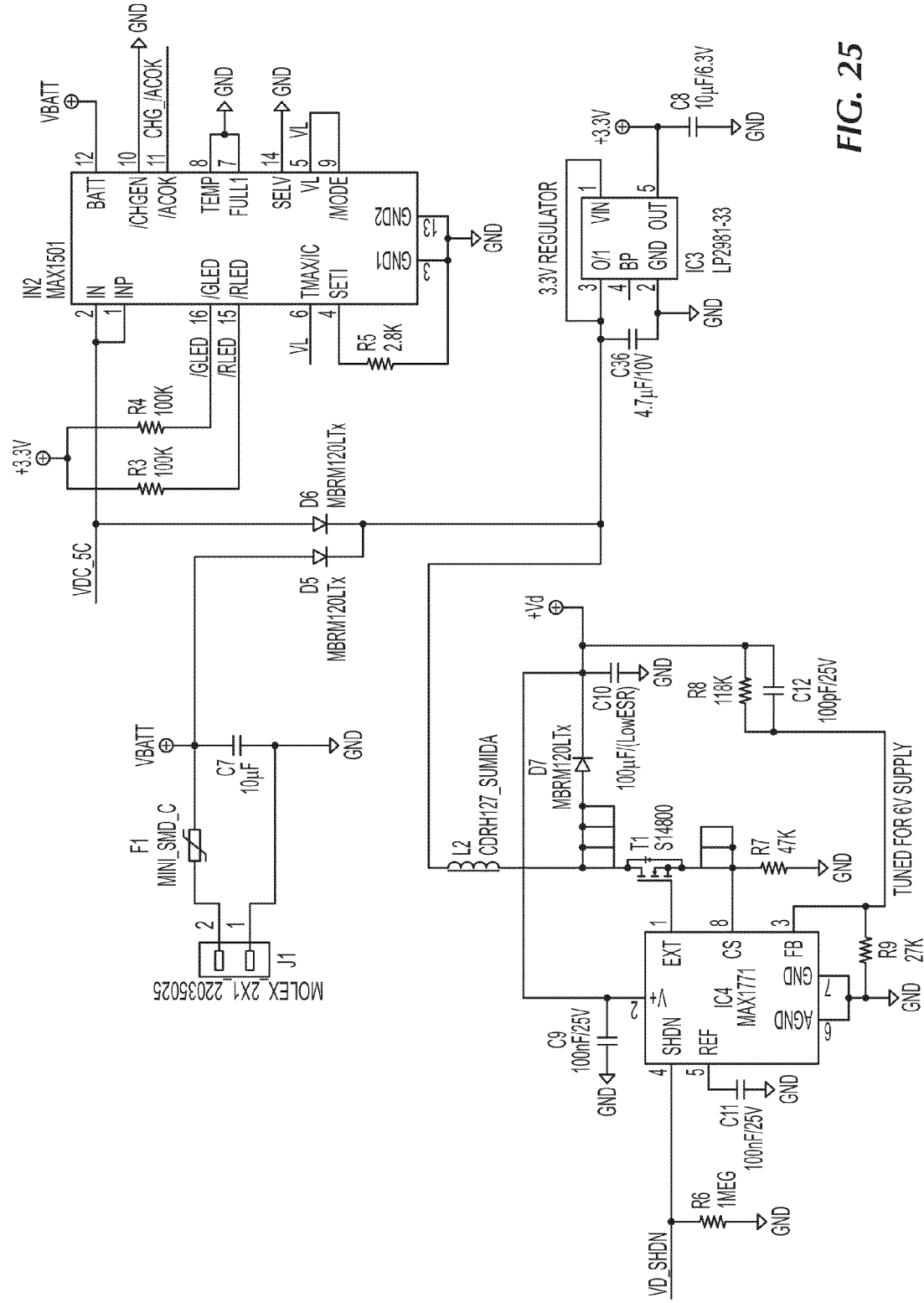
FIG. 25 is a schematic diagram o the RCC Power Sections.

FIG. 25 depicts the connection to an internal three AA cell battery pack, typically comprised of NiMH cells, or alkaline cells. The NiMH cells can be recharged, the alkaline cells can be replaced. The battery may be protected from over discharge by a resettable fuse. In one embodiment, power from the previous diagram is used to power the NiMH charger circuit, IC2. From either the power from the previous circuit or the battery a Vcc 3.3V regulator, IC3, may provide system power for the microcontroller and other logic. In one embodiment, power may also be supplied to IC4 which generate the 6V or 8V supply for operating the charging coil, which supplies power to the IPG 1370 for charging its internal lithium ion battery.

Figure 26A:
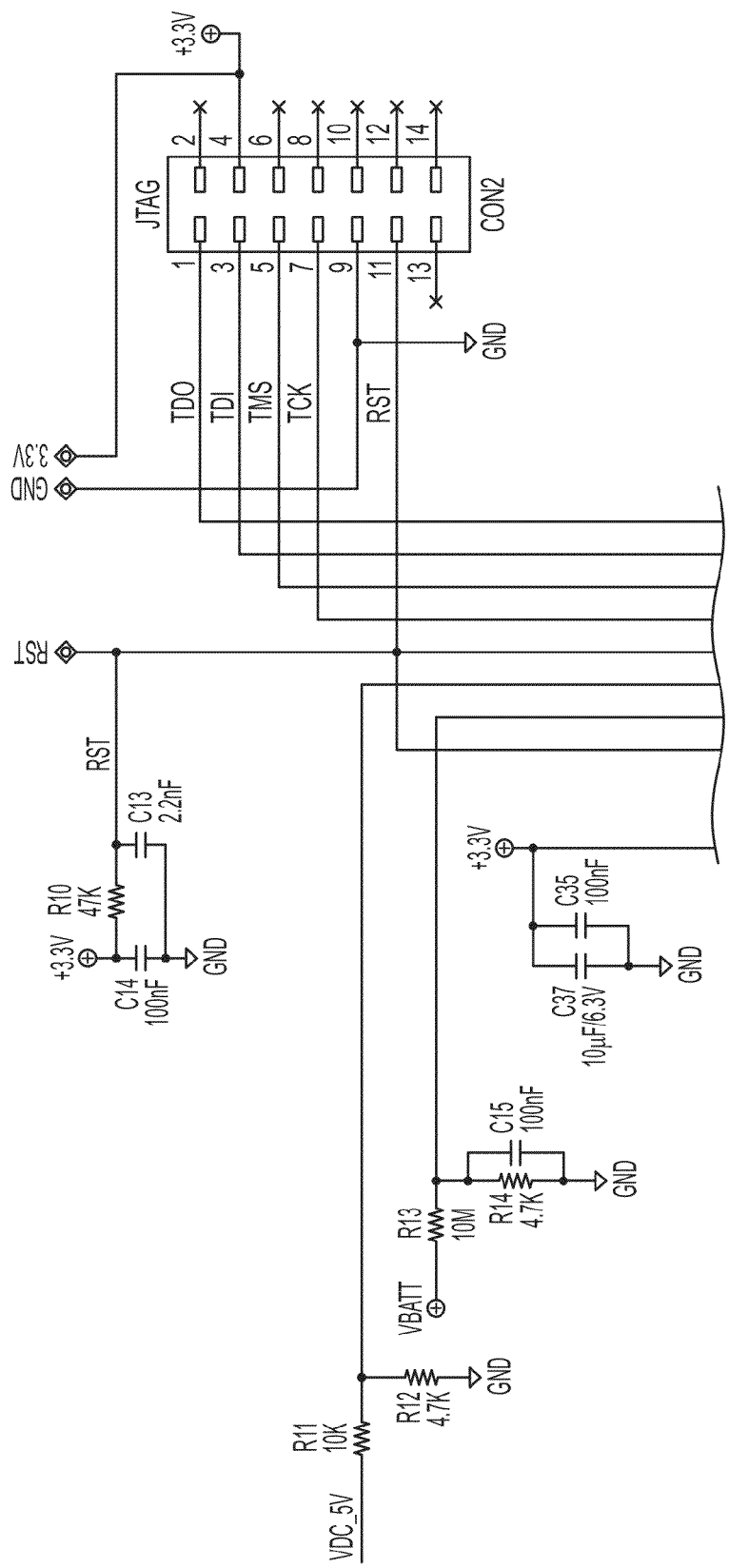
FIG. 26A is a first schematic diagram section of the RCC Microcontroller Section.
Figure 26B:
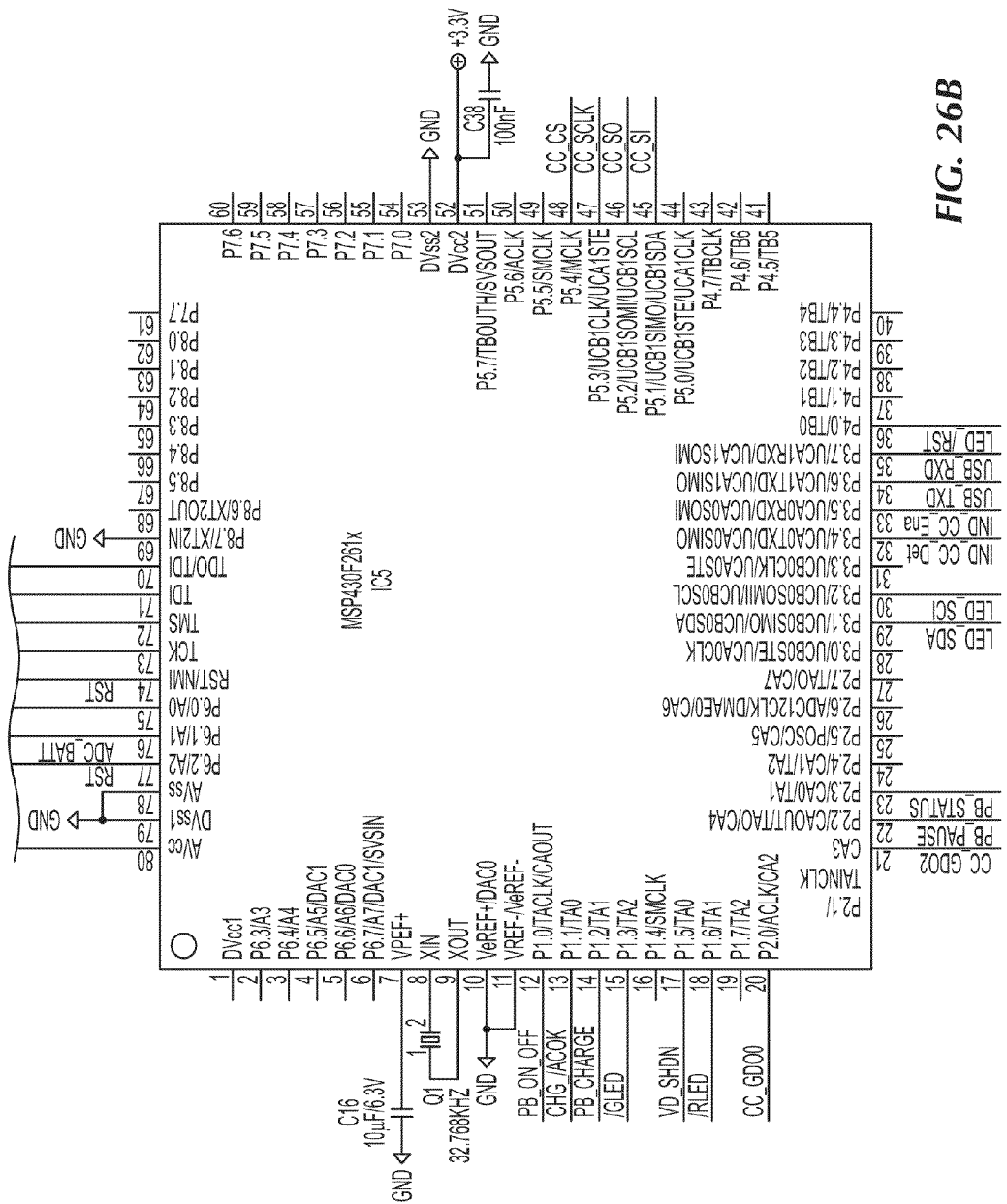
FIG. 26B is a second schematic diagram section of the RCC Microcontroller Section.
Figure 27:
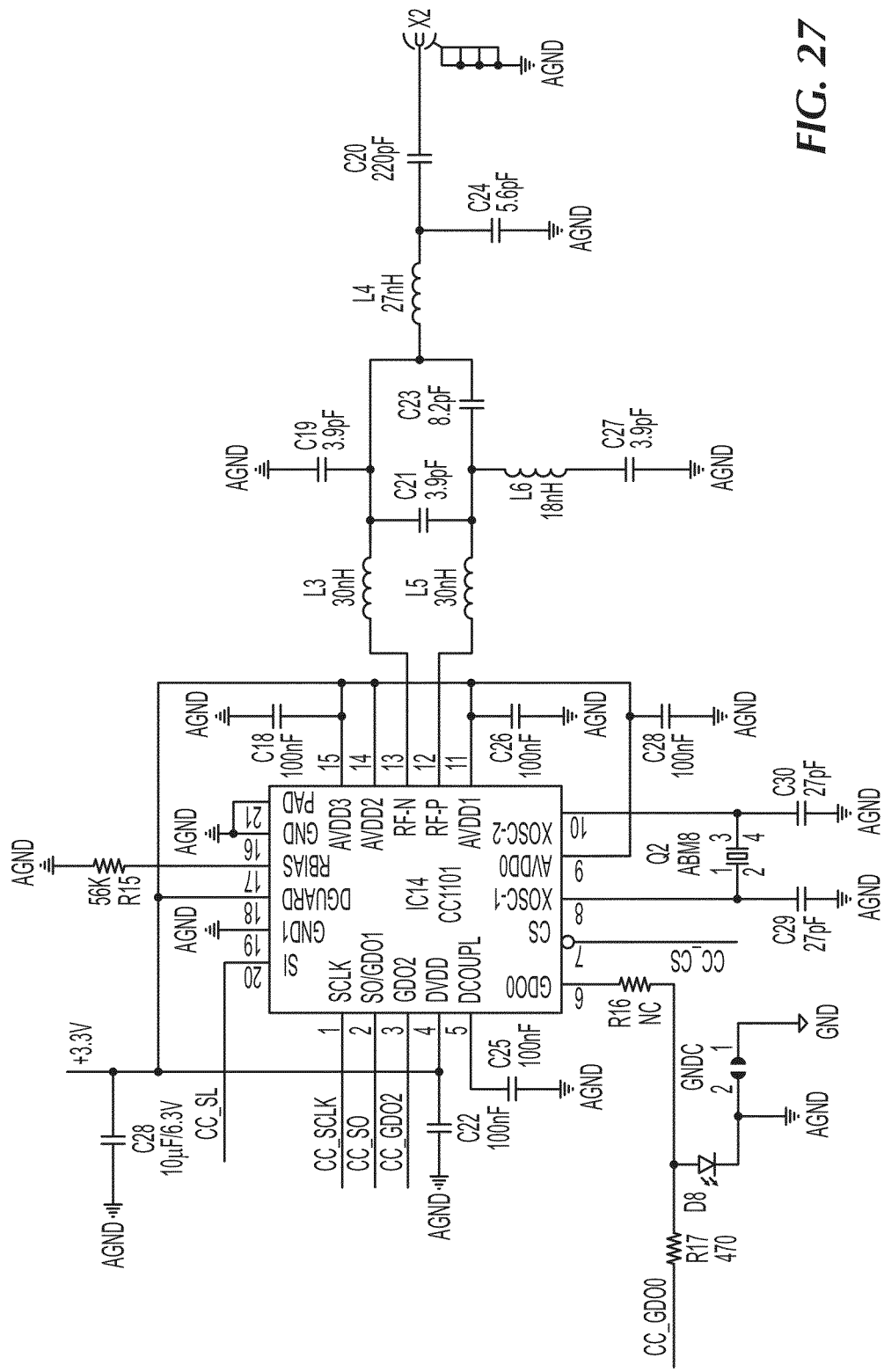
FIG. 27 is a schematic diagram of the RCC MICS Telemetry Section.
Figure 28:
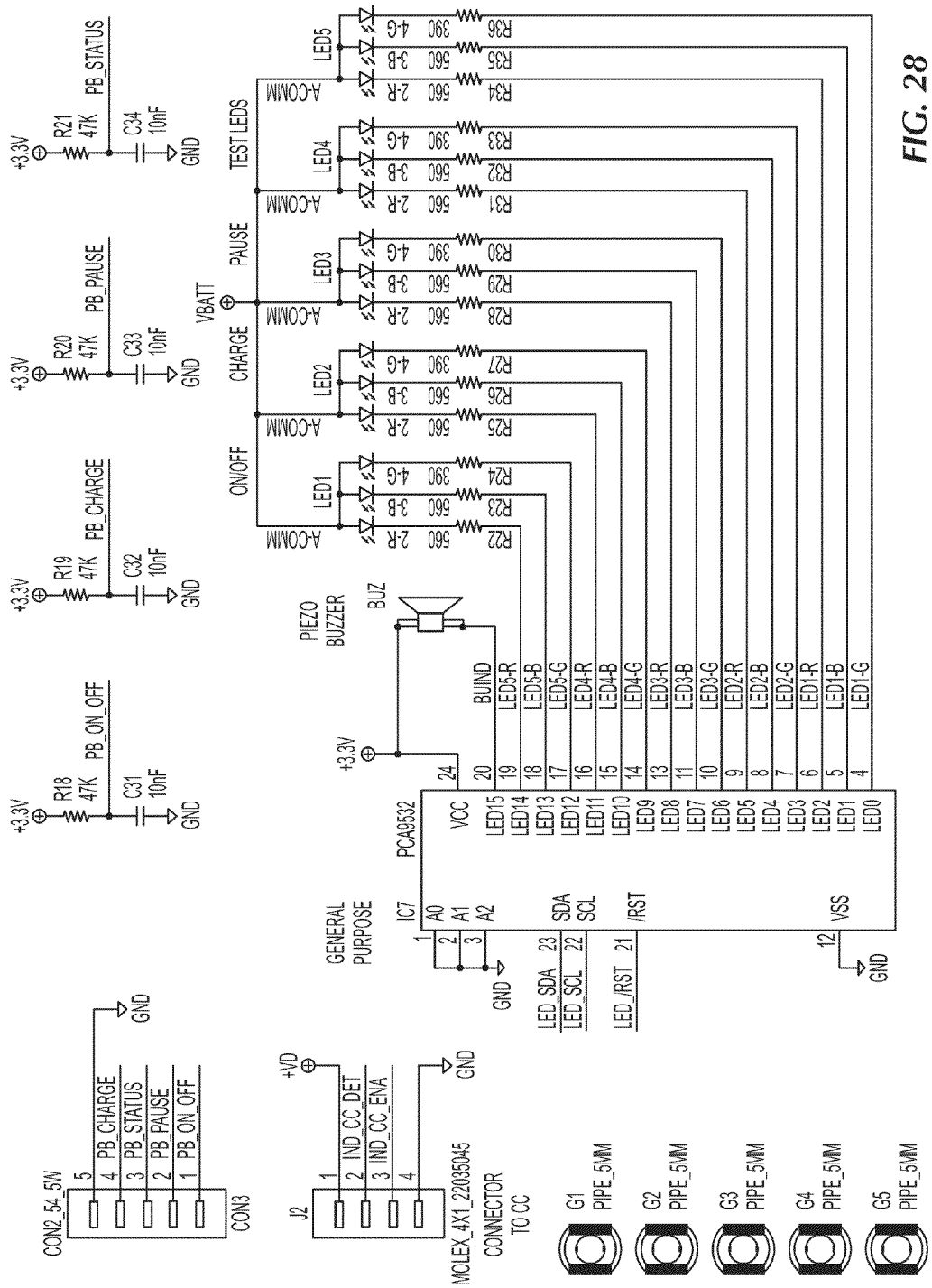
FIG. 28 is a schematic diagram of the RCC Keyboard and LED Sections.

FIG. 26 depicts an embodiment of the microcontroller and JTAG programming interface. Unlike the IPG 1370 which may lose its JTAG interface after programming and test in manufacturing, the RCC 2272 retains this connector in the finished assembly. FIG. 27 depicts the MICS telemetry transceiver circuit and the connection to an SMA type RF antenna which is housed inside the plastic enclosure of the RCC 2272. FIG. 28 depicts an exemplary user interface—a membrane switch panel, and the multi-color LEDS for the front panel. The LEDs may be driven by an I$^2$C interface port expander, IC7. In one embodiment, light from the LEDs is transferred from their position on the PCB to windows in the membrane switch panel through clear light pipes. A piezo buzzer may be driven from this same interface for provision of audible tones for the user. Exemplary membrane switch panel artwork is depicted in FIG. 22.

Alternatively the RCC may provide an LCD display instead of or in addition to the LEDs.

Charger Coil (CC)

Figure 29:
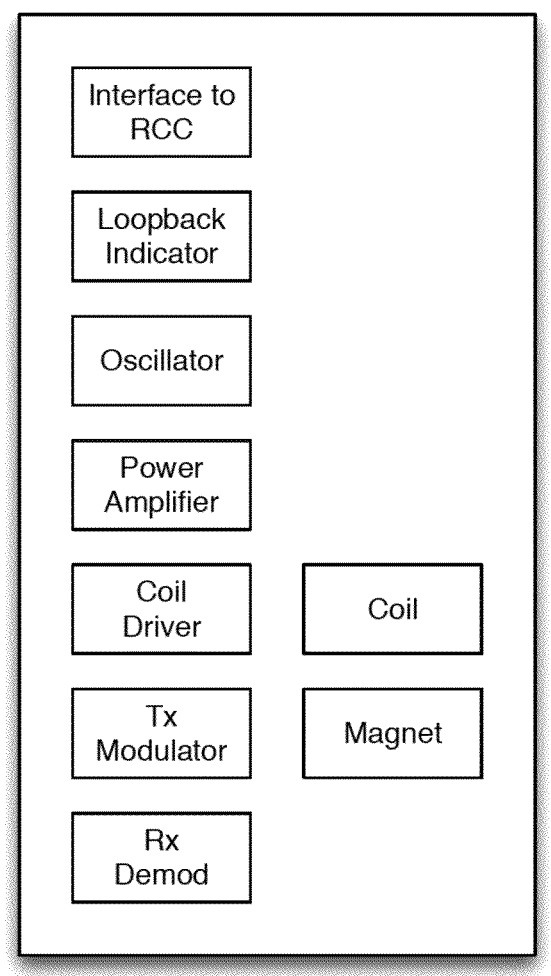
FIG. 29 is a block diagram of the Charger Coil (CC)

The Charger Coil 5374a (CC) may be a small device attached by a flexible cable to the RCC 2272 when it is necessary to charge the IPG 1370. An exemplary block diagram for the CC is shown in FIG. 29. In one embodiment, the CC assembly is comprised of a PCB housing the electronics necessary for its operation, the option of an embedded coil structure or a mounted inductive coil, and a magnet which aids in the alignment and retention of the CC to the IPG 1370. The IPG 1370 may contain a similar magnet in its inductive loop coil located in the header of the IPG 1370. Much like a cochlear implant, this simple alignment and fixation method may assure that the best possible energy transfer between the CC and the IPG 1370 occurs with as little impact upon the patient as possible.

Docking Station (DS)

The Docking Station 5378 (DS) may provide a convenient place on the patient's night stand to place and charge the RCC 2272 when it is not in use. Having convenient alignment and holding features, the patient can place the RCC 2272 into the DS 5378 in a single simple motion. The RCC 2272 may be easily removed as well for use when the patient wishes to operate the IPG 1370. In one embodiment, the DS 5378 has contacts on its top surface which mate with matching metal contacts in the RCC 2272. The DS 5378 may have a mini-USB connector for attachment to a wall-mounted USB charger. The charger can be unplugged from the DS 5378 and travel with the RCC 2272 to allow the RCC 2272 to be charged when the patient is traveling. The DS 5378 may have its own integrated power supply that uses a standard wall plug to acquire power.

Aura Clinical Manager (aCM)

The aura Clinical Manager (aCM) is a software application running on a personal computer. In one embodiment, the aCM is used by the clinical engineer or clinician to program an IPG 1370 and an RCC 2272 for a particular patient, and to fit and optimize a stimulation therapy for the patient. The aCM can run on a standard PC.

Memory, or alternatively one or more storage devices (e.g., one or more nonvolatile storage devices) within memory, includes a computer readable storage medium. In some embodiments, memory or the computer readable storage medium of memory stores programs, modules and data structures, or a subset thereof for a processor to control the RCC 2272, IPG 1370 and other system components described herein.

The aCM functionality may be divided along its use model applications, selected by a series of tab selections along the left edge of the screen. A local database on the computer may be maintained and synchronized automatically whenever an internet connection is provided to the computer. Database synchronization to the host database may ensure backup of all patient data and tracking of patient use of the implanted systems.

Patient Manager Screen

Figure 30:
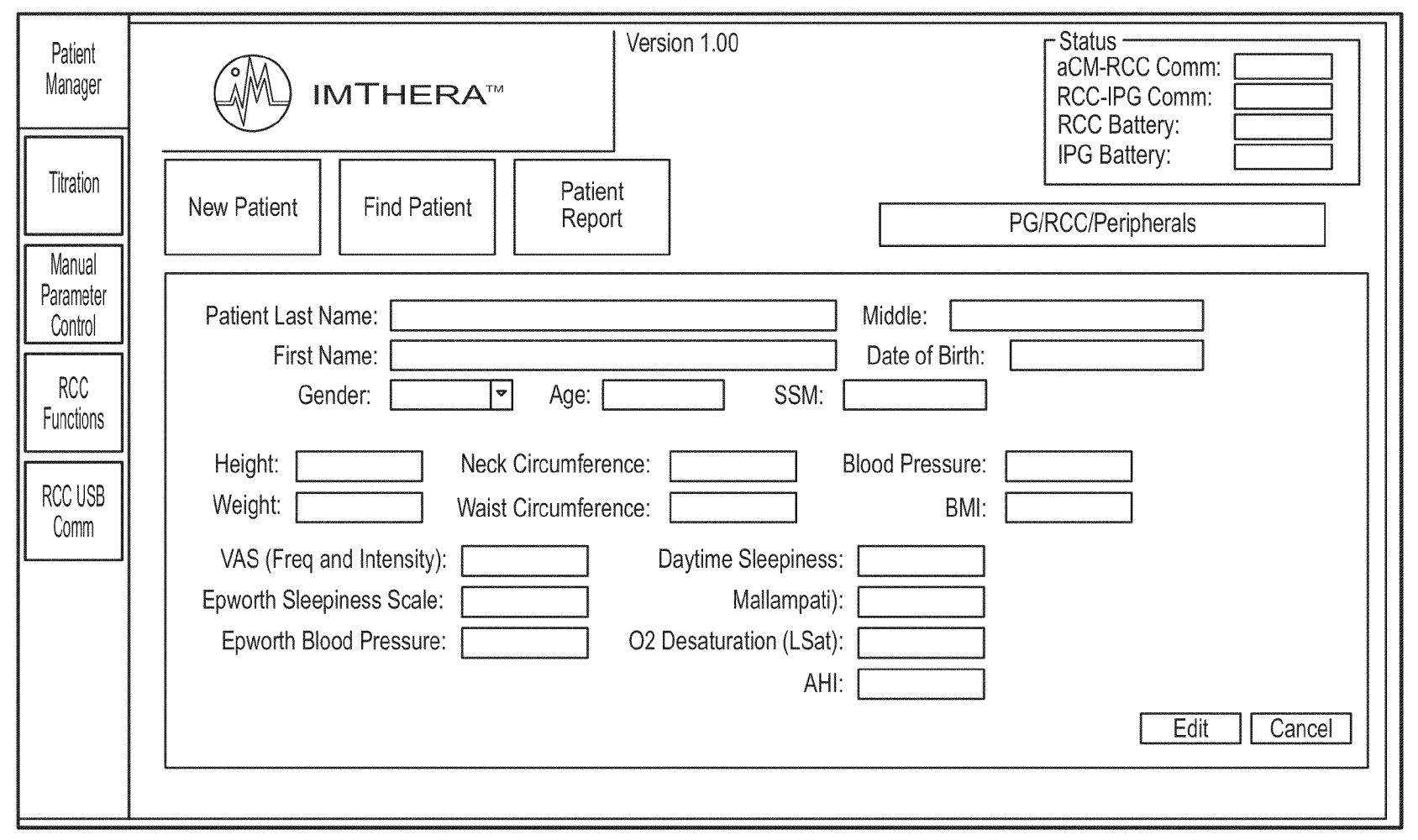

In one embodiment, the first screen is the Patient Manager screen, and is shown in FIG. 30. It is with this screen that a patient is first entered in the patient database and data collected pertaining to the patient's particular case of OSA. Existing patients may be located in the database by selecting the "Find Patient" and the system is able to find patient records that resemble the entry made by the user. Once a record is displayed, it can be selected. Reports may be generated for a patient on this screen as well and may be formatted for HTML for viewing as a file in a browser, such as Internet Explorer or Safari.

OSA system components may be issued to the patient and their issue date and serial numbers, as well as other pertinent information may be entered in the patient database as well. When elements of the system are replaced due to wear-out, loss, or failure, etc., the new elements may be entered into the database in a similar manner. Once all of the information for the patient is entered, the user may select any of the other screens.

Implant/Surgery Screen

The Implant/Surgery Screen may be the primary screen used by the clinical engineer or clinician to test the OSA system during the surgical implantation of the IPG 1370 and electrode. It is used in the operating room (OR) to test the system elements, to verify electrode impedances are in an acceptable range, and that the HGN 322 response to stimulation and threshold levels are acceptable.

Titration Screen

Figure 31:
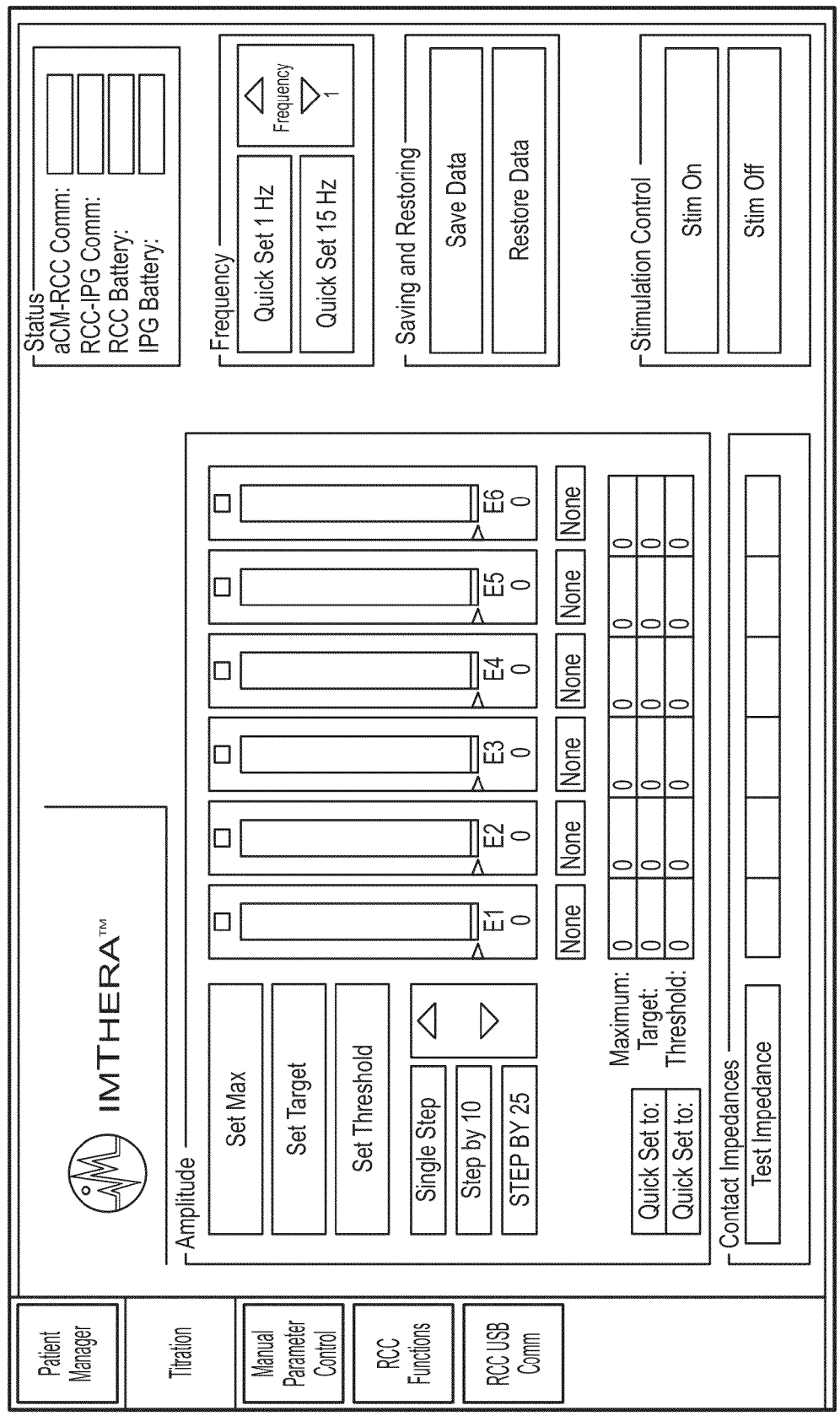
FIG. 31 is a depiction of the aCM Titration Screen.

The Titration Screen, an exemplary embodiment being depicted in FIG. 31 may be the primary screen used by the clinical engineer or clinician to fit the OSA system to the patient. Following surgery, approximately a week or more later, the Titration Screen of the aCM may be used for the main programming session for the patient. It is at this session where all of the stimulation parameters may be determined in preparation for a sleep study to verify the operation of the system in providing therapy for the OSA condition.

In one embodiment, the Titration Screen is divided into six sections. The largest section may be dedicated to Amplitude control where Threshold, Target and Maximum current amplitudes are determined for each of the six contacts of the system. Convenient Quick Set buttons may be provided to allow the amount of current at which amplitude changes with each increment or decrement of the up and down arrows, marking of Threshold, Target, and Max levels, and the setting of all enabled contacts to their Threshold or Target levels. In one embodiment, just to the right of this area are six slider controls with enable boxes to allow each contact to be tested individually or in concert with other contacts. When the Threshold is observed, selecting the Set Threshold button will transfer the value of the current for that contact to the Threshold box below the slider and a colored bar marker will be placed on the slider window at the current level. When the Target level is observed, selecting the Set Target button will transfer the value of the current for that contact to the Target box below the slider and another colored bar marker will be placed on the slider window at the current level. When the Maximum level is observed, selecting the Set Max button will transfer the value of the current for that contact to the Maximum box below the slider and yet another colored bar marker will be placed on the slider window at the current level. Threshold may be tested at 1 Hz while Target and Maximum may be selected at 15 Hz (or any other desired frequency that is greater than 1 Hz). Below each slider bar for each contact is an effect indicator, selected by a pull-down box, where the effect of the stimulation applied to the electrode is indicated (protrusor, retrusor, no effect, etc.).

The section directly below the contact slider controls may be the Contact Impedances section, and provides a quick way to request and receive contact impedance with respect to the case indifferent electrode of the IPG 1370. To the right, at the top, is the Status window. In the Status window the aCM to RCC USB communication status may be shown, the RCC 2272 to IPG 1370 MICS telemetry communication status may be shown, and the RCC 2272 and IPG 1370 Battery levels may be shown. In one embodiment, directly below this is the Frequency window in which the stimulation frequency may be set by increment or decrement, or quickly set to 1 or 15 Hz (same as pulses per second, or pps), with the resultant frequency shown below the up down buttons. In one embodiment, directly below the Frequency window is the Saving and Restoring window. This window may be used to save and recall program settings and patient data in a time and date stamped entry into the local patient database file. Multiple data records can be stored for a patient on the same day, and provision is made to annotate the records with a short field for quickly locating a record, along with a more detailed record that allows clinician descriptions of the actions taken to be captured. In one embodiment, the last window is the Stimulation Control window, and is used to start and stop stimulation.

PSG Screen

The PSG screen may be used during sleep laboratory studies to optimally allow easy manipulation of stimulation parameters by 5% variances and to allow monitoring of the IPG 1370 status during the test. Because the IPG 1370 operates independently, it is not easily discerned which stimulation group is active at a particular time. It is beneficial to identify which stimulation group is active to correlate this information with the data visible during the PSG test to verify that stimulation levels for that group are adequate or in need of adjustment. Normally the IPG 1370 only responds to commands received from a validated sender. In the PSG setting, the IPG 1370 may be enabled to transmit messages indicating when groups change, when channels ramp up or down, when groups delay and when they are in plateau phases. This information is sent to the RCC 2272 which can, using its four pin connector, generate signals that can be monitored by the PSG system to allow indication of IPG 1370 activity to be recorded with all of the other PSG measurements. In addition, the aCM can use its USB connection to the RCC 2272 to periodically inquire what the status of the IPG 1370 is and display that information on a location within the PSG screen.

Manual Parameter Control Screen

Figure 32:
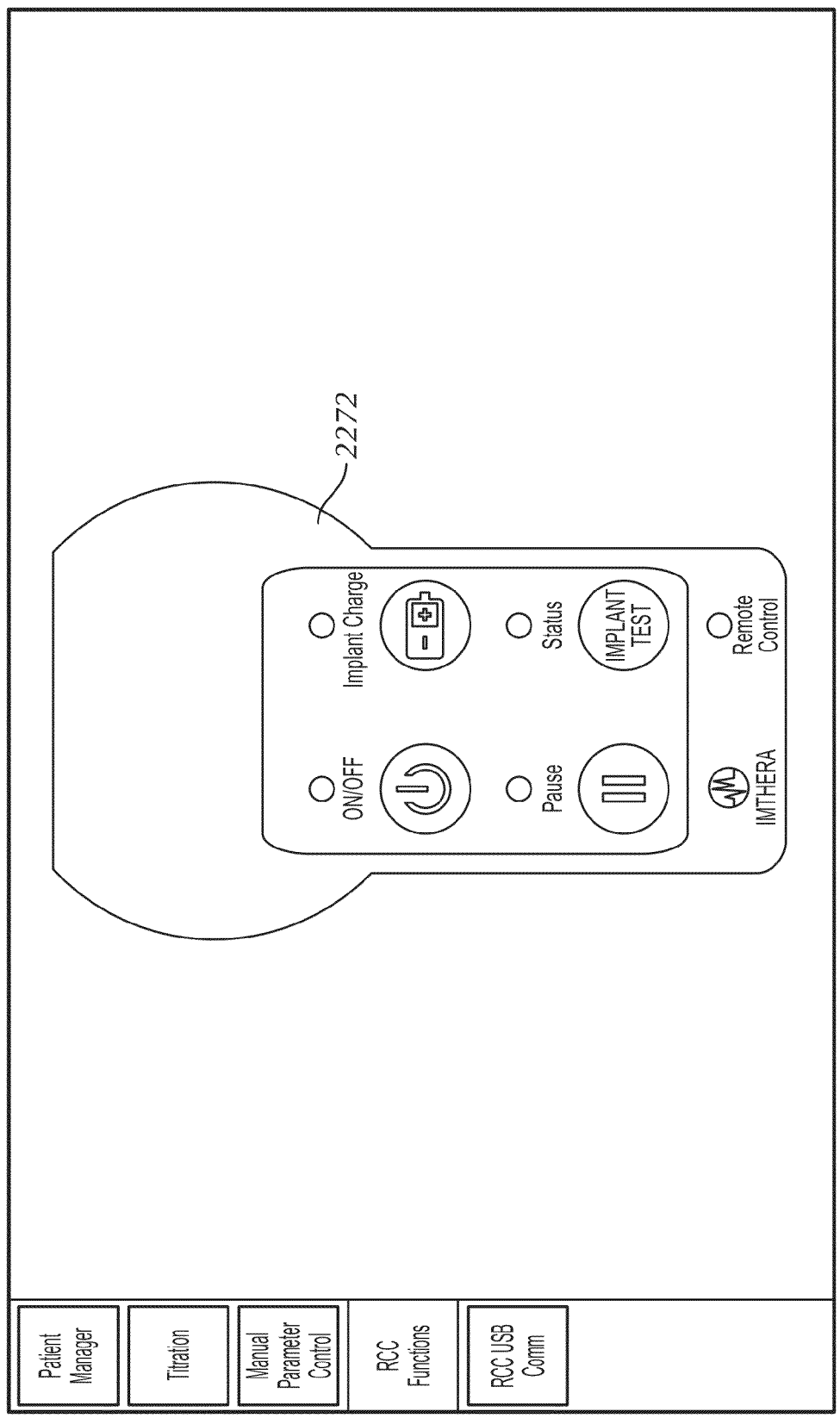
FIG. 32 is a depiction of the aCM RCC Functions Screen.

The Manual Parameter Control Screen, an exemplary embodiment being depicted in FIG. 32 may be used to set parameters that are typically not changed from their default values, but which might be changed under certain conditions. In one embodiment, the screen is divided into two main sections—one in which stimulation parameters and logs may be viewed, and another section with status and data transfer operations are conducted. The top left sections may be used for setting and viewing Global IPG Parameters, such as Startup Delay (or Sleep Session Delay), Pause Delay, etc., while the section just to the right is the Group Parameters section. Groups can consist of as few as one electrode contact, or as many as six. Groups default to one contact each, with the first group containing contact one, the second group containing contact two, and so on. In situations where multiple contacts belong to a group the percentages of contribution for each group are entered into their respective locations. This controls the distribution of current and thus sets the field of neural activation between two or more contacts of the cuff electrode 764. Below the Global IPG Parameters window may be the Electrode window, and if a contact is enabled, its current settings may be displayed as will be the effect it causes. Manual entries into the fields of this section are allowed, but changes to amplitude will be corrected to the nearest actual amplitude possible. This may be required because the output of the current sources in the IPG 1370 is logarithmic, not linear, so manual selection of amplitude is not as easy as it would seem. The increment and decrement function of the Titration screen automatically takes this non-linearity of the current sources into effect and uses the calibration data of the IPG 1370 to display actual currents.

The main section to the right may contain a Status Window again, and two sections that control communication between the RCC 2272 and IPG 1370 and File Operations. In the Communication section, stimulation parameters may be read from or sent to the IPG 1370. In the File Operations section, stimulation parameters may be read from or written to records in the database. IPG 1370 event logs may be retrieved from the IPG 1370 and saved to files as well. In one embodiment, the bottom portion of the Manual Parameter Control screen allows the viewing of the various logs that are collected by the IPG 1370, including electrode impedances, battery charging operations, battery use profiles, and IPG events, both expected and unexpected (but anticipated) events.

RCC Functions Screen

Figure 33:
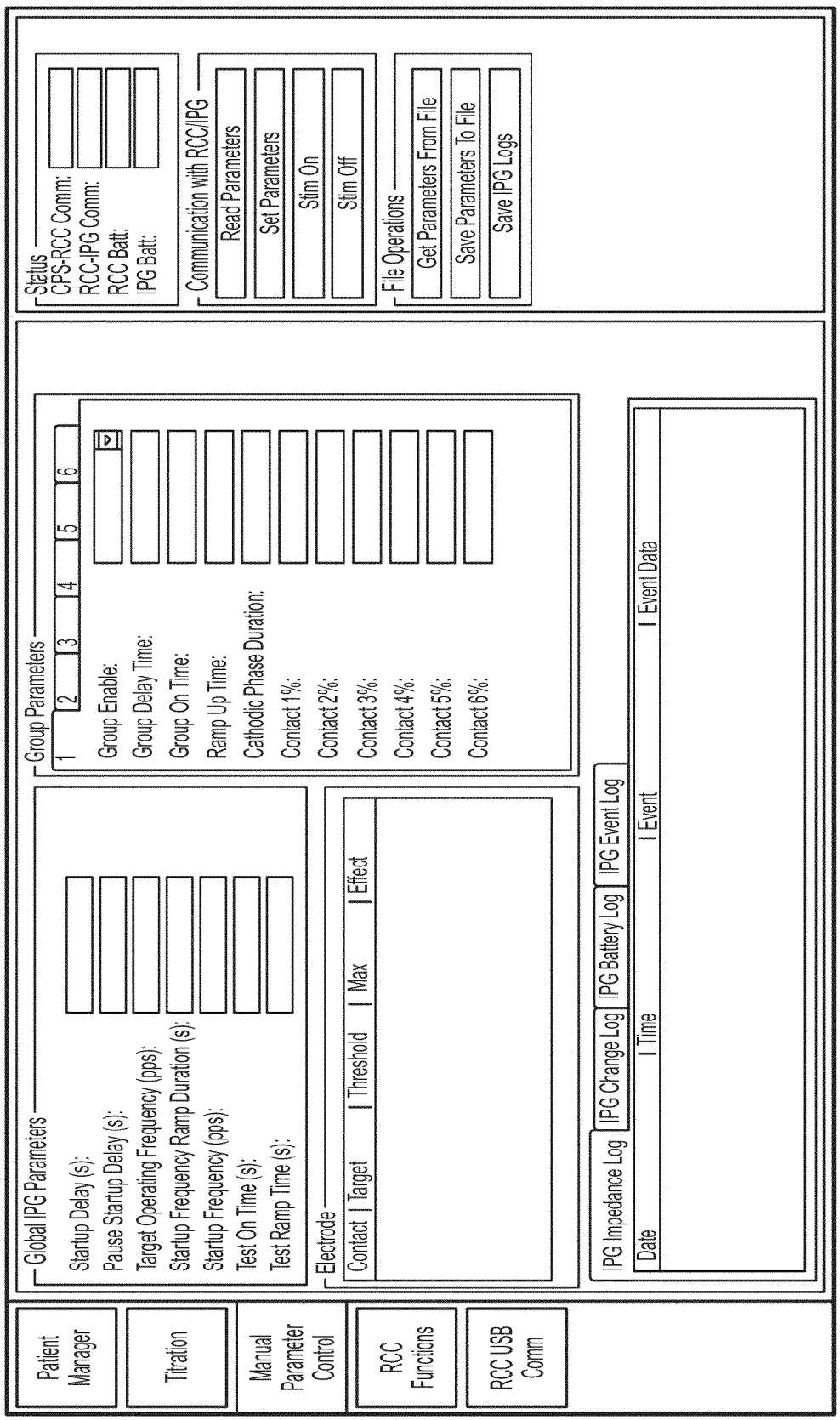
FIG. 33 is a depiction of the aCM Manual Parameter Control Screen.

The RCC Functions Screen, an exemplary embodiment being depicted in FIG. 33 may allow the aCM to fully simulate the operation of the RCC 2272 while the RCC 2272 is connected to the aCM and is in pass-through mode. Indicators for the LEDs and regions on the screen that can be clicked like the buttons of the RCC 2272 switches allow full operation of the system as if the aCM were not connected. This may be useful when the aCM user is located at a distance from the RCC 2272 (such as might occur in the OR, sleep laboratory, or other remote location).

RCC USB Comm Screen

Figure 34:
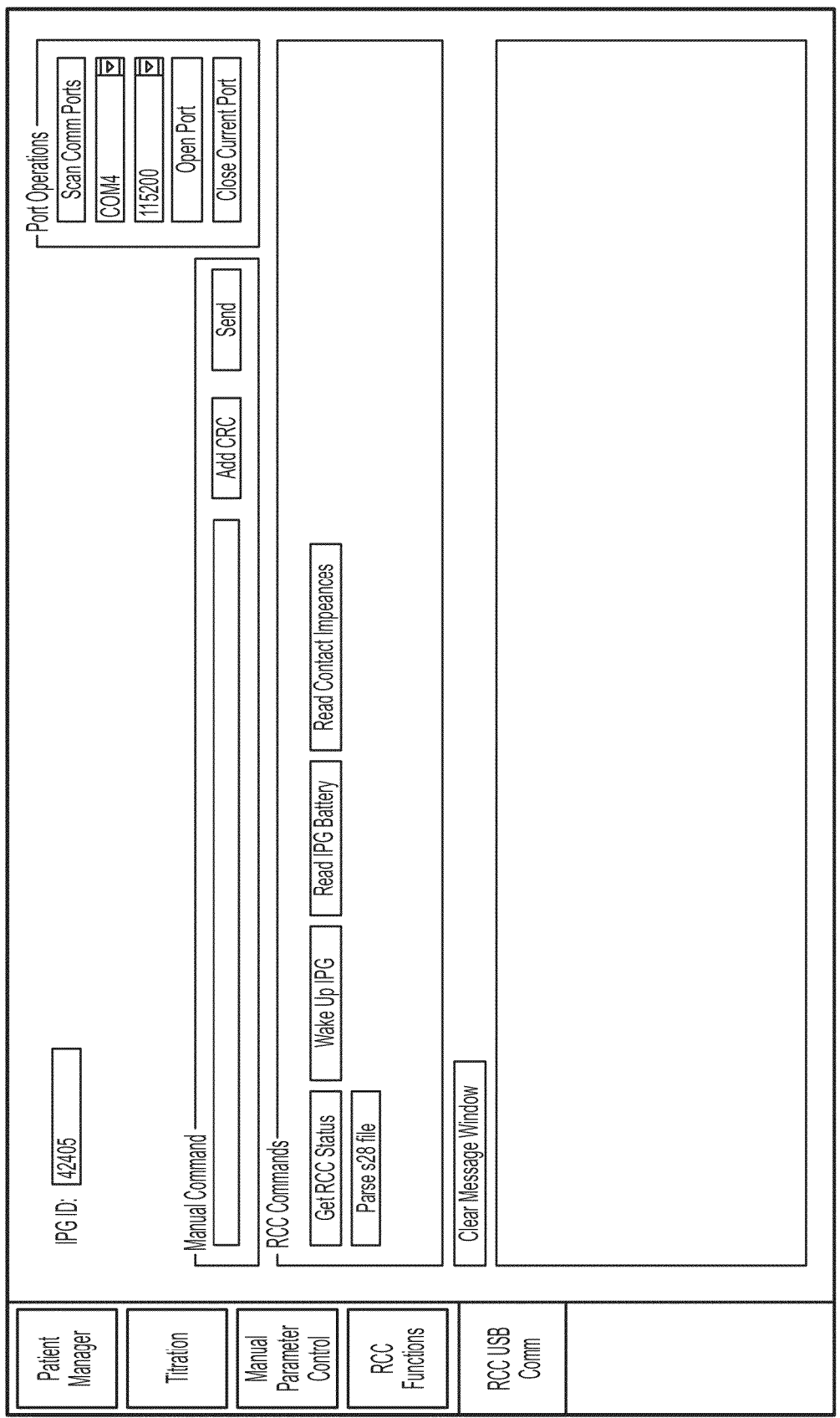
FIG. 34 is a depiction of the aCM RCC USB Comm Screen.

The RCC USB Comm Screen, an exemplary embodiment being depicted in FIG. 34 may be a special screen that is typically only enabled for use by an engineer. The RCC USB Comm Screen may allow complete observation of communications between aCM and RCC 2272 and between the RCC 2272 and an IPG 1370. In one embodiment, manual formulation of telemetry commands is supported, as well as computation of CRC codes to be included in command packets. Port operations on the aCM are also visible and controllable in this screen. This may be particularly useful when certain PC platforms and versions of Windows are used with USB devices and connect and disconnect of USB cables causes re-assignment of ports to occur, sometimes without obvious rhyme or reason to the user.

Operation of System

In one embodiment, operation of the system includes five phases of operation: Manufacturing, Implantation, Titration, PSG, Follow-up, and Patient use phases. During the Manufacturing phase, the IPG 1370 and RCC 2272 may be programmed, tested, calibrated, and stocked for shipment and implantation. The JTAG interface of the PCB assemblies of the IPG 1370 (before singulation and encapsulation into its hermetic enclosure) and RCC 2272 may allow full programming and test to occur. Post singulation and encapsulation of the IPG PCB assemblies may require use of the secondary boot loader described previously to change program contents of the IPG 1370. In one embodiment, following programming and testing of an IPG 1370, it may be placed into a low power consumption mode in which the battery is disconnected from the circuit and only very low current consumption occurs due to the single active component remaining connected to the IPG battery, a battery monitoring circuit. This may allow an IPG 1370 to be fully charged, then disconnected from its battery and stored for a long period of time with little loss of battery energy. In the programming environment a computer with a JTAG interface may be connected to the various assemblies and code may be programmed into the devices. In the sealed IPG 1370, the programming system may utilize a stock RCC 2272 to transfer commands over the MICS telemetry band to the IPG 1370.

Figure 35:
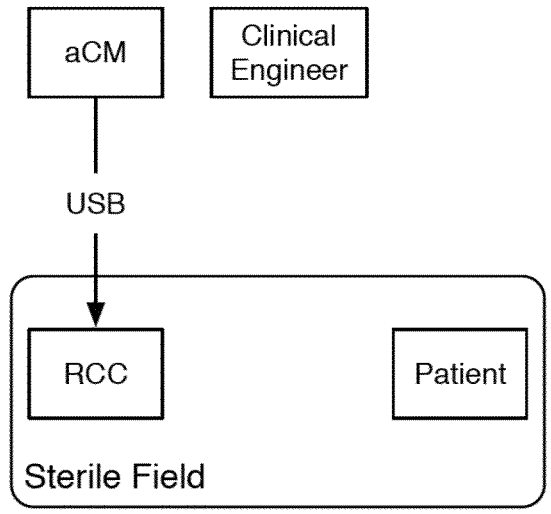
FIG. 35 is a block diagram of the Implantation Use Model.

The Implantation phase, an example being depicted in FIG. 35, occurs when the patient is surgically implanted with the electrode and IPG 1370. In this environment, the IPG 1370 and electrode may be contained in sterile packaging ready for use within the sterile field of the operating room. Prior to surgery, an RCC 2272 may be placed on the operating table next to the patient, and a long USB mini-B cable may be connected to the RCC 2272 and crosses the border of the sterile field and may be passed to the clinical engineer and aCM. During the implantation the IPG 1370 and electrode may be briefly tested for impedance and threshold stimulation levels for all of the six contacts of the cuff electrode 764.

Figure 36:
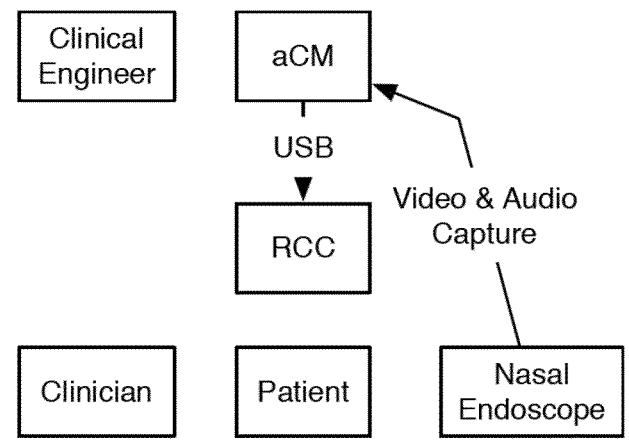
FIG. 36 is a block diagram of the Titration Phase Use Model.
Figure 37:
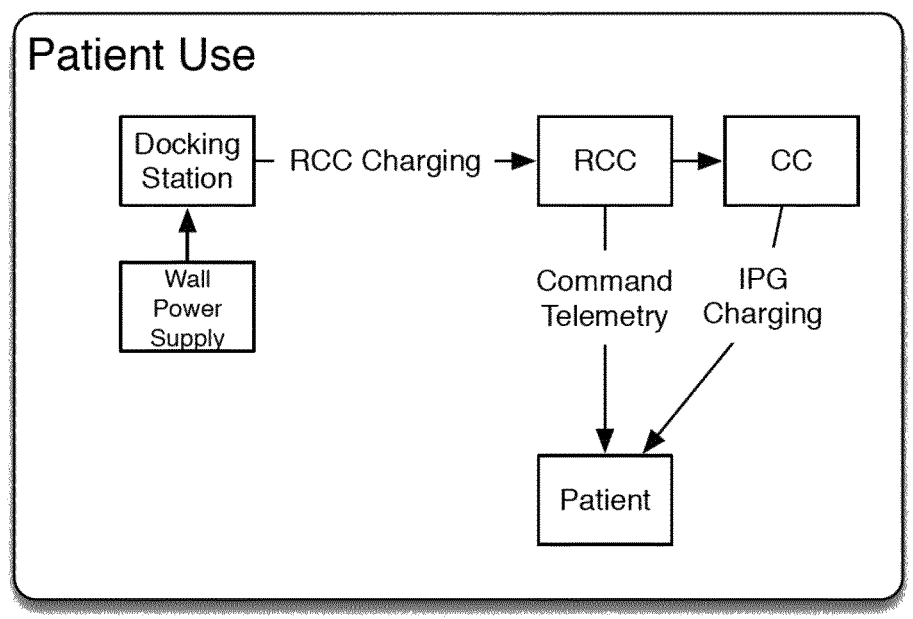
FIG. 37 is a block diagram of the Patient Use Model.

The Titration phase, an example being depicted in FIG. 36 may be the main programming phase for the system. In this phase, all contacts may be tested to determine their threshold, target and maximum stimulation levels, what the actions of each of the electrode contacts elicits, testing of contact pairs or tripoles, etc., if warranted, and assignment of groups that may be used during the Patient Use phase. The Follow-up phase may be essentially just like the Titration phase, except that changes may be made to pre-existing stimulation parameters so that improvements in stimulation effect may be obtained or corrections due to contact or wire failures or other causes can be mitigated. The Patient Use phase, an example being depicted in FIG. 37 may be the main use of the system and encompasses the stimulation therapy and maintenance of the OSA system. The detailed operations of the OSA system are described in further detail below.

On/Off Button Pressed

Figure 38:
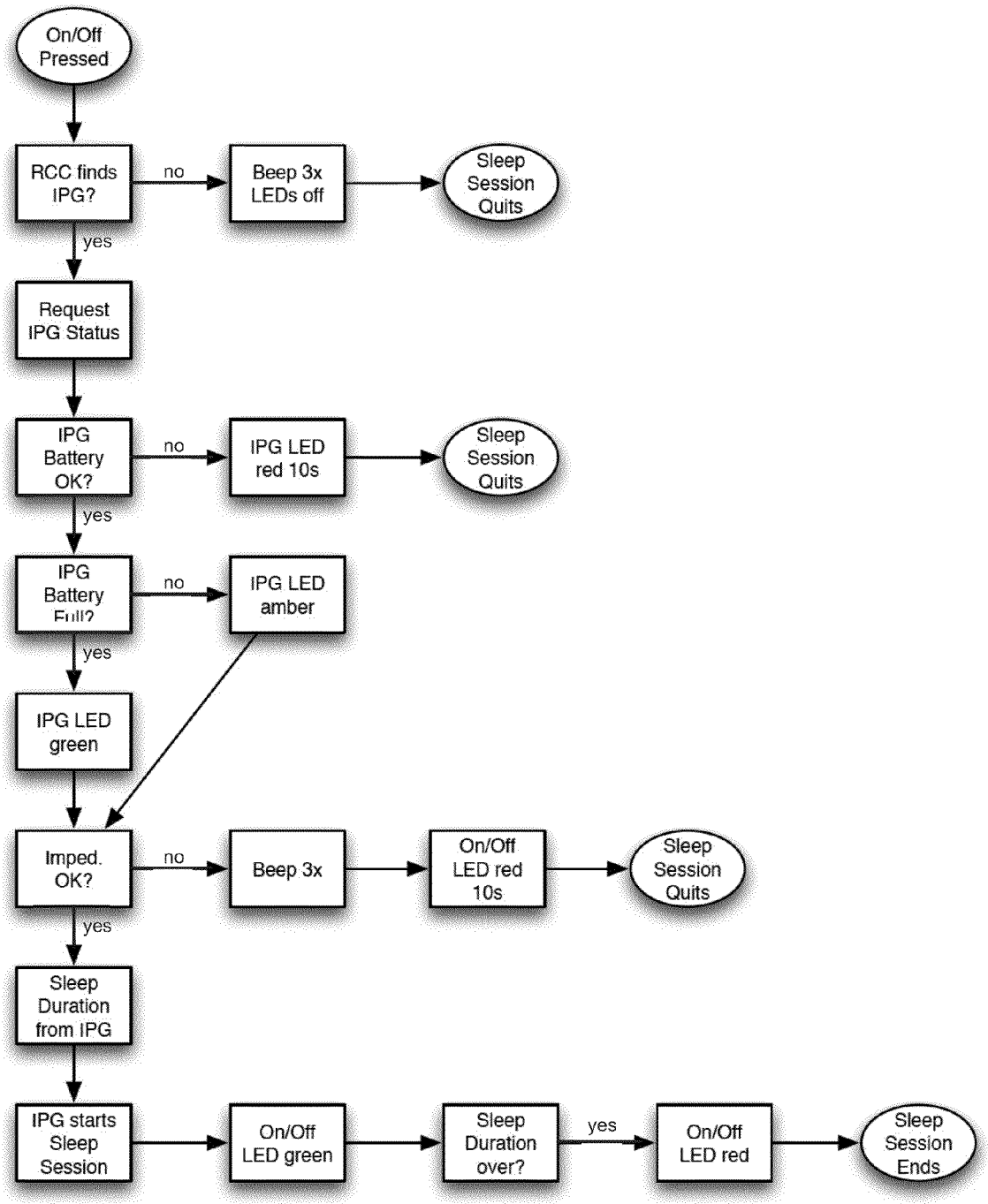
FIG. 38 is a flow diagram for the On/Off Key of the RCC

The On/Off button on the RCC 2272 may be used to start or stop a sleep therapy session. The procedure associated with the On/Off key operation is represented in FIG. 38. In one embodiment, the patient removes the RCC 2272 from the docking station 5378 and presses the On/Off key. The RCC 2272, which may have been in a low power consumption mode, awakens and begins to search for its assigned IPG 1370. The RCC 2272 may send telemetry requests through its MICS telemetry channel for a fixed period of time. If at the end of this time window it has not found its IPG 1370, it may generate beeps, indicate a failure to link to its IPG 1370 and end the sleep therapy session.

If the RCC 2272 is able to link to the IPG 1370, it may then send a request for the IPG 1370 to send its status information, including state of charge for the IPG battery, electrode impedance information, as well as error flags and other information that is relevant prior to starting a sleep therapy session. The RCC 2272 may set LEDs indicating the status of the IPG 1370. If there is sufficient charge in the battery to start a sleep session, and if all of the electrodes programmed to operate are within operational boundaries then the IPG 1370 may be instructed to start a sleep therapy session. The IPG 1370 may send the RCC 2272 a data packet with the duration of the sleep session, which the RCC 2272 may use to control the indicator LED on its front panel showing the status of the IPG 1370. The RCC 2272 may then go to sleep in a low power mode until the next time that the patient presses a key. The IPG 1370 may go about the process of sleep therapy, described below.

Charge Button Pressed

Figure 39:
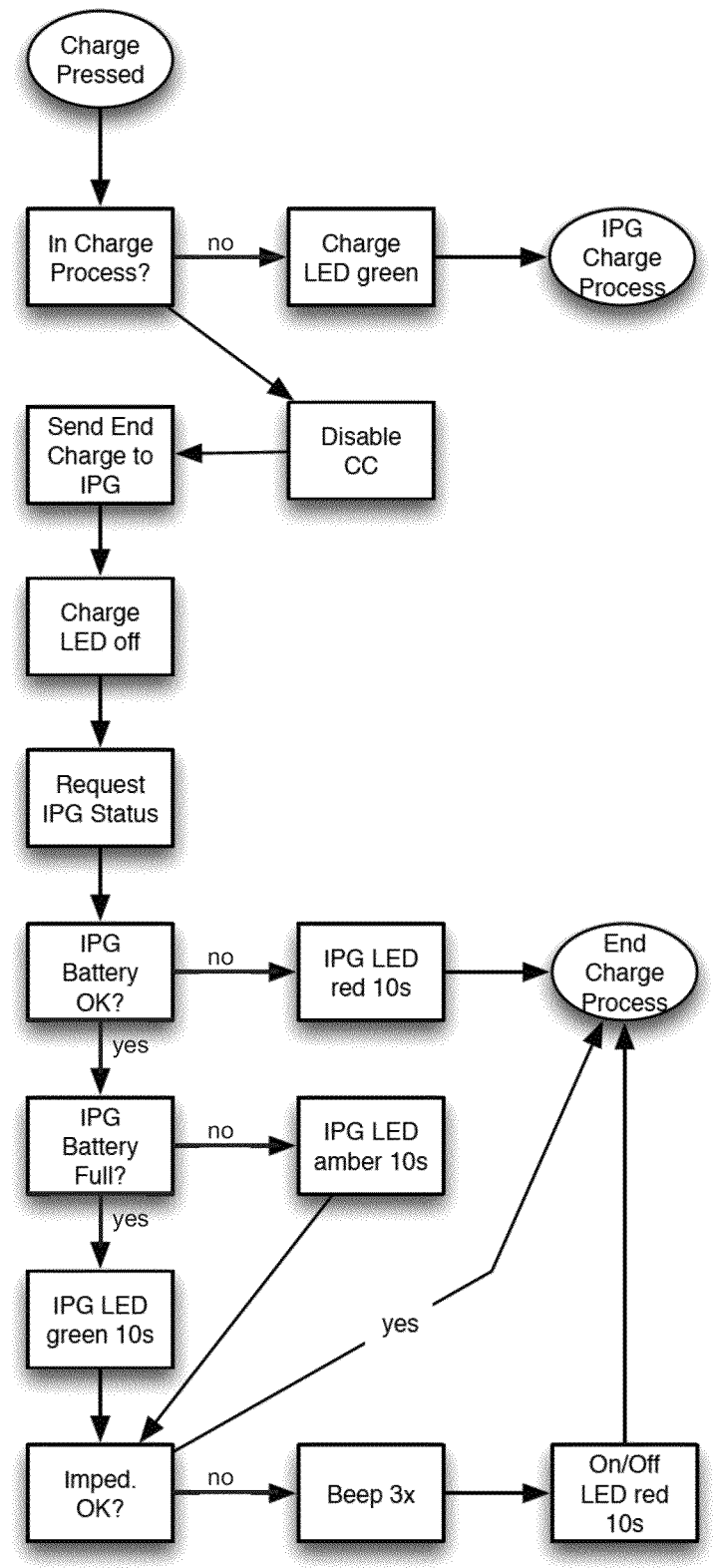
FIG. 39 is a flow diagram for the Charge Key of the RCC.

The Charge Key may initiate the process of charging the IPG 1370, an example being depicted in FIG. 39. In this process, the patient may connect a charger coil (CC) to the RCC 2272 and places the CC over the IPG 1370 to transfer energy from the RCC 2272 to the IPG 1370. The RCC 2272 may be able to detect when the CC is attached because of a loop-back connection within the connector or by monitoring current consumption. In one embodiment, the CC is held in place over the IPG 1370 because both devices could contain magnets which could help to hold and align the CC optimally over the IPG 1370. The RCC 2272 may be able to determine how well the coil is aligned over the IPG 1370 by monitoring the current consumption in the CC. By this same method of monitoring current and by changing the current in the CC a secondary telemetry channel may be available in case of problems with the primary MICS telemetry channel.

An exemplary sequence of events in the Charge process may be as follows. The patient presses the Charge button and the RCC 2272 may come out of its low power mode. If the charge process is already in place, the intent of the patient may be deduced to be to end the charge process. The RCC 2272 may stop the charge process and disable the CC and establish a MICS communication link with the IPG 1370. It then may then send an end of charge command to the IPG 1370, turn off the Charge LED, and request the IPG 1370 status. It may then display the IPG battery status, and assess the impedance data. If the impedances are acceptable (within an acceptable range for current controlled pulses to be generated), the charge process may end. If the impedances are not within an acceptable range, then the On/Off LED may be set to red, the RCC 2272 may generate beeps and the charge process may end. If the charge process was not already set, the RCC 2272 may set the Charge LED to green and start the IPG Charge process, described below.

Test Button Pressed

Figure 40:
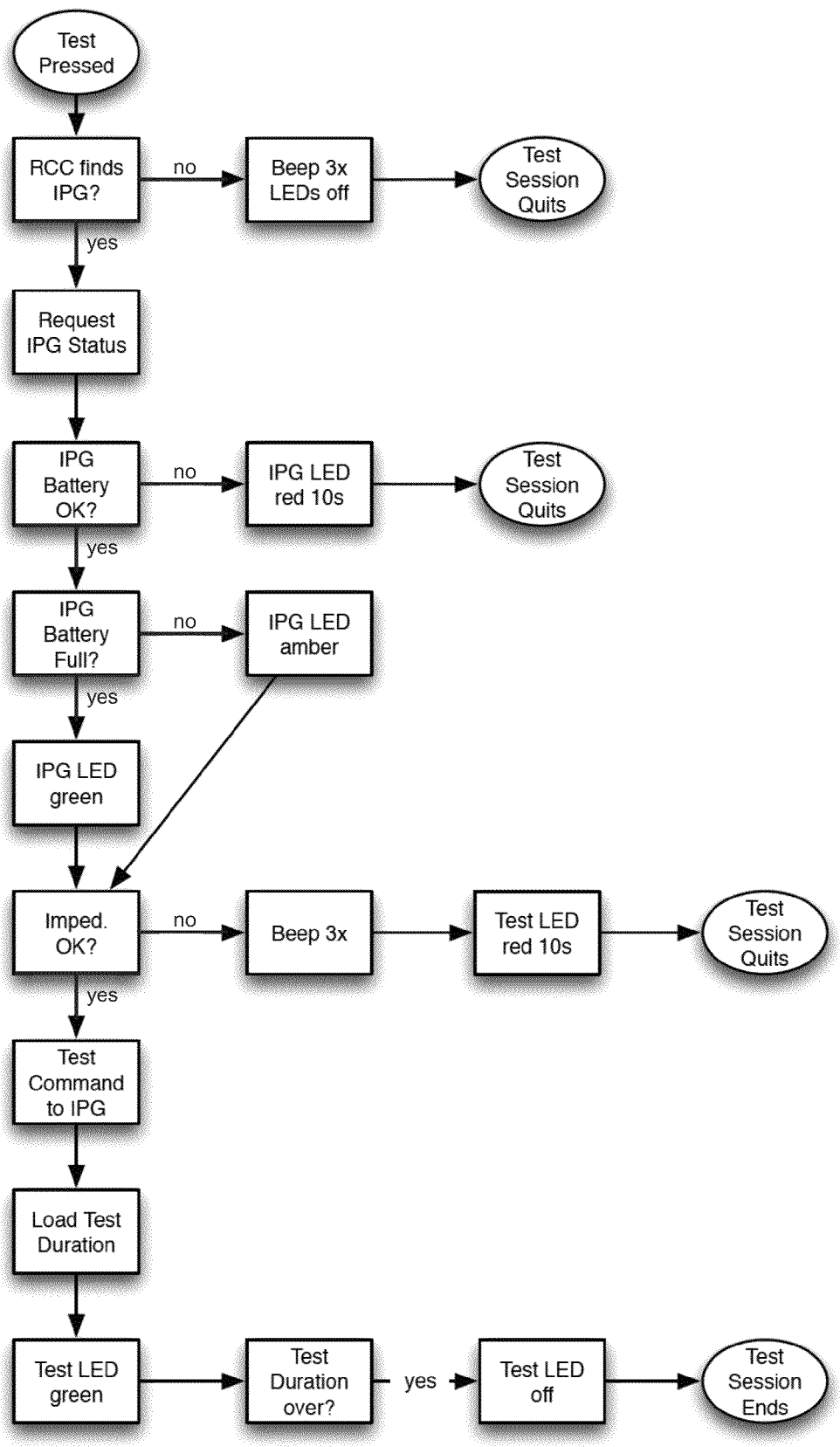
FIG. 40 is a flow diagram for the Test Key of the RCC.

The Test button may initiate a process to demonstrate to the patient a brief stimulation session that is representative of the stimulation that will be applied during the sleep session. Since the stimulation during the sleep session may not actually begin to deliver stimulation pulses while the patient is awake, it may sometimes be desirable for the patient to verify that the stimulation system actually will work as expected, or to verify that the stimulation parameters will be comfortable during the sleep therapy. The test process may be identical to a sleep therapy session except for the duration of the stimulation periods, the on and off times, and the ramp times for all of the groups. In one embodiment, stimulation starts immediately upon initiation of the test process and ends after all of the groups have gone through their ramp up, plateau, and ramp down phases, or when the test button is pressed again to stop the test process immediately. The sequence of events in the Test process is shown in FIG. 40. After the Test key is pressed, the RCC 2272 may come out of low power mode and seeks the IPG 1370. If the RCC 2272 cannot find the IPG 1370, the RCC 2272 may generate beeps, set its LEDs and the test session quits. If the IPG 1370 is found, the RCC 2272 may request the IPG 1370 status. The RCC 2272 may then set the IPG 1370 battery status LEDs appropriately. If the Battery is sufficiently charged, the RCC 2272 may then continue, otherwise the test process could quit. If the impedance is within acceptable limits for the active groups then the test command may be sent to the IPG 1370, if not, the RCC 2272 may generate beeps, set the Test LED to red and the test session may end.

Pause Button Pressed

Figure 41:
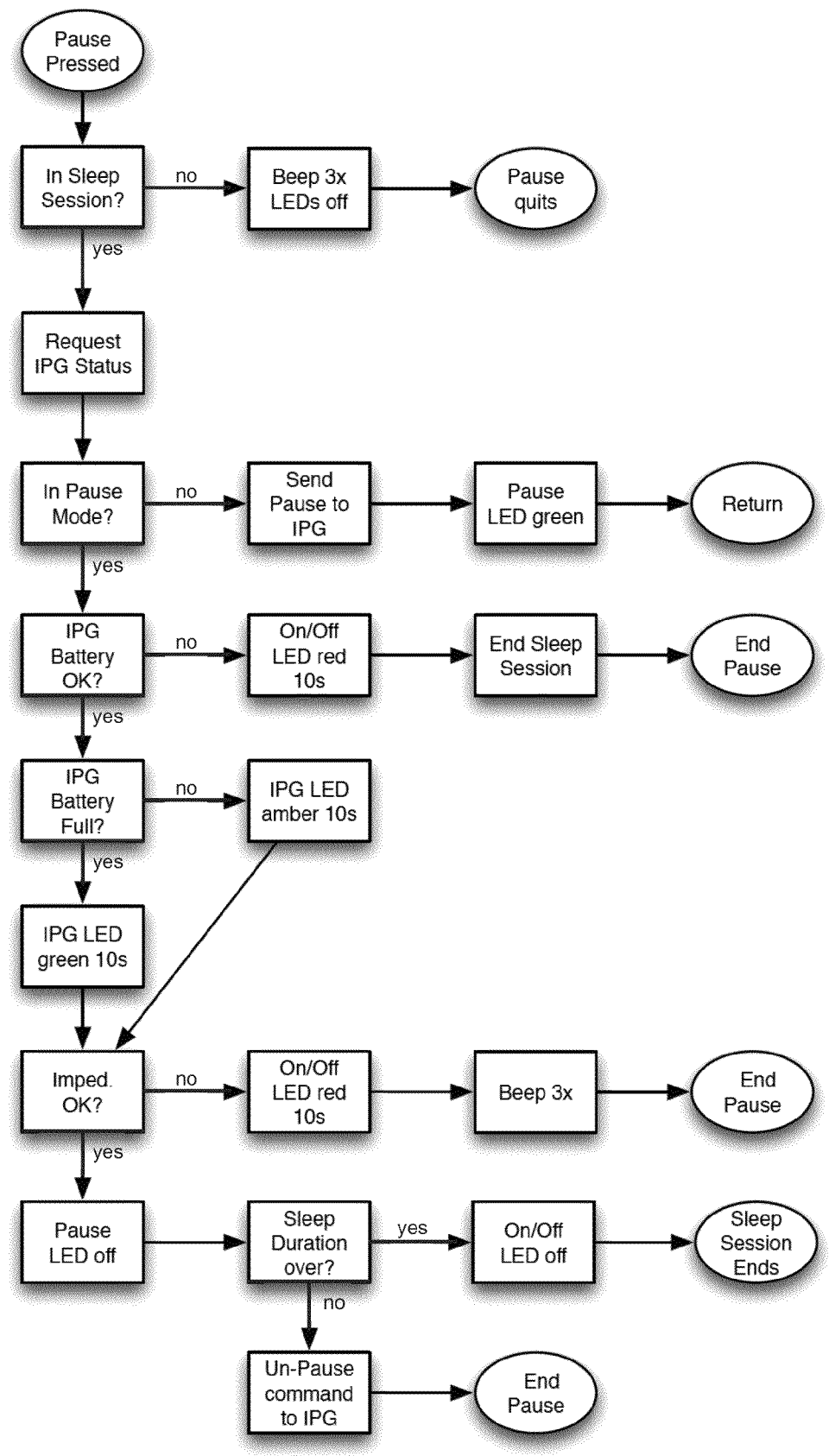
FIG. 41 is a flow diagram for the Pause Key of the RCC.

The Pause button may stop a stimulation session for a brief period to allow the patient to wake up and go to the bathroom, etc. An exemplary pause process is outlined in FIG. 41. The key may only valid during a sleep therapy session and may be ignored if the IPG 1370 is not in this mode. An exemplary RCC 2272 pause process may be as follows: the patient presses the Pause key. If the IPG 1370 is not in a sleep session, the RCC 2272 beeps, turns off LEDs and returns to low power mode. If the IPG 1370 is in a sleep session the RCC 2272 attempts to link to the IPG 1370 and requests the status of the IPG 1370. If the IPG 1370 is not already paused, the RCC 2272 sends a pause command to the IPG 1370, sets the Pause LED green, and returns to low power mode. If the IPG 1370 was already in pause mode, the RCC 2272 may look at the IPG battery. If the battery is low, the RCC 2272 may end the sleep session and set the IPG LED to red and return to low power mode. If the battery is full the RCC 2272 may set the IPG LED to green, otherwise the RCC 2272 may set the battery LED to amber. The RCC 2272 may then check the impedance. If the impedance is not OK the RCC 2272 may set the On/Off LED to red, generate beeps, and return to low power mode. If the impedance is OK, then the RCC 2272 may turn the Pause LED off. The RCC 2272 may then check to see if the sleep duration is over. If so, it may set the On/Off LED to off and end the sleep session. If the sleep session is not over the RCC 2272 may send a command to the IPG 1370 to finish the pause and the RCC 2272 may go back to low power mode.

IPG Pause Process

Figure 42:
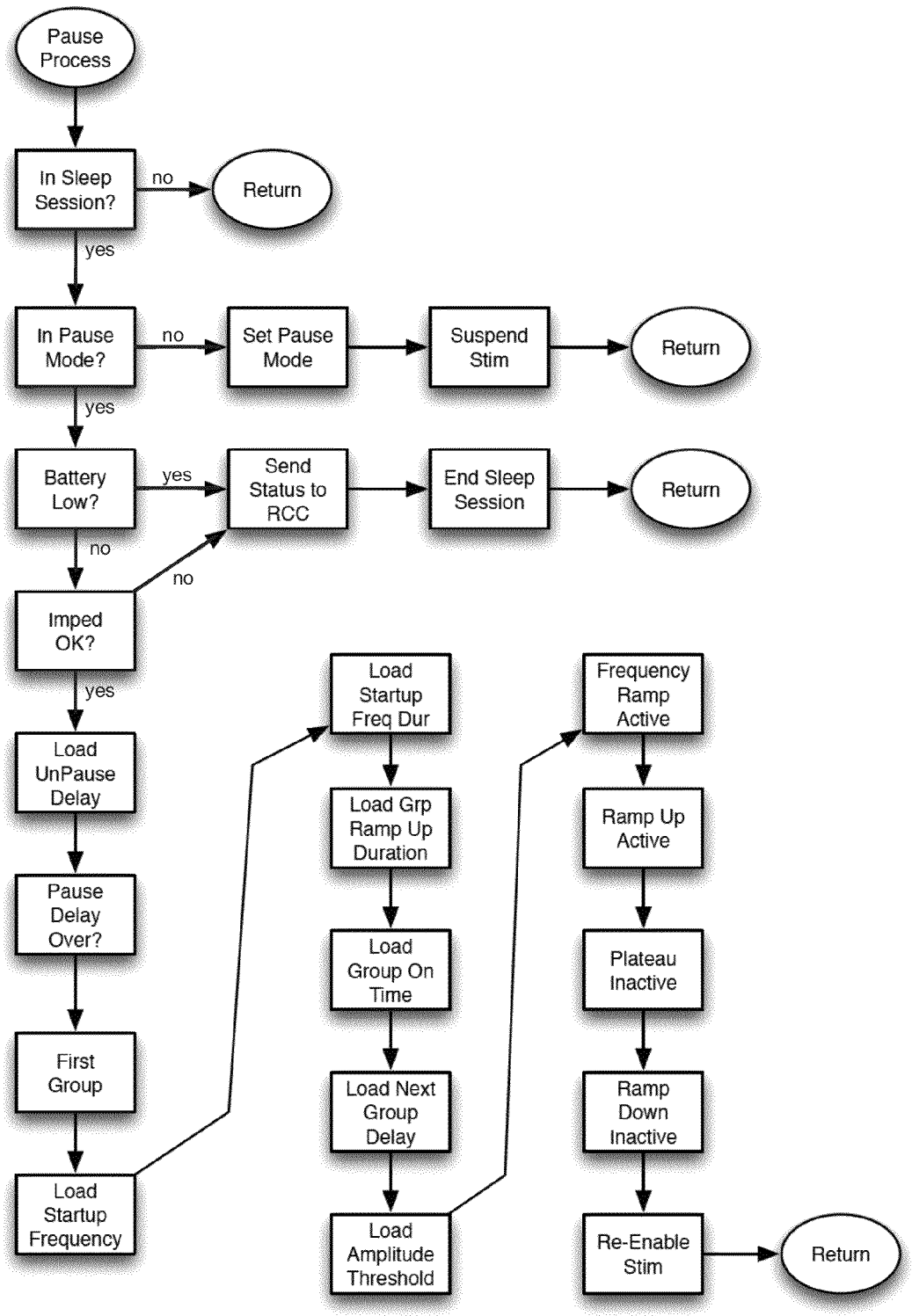
FIG. 42 is a flow diagram for the IPG Pause Process.

The IPG 1370 Pause Process may occur upon command from the RCC 2272, and an example is depicted in FIG. 42. An exemplary IPG Pause process may proceed as follows: If the IPG 1370 is not in a sleep session the IPG 1370 may return and go back into low power mode. If the IPG 1370 is not in the pause mode the IPG 1370 may enter the pause mode, suspend stimulation and return to its low power mode. If the IPG 1370 is in the pause mode the IPG 1370 may start to return to stimulation mode, if several conditions are met. First the IPG 1370 may check to see if the battery is low, and if is the battery is low, the IPG 1370 may send status information to the RCC 2272 and end the sleep session. If the battery is not low, the IPG 1370 may check impedances. If the impedances are not within an acceptable range, then the IPG 1370 may send status information to the RCC 2272 and end the sleep session. If the impedances are within an acceptable range, then the IPG 1370 may load the UnPause delay (similar to the sleep session delay, but typically less time because most patients will fall back to sleep faster than at the beginning of the sleep session), wait for the delay to be complete, and then the IPG 1370 may start setting up the first group for stimulation. This may involve setting up the startup frequency delay, the startup frequency duration, the group one ramp up duration, the group one on time, the next group delay time, the amplitude threshold, setting the frequency ramp to active, setting the ramp to active, setting the plateau phase to inactive, setting the ramp down to inactive, and enabling stimulation. The IPG 1370 then may then return to the low power sleep state.

IPG Charge Process

Figure 43:
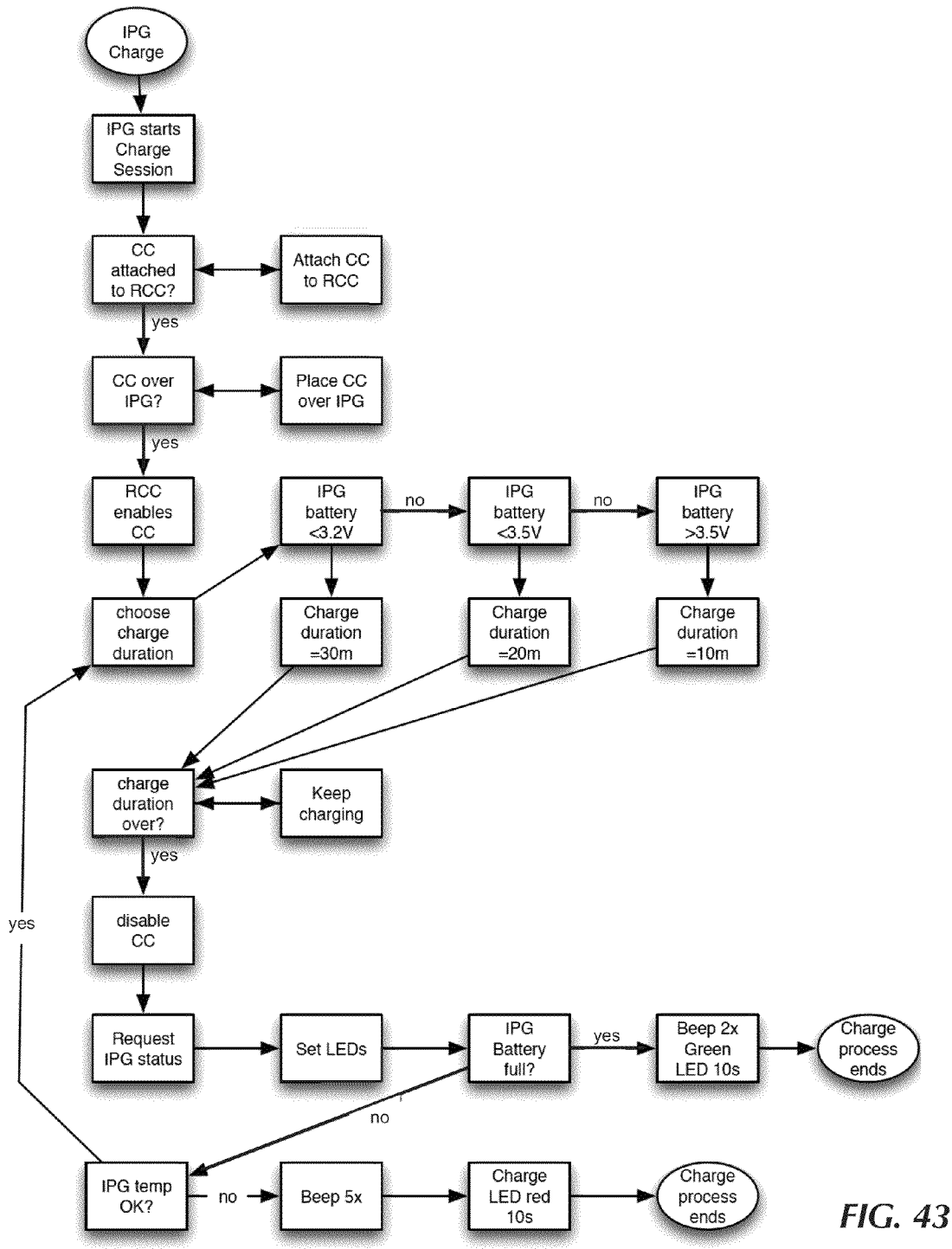
FIG. 43 is a flow diagram for the IPG Charge Process.

The IPG Charge Process may be initiated by the RCC 2272, as described above, and an example is depicted in FIG. 43. In one embodiment, the IPG 1370 and the CC are coupled, the RCC 2272 is close enough for MICS telemetry, the RCC 2272 is completely charged and able to transfer power to the IPG 1370, and all other relevant systems are functional. The RCC 2272 and IPG 1370 may share in the responsibility of checking that the CC is attached to the RCC 2272 and that the CC is aligned properly over the IPG 1370. With everything in place, the RCC 2272 may then enable the CC. The RCC 2272 may then choose a charge duration based upon the state of charge of the IPG battery. If the battery voltage is less than a certain level the RCC 2272 may set the charge duration to 30 minutes. If the battery voltage is less than a slightly higher level the RCC 2272 may set the charge duration to 20 minutes. Otherwise the RCC 2272 may set the charge duration to 10 minutes. The RCC 2272 may then wait for the charge duration to be over, after which the RCC 2272 may disable the CC and request the status from the IPG 1370 and set its LEDs accordingly. If the battery is full, the RCC 2272 may generate beeps, set Charge LED green for 10 seconds and end the charge process. If not, the RCC 2272 may check the temperature of the IPG 1370. The temperature of the IPG 1370 would be checked to see if a potentially dangerous or detrimental condition exists because of the charging process and the effect that can have on the chemistry of the rechargeable battery. If the temperature of the IPG 1370 is acceptable the RCC 2272 may then go back to choose the charge duration and continue the charge process. If the temperature is not acceptable, the RCC 2272 may generate beeps, set the Charge LED to red for 10 seconds, and end the charge process. At the end of a fixed duration the RCC 2272 may terminate the charge session regardless of the state of charge of the IPG battery.

Sleep Session Process

Figure 44:
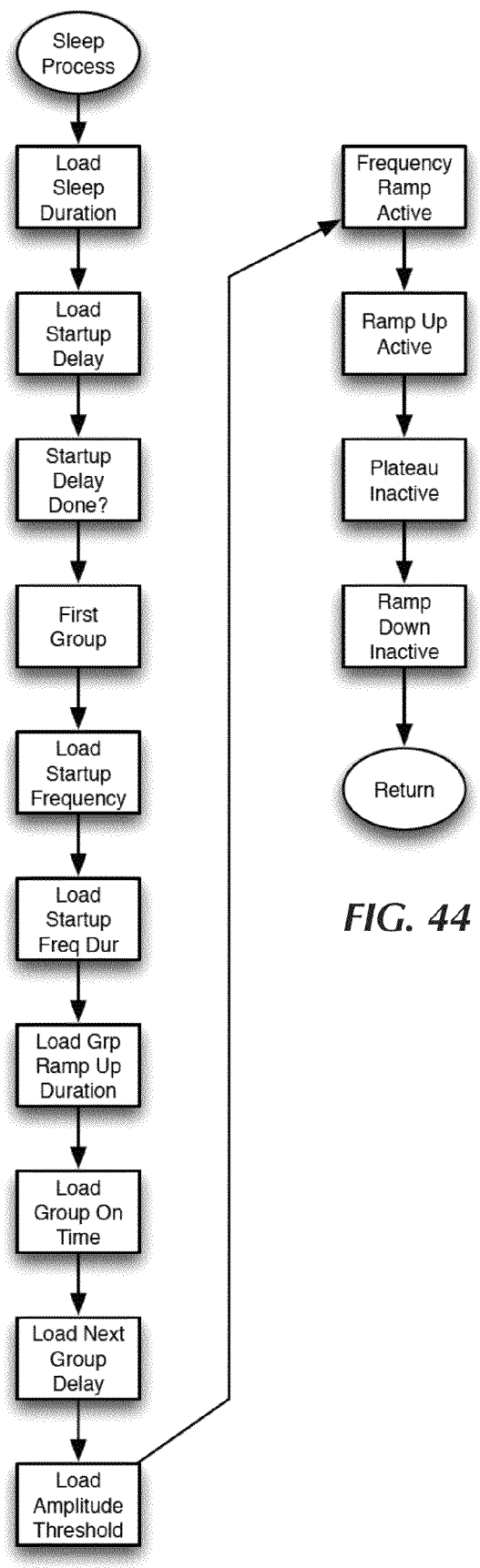
FIG. 44 is a flow diagram for the Sleep Process.

An exemplary sleep Session process is depicted in FIG. 44. The IPG 1370 may load the sleep duration counter, load the startup delay and then wait for the startup delay to be completed. The IPG 1370 may then prepare the first stimulation group. The startup frequency may then be loaded, the startup frequency duration may be loaded, the first group ramp duration may be loaded, the group on time may be loaded, the next group delay may be loaded, the amplitude threshold(s) may be loaded, the frequency ramp may be set to active, the ramp up may set to active, the plateau phase may be set to inactive, the ramp down may be set to inactive, and the IPG 1370 may return to the low power sleep state.

Frequency Tick Process

The Frequency Tick Process may be the main event coordinating the delivery of stimulation pulses. Since the frequency tick interrupt process represents the frequency that pulses occur during stimulation, the timer interrupt associated with this event may be therefore the event which triggers the delivery of a set of pulses for all of the active contacts and the advancement from one phase to another for a group, or the transition between groups. Typically, it is expected that when a group is at its plateau or target level it will be the only group active, but during the ramp up and ramp down times there may be two or more groups active, depending upon the intent of the programming process.

Figure 45:
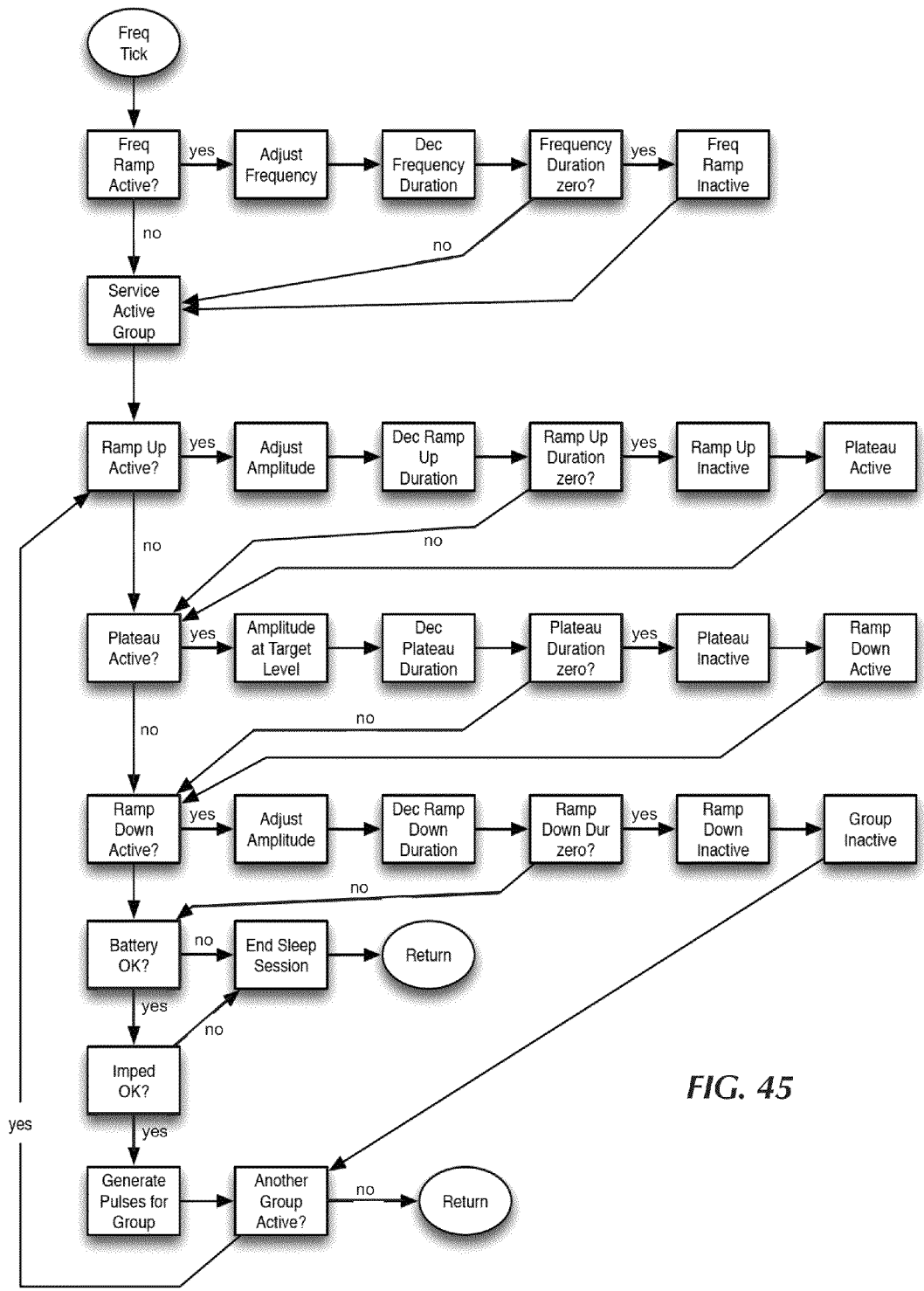
FIG. 45 is a flow diagram for the Frequency Tick Process.

The Frequency Tick Process is depicted in FIG. 45. The IPG 1370 first checks to see if the frequency ramp is active. If yes, the IPG 1370 may make any necessary changes in the timer value used to generate the frequency tick interrupt, thereby adjusting the frequency and then may decrement the frequency ramp duration. The IPG 1370 then checks to see if the frequency ramp duration is zero. If the frequency ramp duration is zero, the IPG 1370 may set the frequency ramp to inactive. The IPG 1370 may then begin to service the current active group. The IPG 1370 first checks to see if ramp up is active. If ramp up is active, the IPG 1370 may make any necessary adjustments to the group amplitude level. The IPG 1370 then may decrement the ramp duration and then checks to see if the ramp up duration is zero. If the ramp up duration is zero, the IPG 1370 may de-activate the ramp up phase and may activate the plateau phase. Next the IPG 1370 checks to see if the plateau phase is active. If the plateau phase is active, the IPG 1370 may set the amplitude at the target level, decrement the plateau duration, and check to see if the plateau duration is over. If the plateau duration is over, the IPG 1370 may deactivate the plateau phase and activate the ramp down phase. Next the IPG 1370 may check to see if the ramp down is active. If the ramp down is active the IPG 1370 may adjust the amplitude as needed, decrement the ramp down duration and check to see if the duration is zero. If the ramp down duration is zero, the IPG 1370 may inactivate the ramp down phase and deactivate the group.

Next the IPG 1370 may check to see if the battery is charged sufficiently. If the battery is not sufficiently charged, the IPG 1370 may end the sleep session and return to low power mode. Next the IPG 1370 may check the impedances. If the impedances are not within acceptable limits the IPG 1370 may end the sleep session and return to low power mode. Next the IPG 1370 may generate the pulses for the active group. Next the IPG 1370 may look to see if another group is active, and if so begins to service that group as indicated above. If not, the IPG 1370 may return to low power mode.

Next Group Tick Process

Figure 46:
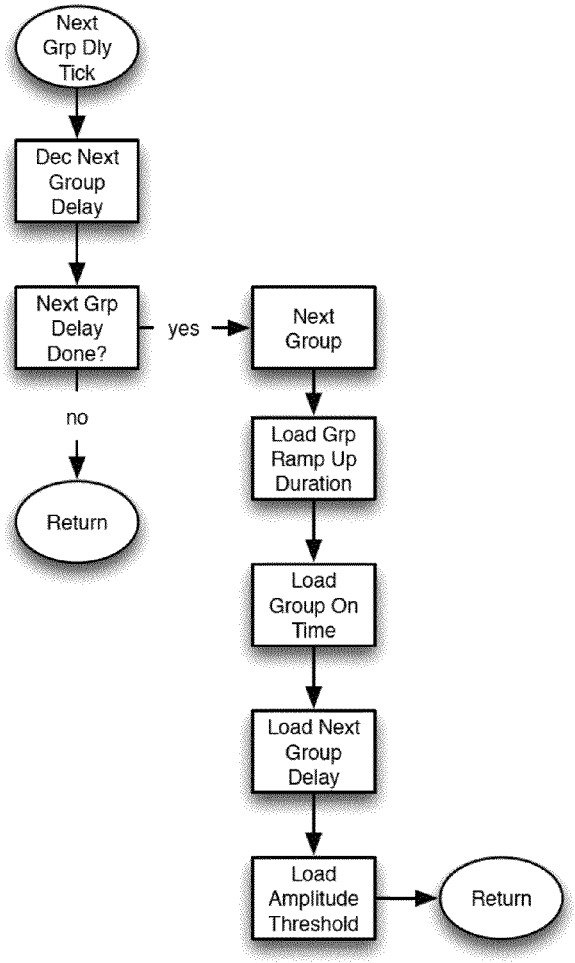
FIG. 46 is a flow diagram for the Next Group Delay Tick Process.

The Next Group Tick Process, depicted in FIG. 46 is responsible for activating the next group in the stimulation process. When the timer interrupt associated with the Next Group Delay Tick occurs, the IPG 1370 may decrement the next group delay counter, and check to see if the delay counter is zero. If the delay counter is zero, the IPG 1370 may activate the next group, load the ramp up duration, load the group on time, load the next group delay, and load the amplitude threshold and then return to low power mode. If the counter is not zero the IPG 1370 may simply return to the low power mode.

Sleep Duration Tick Process

Figure 47:
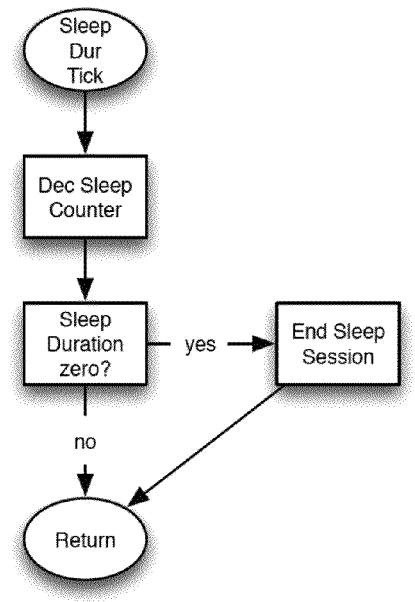
FIG. 47 is a flow diagram for the Sleep Duration Tick Process.

The Sleep Duration Tick Process, depicted in FIG. 47 is responsible for controlling the duration of the sleep therapy. The end of therapy may or may not coincide with the ramp down of the currently active group(s). In the process, upon the timer interrupt assigned to the sleep duration, the duration may be decremented, and if zero, the sleep session may be ended and the IPG 1370 may return to a low power mode. If the duration is not zero the IPG 1370 may simply return to the low power mode. It should be recalled that the sleep duration may be sent to the RCC 2272 by the IPG 1370 at the beginning of the sleep treatment session. The RCC 2272 may independently count down its own copy of this value, and when this count reaches zero the RCC 2272 may set the LEDs of the RCC 2272 accordingly. No communication between the IPG 1370 and RCC 2272 may need to occur at the end of the therapy session.

Group On Time Tick Process

Figure 48:
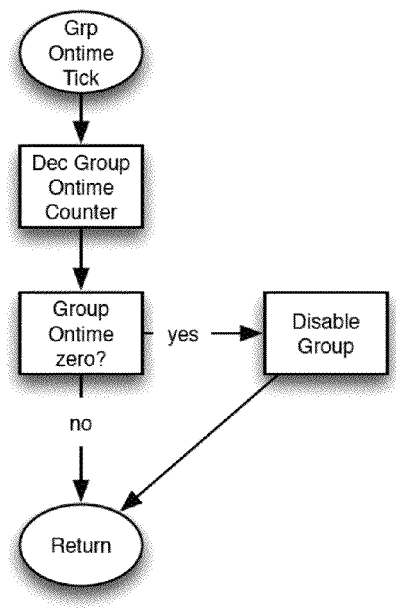
FIG. 48 is a flow diagram for the Group On Time Tick Process.

The Group On Time Tick Process is depicted in FIG. 48, and occurs when the timer interrupt associated with the group on time counter occurs. When this event occurs, the group on time may be decremented, and if the counter value reaches zero, the group may be disabled. This is a redundant process to the frequency tick in that both processes are able to control the duration of a group, but may be used in some instances when specific on times are desired that are different than the sum of the ramp up, plateau, and ramp down phases.

Impedance Measurement Process

Figure 49:
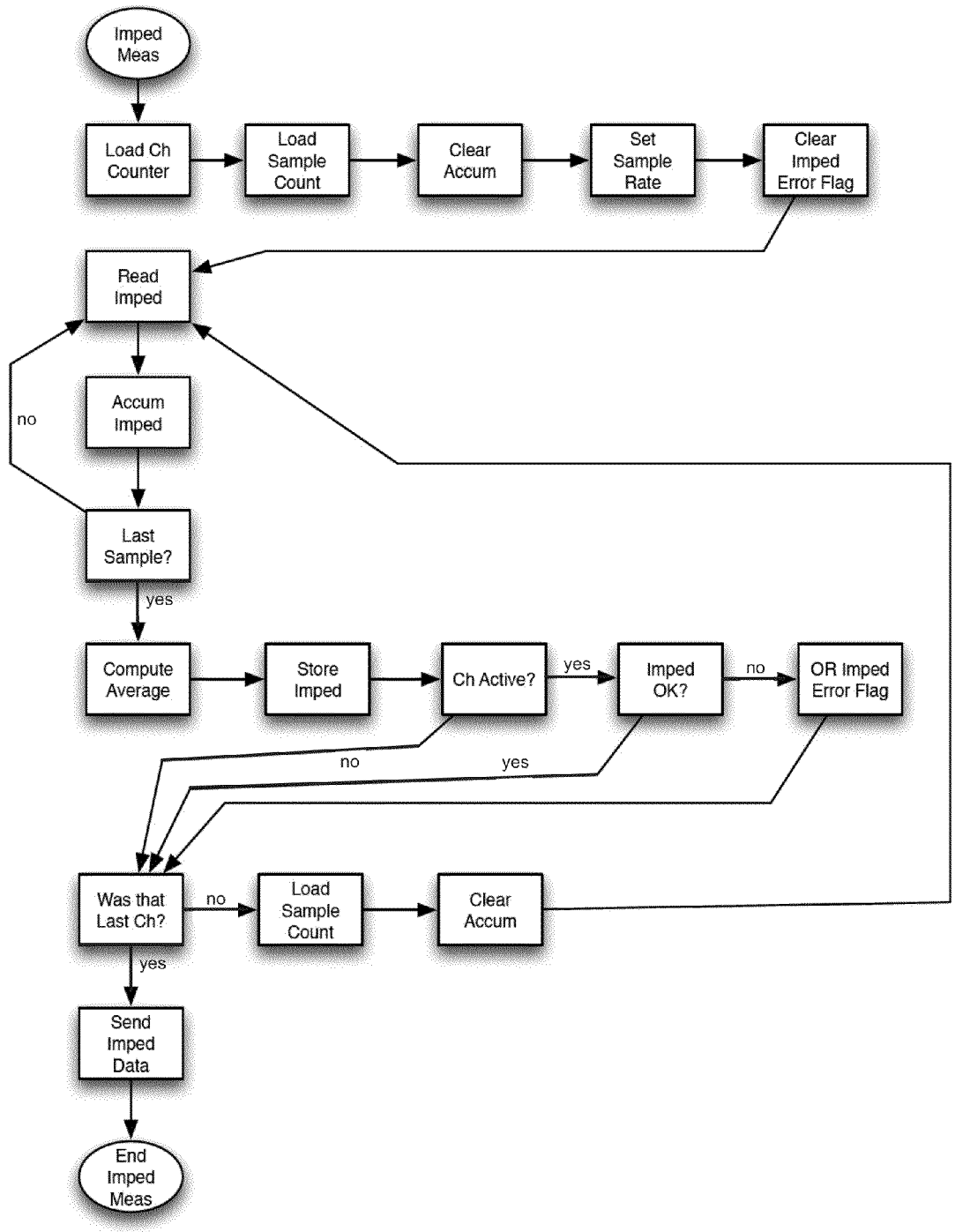
FIG. 49 is a flow diagram for the Impedance Measurement Process.

The Impedance Measurement Process is depicted in FIG. 49. Impedances may be regularly measured for all active contacts by measuring the voltage across the contact with respect to a reference, and knowing the current at which the stimulus pulse was generated, the impedance of the contact may be calculated. When impedances are detected on contacts that are programmed to participate in stimulation groups that fall outside of acceptable bounds, then stimulation from that point forward may be suspended. Upon noticing that stimulation cannot be started, the patient may be instructed to seek the advice of their physician, who could re-program their IPG 1370 to use other contacts, if possible, or to schedule revision surgery to correct the problem. An error flag associated with the measurement process may be updated and utilized for detection of out of bounds impedances for the stimulation process.

The impedance measurement process may begin with the initialization of several items. First, the total number of channels (contacts) may be loaded, the sample count loaded, the sample accumulator cleared, the sample rate set, and the impedance error flag may be cleared. The sampling process may then begin. The impedance for the first contact may be read and added to the accumulator. This may repeat until the last sample is read. Next an average value may be computed and stored in the impedance array for the contacts. If the channel/contact was active, the impedance may be checked for validity. If the impedance is outside the required bounds the impedance error flag may be logically OR'ed with the bit value for the channel. If that was not the last channel, the sample count may be re-loaded, the accumulator cleared, and the process begins for the next channel/contact. If the last contact/channel tested was the last channel/contact, the impedance data and error flag may be stored, the impedance data reported back to the RCC 2272, and the IPG 1370 may go into the low power mode.

Boot Loader Process

The Boot Loader Process (meaning the Secondary Boot Loader, and do not discuss the primary boot loader of the microcontroller) is depicted in FIG. 50, and may be the default program of the IPG 1370 processor—i.e., the Boot Loader Process is the program associated with the reset vector of the microcontroller of the IPG 1370. This boot loader may be required because the mask read-only-memory (ROM) boot loader of the microcontroller may only support a JTAG or similar interface to debug or program the flash memory of the microcontroller, and when the PCB assemblies are welded into the IPG 1370 case there may be no alternative method to re-program the IPG 1370 other than this secondary Boot Loader process.

The IPG 1370 can be placed into a power off state by being commanded to disconnect the battery from the IPG 1370 main circuitry. Once this command is executed, the only portion of the IPG 1370 circuitry being powered may be the battery monitor. This mode may be used to store the IPG 1370 in shelf mode, while it is awaiting shipment to a customer. The IPG 1370 may be taken out of the shelf mode by application of charger inductive power. This may supply power to the processor, which with its Power On Reset (POR) sequence, may vector to the Boot Loader. The Boot Loader may initialize the microcontroller and IPG 1370 resources, log an event that the Boot Loader has done so, open the MICS telemetry channel, load a Boot Message timeout counter, and wait for an incoming message from the RCC 2272. If no message is received before the timeout counter reaches zero, then the boot loader may check to see if there is a valid application image. If not, the Boot Loader may disconnect the battery and return to shelf mode. If a valid application image is available, then the Boot Loader may call the application. The use of a call instruction may allow a jump to any space in program memory without the expectation that a return from the application will occur.

Main Application Process

The Main Application is depicted in FIG. 51. The main application may be called by the Boot Loader, and may be responsible for initialization of system resources, servicing RCC 2272 telemetry commands, and monitoring system operation. The Main Application may proceed from power up by initializing the system, log a "begin main application" event, enable MICS wakeup interrupts and enter a low power mode. Upon receiving MICS wakeup interrupts the IPG 1370 may service the RCC 2272 command, load a MICS timeout window value, and await another command. When the timeout reaches zero, the main application may re-enable the MICS wakeup interrupt and may then go back into low power mode. The application may spend as much time as possible in low power mode to conserve battery energy for the convenience of the patient. All processes may essentially occur as needed by interrupt mechanisms. Interrupts, and thus processes, may be prioritized and masked or enabled as needed, to control the orderly operation of the IPG 1370. This may be extremely important to allow concurrent operations such as telemetry during stimulation, to allow changes in stimulation to be commanded by the RCC 2272 and the aCM. Without this interrupt concurrent system design there could be unacceptable latencies in certain events, which could manifest themselves as apparent lack of operational capability or delays to the patient or clinician.

System Programming

System programming and stimulation of the exemplary embodiments do not have to take into account the timing of respiration. When electrical stimulation is applied to a nerve bundle there are essentially two factors that determine which fibers within the bundle will be excited. The first is distance of the fiber to the contact—the closer a fiber is to the contact, the higher the current gradient and the more likely that the fiber will be excited. The second is the diameter of the fiber, which determines the voltage changes across the membrane and hence the likelihood of reaching the threshold of generating an action potential—the larger the diameter, the more likely that the fiber will be excited. At a particular current amplitude of sufficient duration, all of the fibers within a certain distance or diameter of the stimulation will be excited. As current amplitude increases, more fibers will be excited. Since each fiber is associated with a muscle fiber or fibers (jointly referred to as a motor unit), as more nerve fibers are excited, more muscle fibers are caused to contract, causing a gradation in force production or position as the stimulation current or phase duration is increased. The point at which this force is first generated is referred to as the motor threshold, and the point at which all of the fibers are all recruited is the maximum stimulation level. The comfort of this activity to the patient is often exceeded before this maximum level is attained, and it is important to determine the threshold level and the level at which the useful level of force or position is obtained at a level that is not uncomfortable for the patient. The point at which the optimal or best possible force or position is obtained is the target level.

In certain exemplary embodiments, system programming entails operatively connecting at least one electrode with a motor efferent located within a nerve (for example, the Hypoglossal nerve). This connection need not be a physical connection. The connection can be any connection known to those skilled in the art where the connection is sufficient to deliver a stimulus to the targeted motor efferent of the targeted nerve. Once the electrode is operatively connected with the targeted nerve, two or more electrode contacts are activated to determine their applicable stimulus thresholds (i.e., the threshold at which a desired response is achieved). The level of stimulation comfortable to the patient can also be measured. The contacts may also be assigned into functional groups that provide tongue motions that are beneficial in maintaining airway patency.

In certain exemplary embodiments, stimulation may be provided to the nerve using at least two functional groups. A functional group is defined as one or more electrode contacts (for example contacts 764a, 764b, 764c and 764d shown in FIGS. 7 and 8) that deliver a stimulus that results in a tongue movement that maintains an open airway. Each functional group may have a single contact, or may have multiple contacts. For example, a functional group with two contacts could be used to excite a population of nerve fibers that lie between two adjacent contacts. A non-limiting example of how stimulation from the functional group can be delivered is field or current steering, described in International Patent PCT/US2008/011599, incorporated by reference in its entirety. In another exemplary embodiment, two or more adjacent contacts may be used to focus the stimulation field to limit the area of excited neurons to a smaller area than what might be achieved with a single contact using a pulse generator case as a return contact. In another exemplary embodiment, two or more non-adjacent contacts may be used together to generate a useful response that is better than the response by the single contacts alone could produce. The table below shows various exemplary combinations of functional groups for an embodiment having six contacts numbered 1-6. A single contact can be a member of more than one functional group. For example, contact two could be in two different groups—one group made up of contact 1 and 2, and another group made up of contact 2 and 3. Exemplary contact groups are shown below.

a. Single Contact Groups: 1,2,3,4,5,6
b. Double Contact Groups: 1&2,2&3,3&4,4&5,5&6,6&1
c. Triple Contact Groups: 1&2&3,2&3&4,3&4&5,4&5&6,5&6&1,6&1&2
d. Non-Adjacent Contact Groups: 1&3, 2&4, 3&5, 4&6, 5&1, 1&3&5, 2&4&6, 3&5&1, 4&6&1, 1&2&4, etc.

FIG. 9 illustrates an exemplary stimulation strategy. FIG. 52 provides a more detailed view as the stimulation transitions from one active group to the next. As shown in FIG. 9, functional groups may be used to establish load sharing, amplitude ramping, and delayed start of stimulation to optimize the delivery of stimulation of the targeted nerve (the Hypoglossal nerve, for example). In the exemplary strategy of FIG. 9, stimulation is delayed after a patient begins a sleep session, allowing the patient to fall asleep before stimulation begins. Stimulation from each of the functional groups takes turns ramping up, holding the tongue in the desired position for a period of time that is sustainable without significant fatigue, before the next group starts and the previous group stops allowing muscle fibers associated with the previous group to relax, and which helps to prevent fatigue but which maintains desirable tongue position all the time.

The remaining effort in programming the two or more electrode contacts is to select electrode contacts and assign them to functional groups. During stimulation, only a single functional group will be on at a time or on at overlapping out of phase intervals, but a group may contain more than one contact. The effect of having more than one contact should additionally be tested to make sure that the sensation of the two contacts or groups on at the same time does not result in discomfort for the patient. Ostensibly, if a single contact results in good airway opening there is little reason to add another contact to the same targeted efferent. If the use of two contacts provides better opening then the pair should be tested together and assigned to the same group.

In certain embodiments, at least two functional groups are defined, so that the load of maintaining tongue position is shared, prolonging the time until fatigue sets in or preventing it altogether. Stimulation starts with the first group, which ramps up in amplitude to a target amplitude, stays at the target level for a pre-determined amount of time and then is replaced or overlapped by the next group. This repeats through one or more of the functional groups. The pattern may repeat beginning with the first functional group, but need not begin with the same functional group each time. In certain exemplary embodiments, the groups may be programmed to ramp up in amplitude while the previous group is still on and at the target level of the next group the first group would be programmed to terminate. This would maintain a constant, continuous level of stimulation that is shared amongst the programmed groups. The cycle repeats until the end of the sleep session.

The load of maintaining muscle tone and position is shared by all of the functional groups. In one embodiment, each contact is pulsed at different or overlapping intervals (FIGS. 10A and 10B). This prevents or minimizes fatigue by alternately resting and stimulating targeted muscle groups and thereby preventing the tongue from falling into a position that can cause apnea or hypopnea. The predetermined amount of time that a group is programmed to stay on may be determined by observing the tongue at a chosen stimulation frequency and determining how long the resulting contraction can be maintained before fatigue causes the resulting position control to degrade.

In another embodiment, each contact is pulsed at a fraction of the total target frequency (discussed below) and out of phase with each of the other contacts (FIG. 10B). For example, if the target frequency is 30 pps, each contact is pulsed at 10 pps with the other contacts interleaved between each pulse rather than pulsing each contact for an interval at 30 pps as shown in FIG. 9. In such an embodiment, the pulses are out of phase with one another so each contact pulses sequentially in a nearly continuous pattern to share the stimulation load of the contacts. Spreading the load over each of the contacts allows a much lower frequency to be used that allows for near constant muscle stimulation without or substantially without fatigue or diminished positioning.

Using multiple functional groups, in either a staggered or interleaved configuration, allows the tongue to be continuously or near-continuously stimulated, maintaining the tongue in a desired position even though each functional group only stimulates its neural population for a portion of a stimulation cycle. This exemplary method maintains continuous or near-continuous stimulation by load sharing between multiple functional groups, with each group—activating one or more desired tongue muscle. This method has the additional feature that group ramps would occur once for a sleep session and that stimulation levels would be maintained at their target levels, reducing the complexity of stimulation control.

Stimulus Ramping

FIGS. 9 and 52 illustrate an exemplary stimulus ramp. In certain exemplary embodiments, a stimulus ramp is used to maximize patient comfort and/or for prevention of arousal. With a patient who is awake, stimulation producing a noticeable, smooth contraction is important. In treating a sleeping patient suffering from obstructive sleep apnea, however, achieving the smallest contraction necessary to treat the condition—without waking the patient—is important. The contraction only needs to be sufficient to move the tongue forward enough or make airway (the pharyngeal wall) tense/ rigid enough to prevent an apnea event from occurring, and may not even be visible to the naked eye.

The sensation of the applied electrical pulses to the nerve, and the accompanying involuntary movement of the tongue generates is, at best, unnatural. In certain exemplary embodiments, the goal is to minimize sensation to a level acceptable to the patient. In certain exemplary embodiments, stimulus is gradually ramped up to ease the patient up to a target stimulus level. Stimulus starts at a threshold level, with stimulus magnitude slowly increasing to the target level. As is known to those skilled in the art, either stimulus magnitude or phase duration may be modulated to achieve control between the threshold and target levels.

If stimulation were immediately applied without a ramp, the stimulation could awaken or arouse the patient and adversely affect their sleep, just as an apnea event would. The exemplary embodiments of the present invention therefore employ the method of amplitude magnitude ramps at the start of stimulation to address this issue. The duration of this ramp is often several seconds long so that the change is gradual and the patient is able to adjust to the delivery of stimulation to the tissue.

In certain exemplary embodiments, an amplitude ramp of approximately 5 to 10 seconds is selected, (i.e., where stimulus increases to a desired level in 5 to 10 seconds). Stimulation is started at the threshold amplitude and slowly increased to the target amplitude until significant tongue movement is observed. Significant movement is defined as at least one movement that decreases airway resistance or results in increased airway air flow, or which maintains tongue muscle tone. The movement of the tongue and its affect on the airway can be observed with an endoscope placed in the nasal cavity, by use of fluoroscopy, or by observing the front of the oral cavity and the overall position of the tongue. Other ways of observing known to those skilled in the art can be used without departing from the scope of the invention. This is the operational point or targeted stimulation level that will be used if it is decided that this contact is to be included in the programmed stimulation protocol designed to affect the tongue during the sleeping session.

Frequency Adjustment

Another factor affecting the perceived comfort for the patient is the frequency of a pulsatile waveform. Stimulating at a very low frequency, such as approximately 1 to 3 pps, allows the easy identification of an amplitude threshold as distinct twitches or brief contractions of the muscle. These twitches or contractions are readily discernible, and often can be felt by the patient. Increasing the frequency to a sufficiently fast rate results in the fusion of the twitches (referred to as tetanus) and the relaxation between them into a smooth muscle contraction. This also quite often results in a sensation that is more comfortable for the patient, and is it is generally more comfortable for the patient as the frequency increases. Above a certain frequency, however, the sensation may again become uncomfortable, possibly associated with the level of work associated with the increased number of muscle contractions. This comfort level must be experimentally determined and it can vary from patient to patient. The amplitude is then increased to the target amplitude to sufficiently position the tongue as described above.

Delayed Stimulation Onset

In certain embodiments, stimulation is delayed until after a patient is asleep. By monitoring a patient in a sleep laboratory and/or by interviewing a patient's partner, it can be determined how much time is necessary to delay stimulation onset. In certain embodiments, this delay is programmed into the IPG 1370. When the patient initiates a sleep session of the device, the IPG 1370 then waits for the programmed delay period to complete before applying stimulation to the Hypoglossal nerve. The delay for stimulation onset may also be associated with the point at which sleep apnea begins to appear in the sleep cycle of the patient. If apneas do not begin to appear until the deepest stage of sleep (rapid eye movement or REM) then it may be advantageous to delay the onset of stimulation well past the point at which the patient begins to sleep and until just before the point at which apnea becomes apparent. The stimulation may then be applied for a predetermined period of time and/or until the IPG 1370 is deactivated. In one embodiment, the IPG 1370 is activated and deactivated via the RCC 2272.

Delaying stimulation onset, using frequency and/or amplitude modulation for a gradual ramp up or down to a desired stimulation all reduce the chances of arousing the patient in the middle of sleep, making tonic stimulation more likely to succeed. In certain treatment methods, sleeping medication for those patients who may be sensitive to the electrical stimulation activated movement may increase the chances of successful treatment.

In an exemplary embodiment, a stimulation amplitude threshold is determined by initially setting a low stimulation frequency between 1 and 3 pps. A typical waveform such as 200 μs cathodic phase duration, 50 μs interphase interval and 800 μs anodic phase duration is selected (the anodic phase amplitude would then be one fourth the amplitude of the cathodic phase amplitude), and then waveform amplitude is slowly increased from approximately 0 μA up to a level at which the tongue muscle can be seen to twitch with each pulse, or when the patient begins to feel the pulsatile sensation. This is the point at which the electrical stimulation is just enough to excite fibers within the nerve bundle. This setting is noted as the threshold amplitude and stimulation is stopped.

Each contact may be further tested to see what frequency should be used for initial stimulation. Experience and literature evidence suggests that the higher the frequency, the more comfortable the sensation of electrical stimulation is for the patient. The more comfortable the stimulation, the less likely the patient will be awakened. In these exemplary embodiments, stimulation starts at a frequency above the target frequency, and gradually decreases to the preferred target frequency. A preferred frequency is a frequency comfortable to the patient that produces a desired stimulus response. In one embodiment, one or more contacts deliver the target frequency at different intervals (FIGS. 9 and 10A). In another embodiment, the target frequency is generally divided by the number of contacts and is spread or interleaved over the contacts (FIG. 10C).

Determining the starting frequency is performed by setting the contact stimulation parameters to those determined for target stimulation and including an amplitude ramp, typically 5 to 10 seconds. Stimulation is started and the frequency is slowly adjusted upwards, checking with the patient for comfort. It may be necessary to reduce amplitude with higher frequency in order to maintain comfort but if so, then the target frequency should be checked again at the lower amplitude to verify that it still produces a functional movement.

Once all of the contacts have been evaluated a common higher frequency should be selected which is the lowest of all of the contact frequencies. The frequency is set to the lowest contact frequency that achieves a response resulting in increased airway airflow or decreased airway resistance.

Using the lowest frequency increases the time until fatigue occurs. This frequency is used as the startup frequency to be used after the delay from the beginning of the session has completed.

Exemplary Method of Use

The section below describes an exemplary method of patient use of the system. In the method described, the patient uses a remote control and charger 2272 (RCC) to operate and maintain the system. In this embodiment, the combination remote control and charger has a mini-USB connector, which charges an internal battery in the RCC 2272. Optionally the RCC 2272 may rest in a cradle kept on the patient's nightstand. The cradle would have spring loaded contacts, which make connection to the RCC 2272 much like a cordless phone to charge the RCC battery. The cradle may also use a mini-USB connector to attach to a wall mounted power supply.

To start a sleep session the patient uses the RCC 2272 to activate the implantable pulse generator (IPG). In certain embodiments, the patient first activates the RCC 2272, which then attempts to communicate to the IPG 1370. If the RCC 2272 is unable to communicate with the IPG 1370, the RCC 2272 indicates to the patient (by, for example, beeping three times and illuminating an LED) that the RCC 2272 could not communicate with the IPG 1370. This might mean that the IPG 1370 is so low in battery power that the IPG 1370 needs to be charged, or that the RCC 2272 is not close enough to communicate to the IPG 1370. If the IPG 1370 needs charging then the patient would attach a charge coil and cable to the RCC 2272, place the coil over the IPG 1370, press the charge switch on the RCC 2272 and charge the IPG 1370 until the battery of the IPG 1370 has enough energy to stimulate, up to two or three hours for a completely depleted IPG 1370.

If the IPG 1370 has enough energy to communicate and is in range of the RCC 2272, then the RCC 2272 would acquire the stimulation status and battery level. Assuming that this is the start of a normal sleep session the IPG 1370 would have been in the "Stimulation Off" state. The RCC 2272 then reports the battery status by indicating the battery LED in the green state for full, amber for medium and red for low. If the battery level is full or medium then the IPG 1370 would be instructed to start a sleep session and the IPG 1370 On/Off LED would be set to green. If the battery were low then the IPG 1370 would be instructed to stay off and the IPG On/Off LED would be set to red. The patient could then charge the IPG 1370 to use for one or more sleep sessions.

Once a sleep session starts, the IPG 1370 initiates a startup delay period allowing the patient to fall asleep before stimulation starts. At the end of this delay, stimulation starts with the first functional group, ramping amplitude from threshold to target amplitude and then holding for the remainder of its On-Time duration. In interleaved or staggered mode, all groups would start simultaneously, utilizing their individual ramp up parameters, then maintain stimulation levels at the target levels for the duration of the sleep period. At the beginning of stimulation, the stimulation frequency is set to the startup frequency determined during programming. This frequency would be ramped downwards to the target frequency for a programmed duration after which the target frequency is used.

Alternative Embodiments

Figure 53:
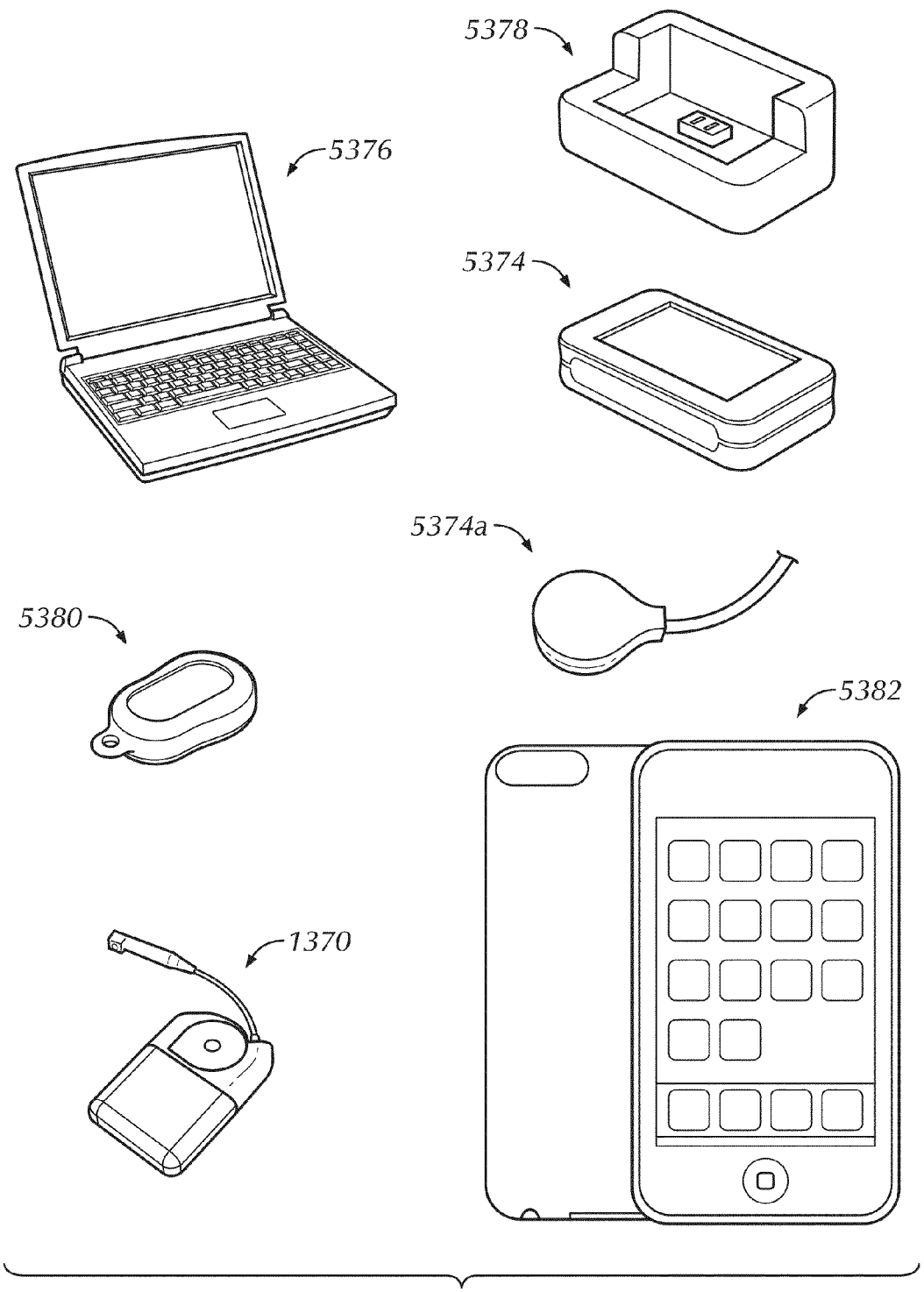
FIG. 53 is an exemplary representation of alternative embodiments of the system elements.

FIGS. 53 through 62 depict alternative embodiments of the OSA system that may be considered as alternatives to the system elements described above. FIG. 53 depicts the various elements that could be alternatively and/or additionally used: a small charger that may or may not have a user interface, a keyfob 5380 that may or may not have a user interface, and a remote control that may take advantage of commercially available devices, such as a hand-held computer, smart phone 5382, or similar commercially available device, which may provide useful wireless interfaces and user interfaces for the OSA application.

Figure 54:
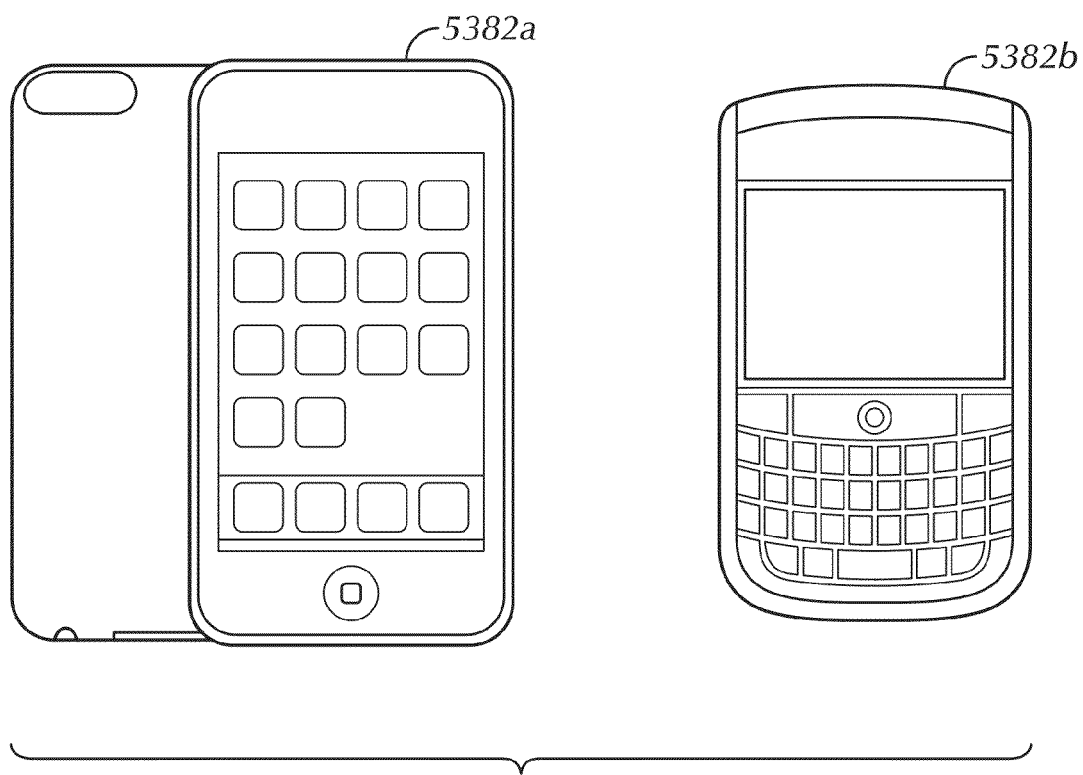
FIG. 54 depicts an alternative embodiment of a Remote Control.

FIG. 54 depicts a pair of exemplary devices which could act as remote controls. On the left is the Apple iPod® Touch 5382*a*, and on the right is a Blackberry® Smartphone 5382*b*. Both devices have excellent user interfaces, have wireless technology support to allow communication to the various OSA system elements, and are readily available and understandable by many of the patients that could use the OSA system.

Figure 55:
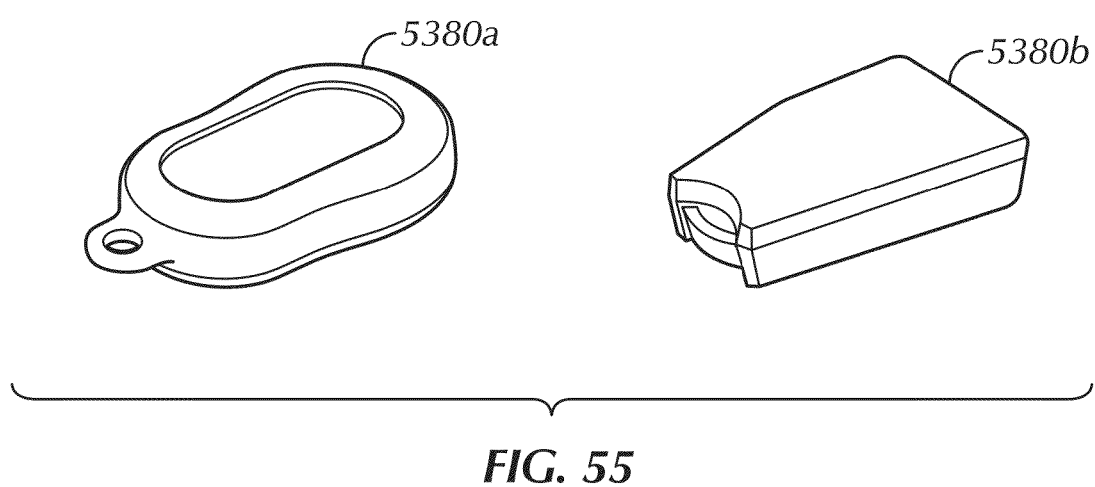
FIG. 55 depicts keyfob telemetry relays.

FIG. 55 depicts a keyfob telemetry relay that could be used to provide a communication bridge between the remote control and the IPG 1370. Standard wireless technologies, such as Bluetooth® or Wi-Fi could be implemented within the keyfob relay, along with MICS telemetry for communication to the IPG 1370. The keyfob relay need only be within telemetry range of the IPG 1370 and the remote control, for instance, in the pocket of the patient. Since the keyfob 5380 may only be required as a relay device, current consumption may be quite low, and the keyfob 5380 could run off a small lithium primary coin cell battery that would only need to be changed after rather long periods of time. Since the keyfob 5380 may only act as a relay, the keyfob 5380 may not need a user interface (such as a keyboard or LED display) at all, but if desired, either or both of these could be added. Alternatively, the remote control could allow the insertion of a hardware relay function to provide MICS telemetry directly from the remote control to the IPG.

Figure 56:
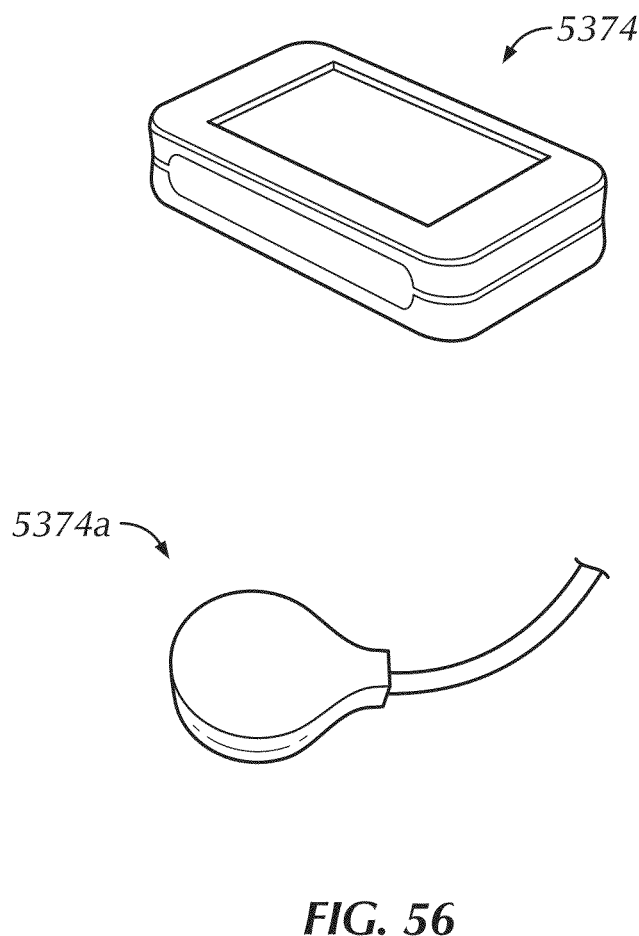
FIG. 56 depicts an alternative embodiment of a Charger and Charger Coil.

FIG. 56 depicts an exemplary charger and charger coil. This element may also have no user interface such as a keyboard or LED displays, but they could be added if desired.

Figure 57:
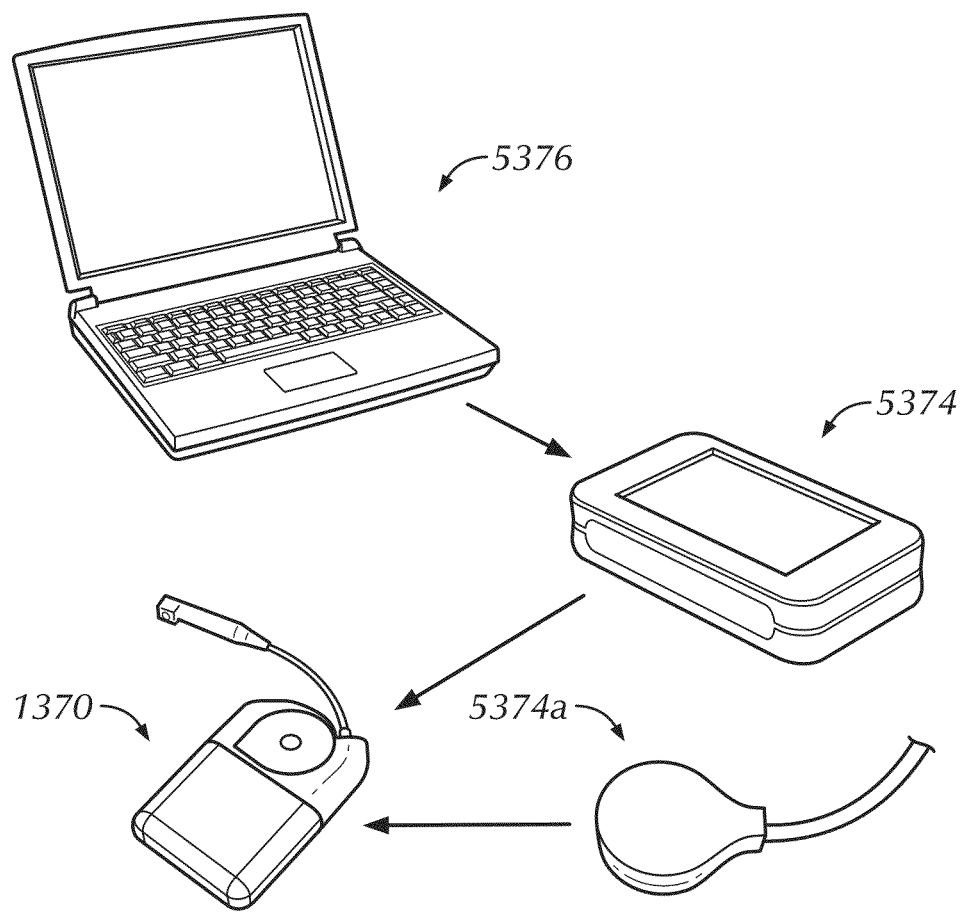
FIG. 57 depicts an alternative use model for the Clinician.
Figure 58:
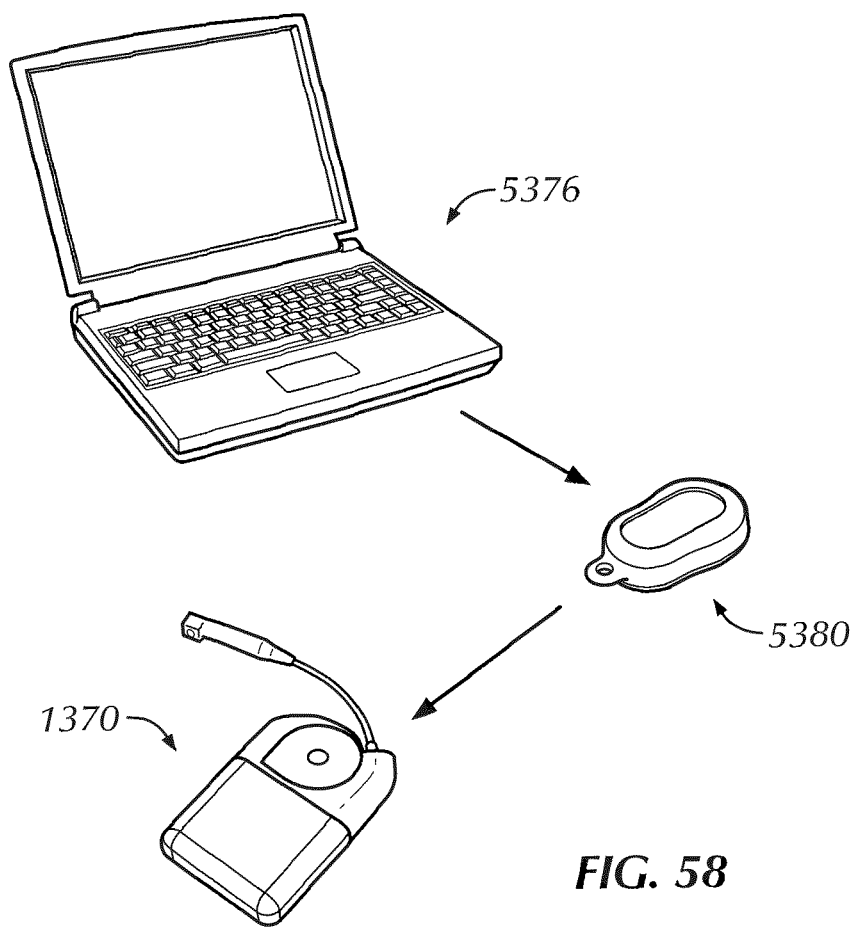
FIG. 58 depicts an another alternative use model for the Clinician.

FIG. 57 illustrates a potential use model for the alternative embodiments for use by the clinician in programming or interrogating the OSA system. The aCM could be the same as that described previously, and a wireless interface such as Bluetooth® or Wi-Fi could be used to communicate with the charger. The charger could then communicate with the IPG 1370 using MICS telemetry, or if that were not possible for some reason, then the charger coil (CC) could be used as a backup telemetry channel. Alternatively, as depicted in FIG. 58, the aCM could communicate through the keyfob relay to the IPG 1370. Using Bluetooth®, Wi-Fi or some other industry standard wireless interface between the aCM and the keyfob 5380, and MICS telemetry between the keyfob relay and the IPG 1370, communication could be provided to program or interrogate the IPG 1370 in the OSA system. Alternatively, the aCM computer could allow the insertion of a hardware relay function to provide MICS telemetry directly from the aCM to the IPG.

Figure 60:
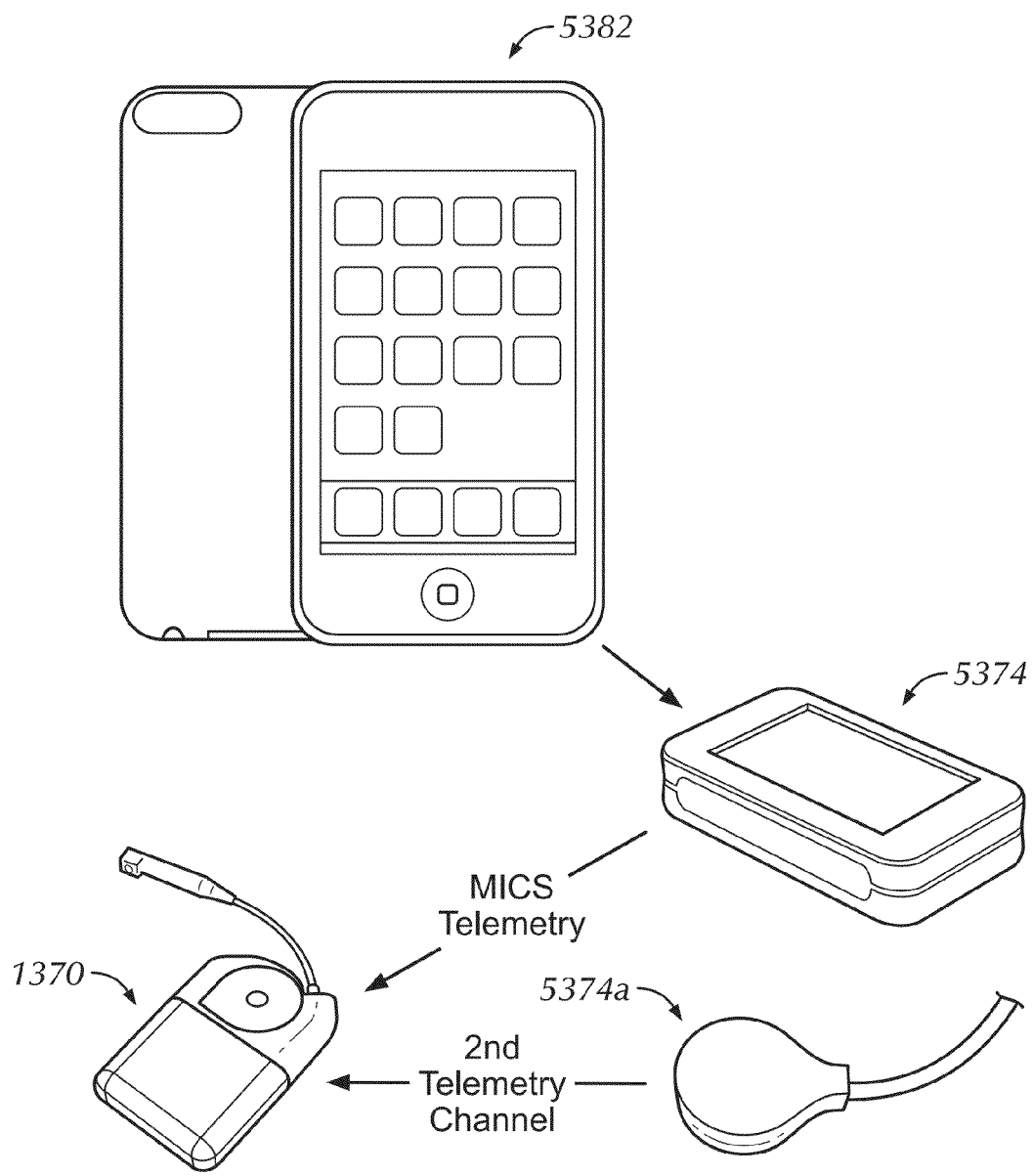
FIG. 60 depicts another use model for the patient.
Figure 61:
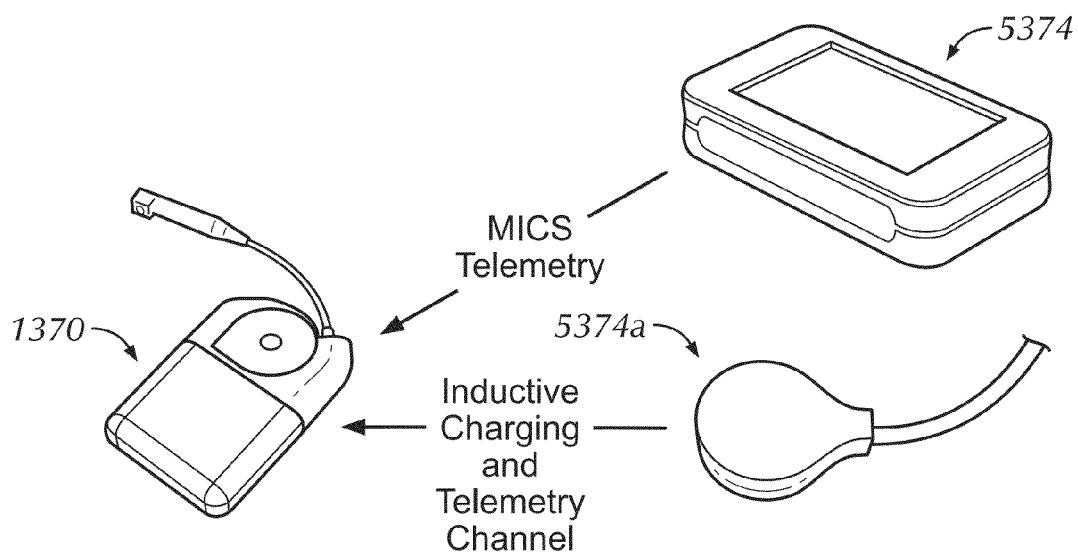
FIG. 61 depicts a use model for the patient when charging the IPG.

FIG. 58 illustrates the use of the iPhone® (or SmartPhone) 5382 as the remote control to perform routine operations in the OSA system. The remote control would communicate with the keyfob 5380 which would relay the communication with the IPG 1370 via MICS telemetry. FIG. 60 illustrates that the charger and telemetry coil could take the place of the keyfob 5380 by providing MICS telemetry or secondary inductive link telemetry should the MICS telemetry be non-functional for some reason.

Figure 59:
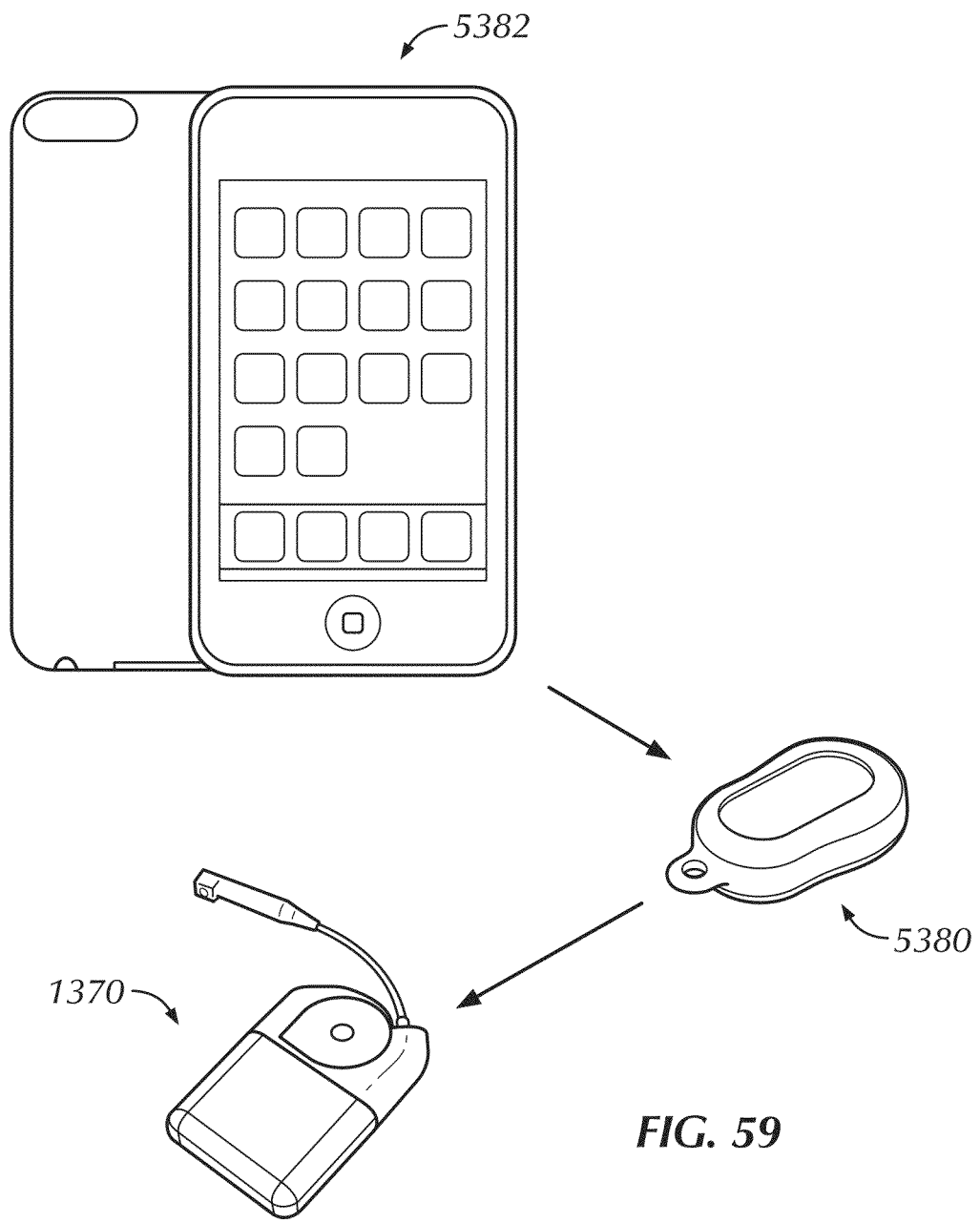
FIG. 59 depicts a use model for the patient.
Figure 62:
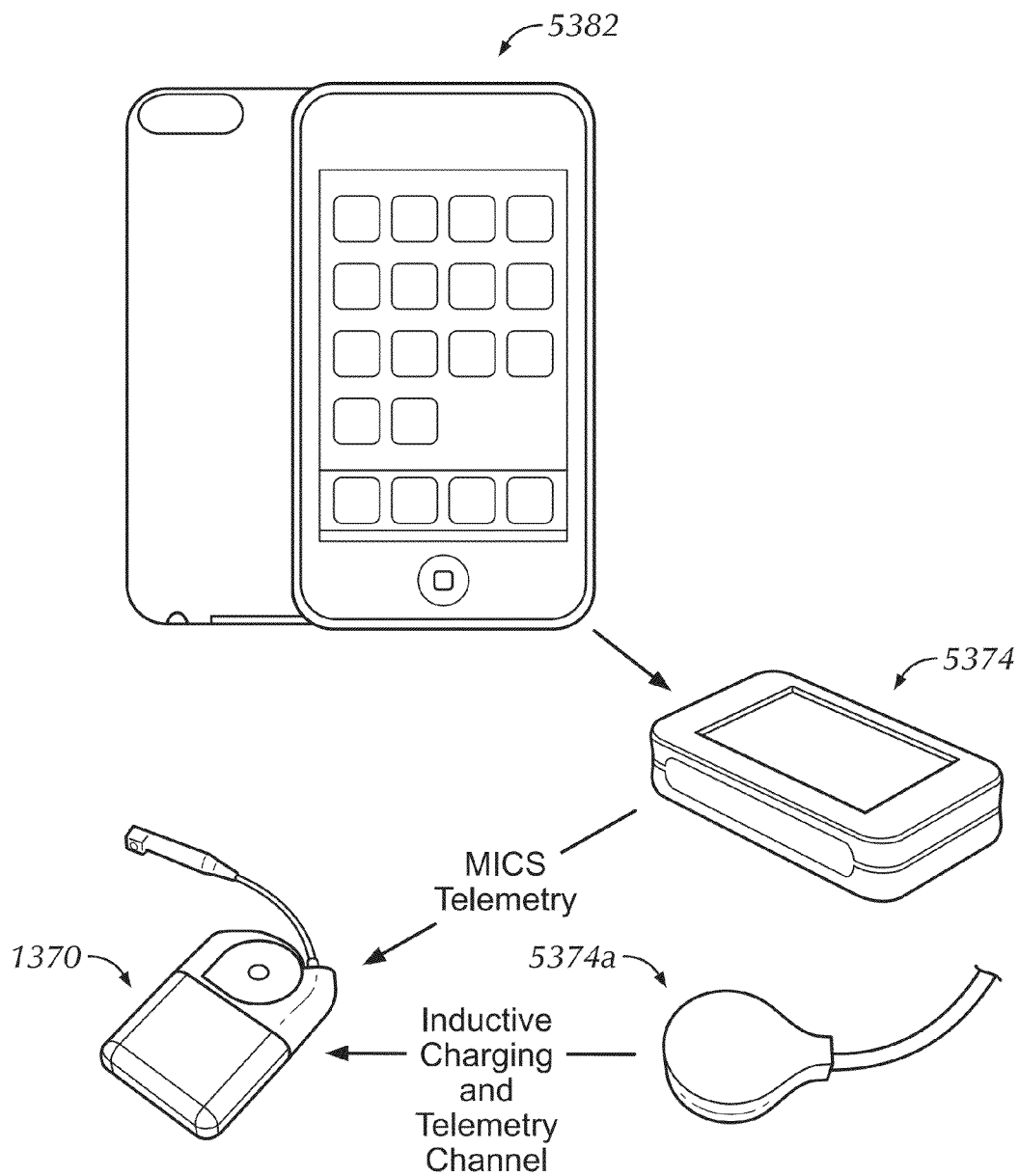
FIG. 62 depicts another use model for the patient when charging the IPG.

FIG. 59 illustrates the use of the simplified charger and charger coil for charging of the IPG 1370. The charger would normally be placed upon a cradle or docking station 5378 to re-charge its own internal battery supply, possibly a lithium polymer battery. A microcontroller inside of the charger could detect when the patient removes the charger from its cradle and begin to automatically search for the IPG 1370. Once the IPG 1370 is located and it has determined that the charger coil is placed over the IPG 1370 it may then proceed to charge the IPG 1370 as described previously. If the charger did not find the IPG 1370 within say five minutes of removal from the cradle or docking station 5378, then if the charger had a membrane switch panel or other user interface it could be independently commanded to start or stop the charging process. Again, alternatively, and as depicted in FIG. 62, the remote control could be used to communicate with the charger to start and/or stop the charging process.

It shall be understood that these and many other embodiments of the OSA system could be implemented that would provide the OSA treatment, maintain the operation of the OSA system, and provide information to the patient and clinician for routine use, programming and maintenance of the OSA sleep therapy.

It will be appreciated by those skilled in the art that changes could be made to the exemplary embodiment shown and described above without departing from the broad inventive concept thereof. It is understood, therefore, that this invention is not limited to the exemplary embodiment shown and described, but it is intended to cover modifications within the spirit and scope of the present invention as defined by the claims. For example, "an embodiment," and the like, may be inserted at the beginning of every sentence herein where logically possible and appropriate such that specific features of the exemplary embodiment may or may not be part of the claimed invention and combinations of disclosed embodiments may be combined. Unless specifically set forth herein, the terms "a", "an" and "the" are not limited to one element but instead should be read as meaning "at least one".

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. A method for controlling a position of a patient's tongue, the method comprising:
    implanting an electrode having a plurality of contacts, the plurality of contacts being proximate a Hypoglossal nerve;
    implanting an implantable pulse generator (IPG), the IPG being electronically coupled to the electrode;
    programming the IPG, independent of respiration cycle, to deliver at least two electric signals to the plurality of contacts;
    applying the at least two electric signals at a starting frequency via the plurality of contacts to at least two targeted motor efferent groups located within the Hypoglossal nerve to stimulate at least two muscles of the tongue; and
    ramping the starting frequency downwards to a target frequency,
    wherein programming the IPG includes:
        assigning each contact to one of a plurality of functional groups,
        keeping an amplitude of at least one electric signal of a first functional group at a target amplitude for a predetermined amount of time and then replacing the at least one electric signal of the first functional group with at least one electric signal of a second functional group of the plurality of functional groups,
        ramping an amplitude of the at least one electric signal of the second functional group from an initial level up to the target amplitude, and
        ramping the amplitude of the at least one electric signal of the second functional group from the target amplitude down to a rest amplitude.

2. The method of claim 1, wherein programming the IPG includes sequencing or interleaving the plurality of functional groups.

3. The method of claim 1, wherein programming the IPG includes ramping the amplitude of the at least one electric signal of the first functional group of the plurality of functional groups from an initial level up to the target amplitude.

4. The method of claim 1, wherein a period of the at least one electric signal of the first functional group partially overlaps with a period of the at least one electric signal of the second functional group.

5. The method of claim 1, wherein a period of the at least one electric signal of the first functional group does not overlap with a period of the at least one electric signal of the second functional group.

6. The method of claim 1, wherein programming the IPG includes sharing a generally level amount of stimulation between the plurality of contacts.

7. The method of claim 1, wherein applying the at least two electric signals includes driving each contact by their own independent current source.

8. The method of claim 1, wherein programming the IPG includes pulsing each contact at different or overlapping intervals.

9. The method of claim 1, wherein the electrode includes a cuff housing and wherein implanting the electrode includes wrapping the cuff housing around a portion of the Hypoglossal nerve.

10. The method of claim 1, wherein the at least two electric signals are applied to the Hypoglossal nerve via an open loop system.

11. The method of claim 1 further comprising: initiating a therapy session, wherein the applying the at least two electric signals is delayed for a predetermined amount of time after initiating the therapy session.

12. The method of claim 1, wherein the at least two electric signals are applied at least once during both inhalation and exhalation of a respiration cycle.

13. The method of claim 1, wherein the at least two electric signals are applied simultaneously.

* * * * *